United States Patent
Kovacevich et al.

(10) Patent No.: US 11,560,431 B2
(45) Date of Patent: *Jan. 24, 2023

(54) ANTI-PD-L1 ANTIBODIES AND METHODS OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Brian Kovacevich, Snohomish, WA (US); Dong Xia, Redmond, WA (US); Anne E. Jensen, Mill Creek, WA (US); Jonathan K. Fallen, Quincy, MA (US); Blair Renshaw, Renton, WA (US); Jeffrey B. Adamo, Seattle, WA (US); Phil Tan, Edmonds, WA (US); Zeren Gao, Redmond, WA (US); Yi Zhu, Chengdu (CN)

(73) Assignee: BAILI-BIO (CHENGDU) PHARMACEUTICAL CO., LTD., Chengdu (CN)

( * ) Notice: Subject to any disclaimer, the term of this patent is extended or adjusted under 35 U.S.C. 154(b) by 366 days.

This patent is subject to a terminal disclaimer.

(21) Appl. No.: 16/615,112

(22) PCT Filed: Jun. 22, 2018

(86) PCT No.: PCT/US2018/039144
§ 371 (c)(1),
(2) Date: Nov. 19, 2019

(87) PCT Pub. No.: WO2019/005634
PCT Pub. Date: Jan. 3, 2019

(65) Prior Publication Data
US 2022/0002417 A1 Jan. 6, 2022

Related U.S. Application Data

(60) Provisional application No. 62/524,553, filed on Jun. 25, 2017.

(51) Int. Cl.
*C07K 16/28* (2006.01)
*A61P 35/00* (2006.01)
*A61K 39/395* (2006.01)
*A61K 45/06* (2006.01)

(52) U.S. Cl.
CPC .... *C07K 16/2827* (2013.01); *A61K 39/39541* (2013.01); *A61K 45/06* (2013.01); *A61P 35/00* (2018.01); *C07K 2317/24* (2013.01); *C07K 2317/31* (2013.01); *C07K 2317/76* (2013.01); *C07K 2317/92* (2013.01)

(58) Field of Classification Search
CPC ............ C07K 16/2827; C07K 2317/24; A61K 39/39541; A61K 45/06
See application file for complete search history.

(56) References Cited

U.S. PATENT DOCUMENTS

| | | | | |
|---|---|---|---|---|
| 2020/0347137 A1* | 11/2020 | Zhu | .................... | C07K 16/2827 |
| 2021/0024630 A1* | 1/2021 | Zhu | .................... | C07K 16/2863 |
| 2022/0002406 A1* | 1/2022 | Zhu | .................... | C07K 16/2827 |

OTHER PUBLICATIONS

Almagro & Fransson, Humanization of antibodies, Frontiers in Bioscience 2008; 13: 1619-33 (Year: 2008).*
Rudikoff et al., Single amino acid substitution altering antigen-binding specificity, PNAS, USA, 1982, 79: 1979-1983 (Year: 1982).*
Tannock, 19 Experimental Chemotherapy, The Basic Science of Oncology, 2nd Edition, Publish Year:1992 (Year: 1992).*
Scott et al., Antibody therapy of cancer, Nature Review Cancer, 12, 278-287, Publication Date: Apr. 2012 (Year: 2012).*
Labrijn et al. Efficient generation of stable bispecific IgG1 by controlled Fab-arm exchange, PNAS, 110 (13); 5145-5150 and Supporting Information; Publication Date: Mar. 26, 2013 (Year: 2013).*

* cited by examiner

*Primary Examiner* — Peter J Reddig
*Assistant Examiner* — Cheng Lu
(74) *Attorney, Agent, or Firm* — Zhihua Han

(57) ABSTRACT

The application provides the anti-PD-L1 monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

16 Claims, 7 Drawing Sheets

Specification includes a Sequence Listing.

FIGURE 1 shows an example of the PD-L1 binding ELISA performed on the supernatants from a B cell culture plate. Shaded wells indicate wells that were identified as positive for anti-PD-L1 antibodies.

|   | 1 | 2 | 3 | 4 | 5 | 6 | 7 | 8 | 9 | 10 | 11 | 12 |
|---|---|---|---|---|---|---|---|---|---|----|----|----|
| A | 0.335 | 0.056 | 0.058 | 0.051 | 0.061 | 0.058 | 0.05 | 0.068 | 0.059 | 0.054 | 0.094 | 0.106 |
| B | 0.091 | 0.042 | 0.047 | 0.05 | 0.042 | 0.05 | 0.044 | 0.051 | 0.057 | 0.047 | 0.044 | 0.179 |
| C | 0.052 | 0.045 | 0.048 | 0.054 | 0.044 | 0.058 | 0.09 | 0.049 | 0.048 | 0.047 | 0.049 | 0.087 |
| D | 0.066 | 0.049 | 0.054 | 0.048 | 0.043 | 0.054 | 0.05 | 0.047 | 0.172 | 0.045 | 0.044 | 0.071 |
| E | 0.052 | 0.051 | 0.051 | 0.522 | 0.043 | 0.048 | 0.043 | 0.052 | 0.044 | 0.058 | 0.047 | 0.052 |
| F | 0.056 | 0.052 | 0.056 | 0.046 | 0.044 | 0.047 | 1.375 | 0.048 | 0.047 | 0.046 | 0.048 | 0.16 |
| G | 0.308 | 0.059 | 0.063 | 0.057 | 0.056 | 0.076 | 0.062 | 0.145 | 0.047 | 0.049 | 0.047 | 0.051 |
| H | 0.087 | 0.079 | 0.06 | 0.06 | 0.06 | 0.059 | 1.267 | 0.052 | 0.059 | 0.056 | 0.063 | 0.106 |

FIGURE 2 is an example of bio-layer interferometry analysis of the ability of an antibody supernatant to block the association between PD-L1 to PD-1. The black trace utilizes a block antibody supernatant whereas the gray trace is with a non-blocking antibody supernatant. Octet analysis of PD-1 binding to biotinylated PD-L1 loaded onto a streptavidin sensor after the addition of PD-L1 specific antibodies that block or do not block PD-1 binding to PD-L1.

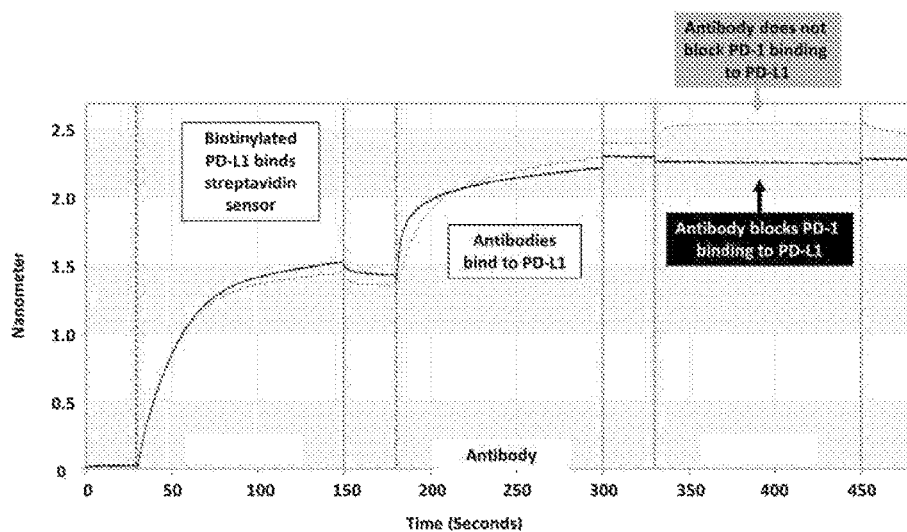

FIGURE 3 shows bio-layer interferometry analysis of the ability of antibodies AB1 – AB5 to block the association between PD-L1 to PD-1, starting from PD-L1 binding followed by baseline and PD-L1 binding. Negative control is an anti-PD-L1 antibody which can bind to PD-L1 but does not block the association between PD-L1 to PD-1. Octet analysis indicates that a control PD-L1 specific antibody binding to biotinylated PD-L1 loaded onto a streptavidin sensor does not block PD-1 binding to PD-L1.

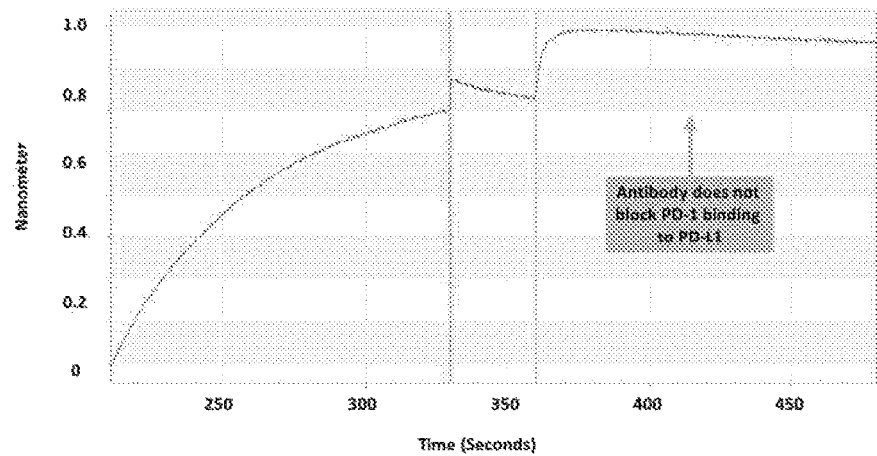

FIGURE 4 is an example of binding kinetics data for two anti-PD-L1 antibodies binding to PD-L1. The data shown is for the 5-minute association followed by the 15-minute dissociation for various concentrations of PD-L1. 4A shows AB1HU blocking recombinant PD-1 binding to recombinant PD-L1; 4B shows AB2HU blocking recombinant PD-1 binding to recombinant PD-L1; 4C shows AB3HU blocking recombinant PD-1 binding to recombinant PD-L1; 4D shows AB4HU blocking recombinant PD-1 binding to recombinant PD-L1; and 4E shows AB5HU blocking recombinant PD-1 binding to recombinant PD-L1.

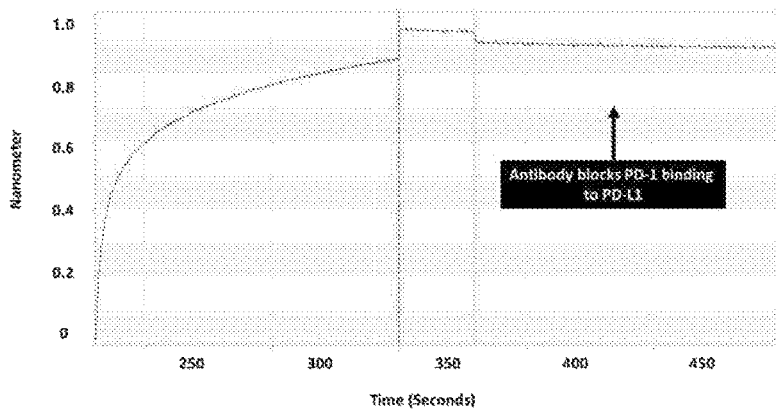

FIGURE 4A

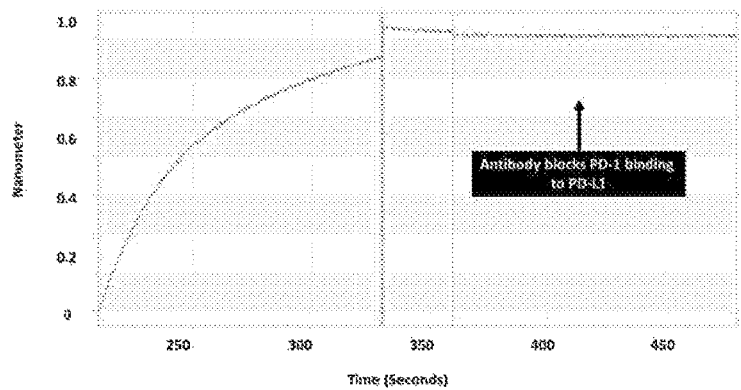

FIGURE 4B

FIGURE 5 shows the example antibodies binding to lung cancer cell line A441.
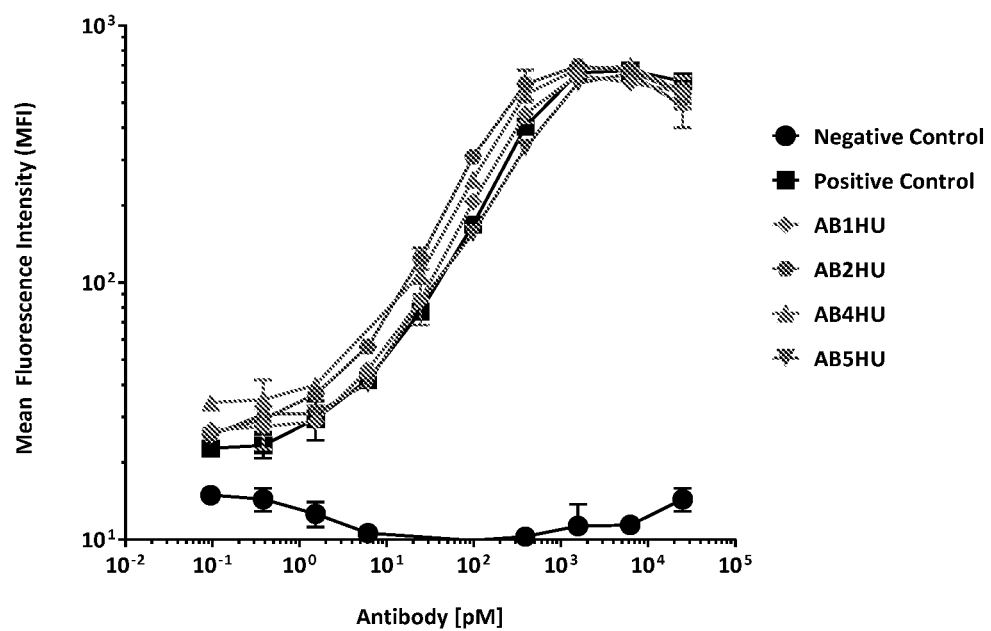

SEQUENCE LISTING

<160> NUMBER OF SEQ ID NOS: 84

<210> SEQ ID NO 1
<211> LENGTH: 651
<212> TYPE: DNA
<213> ORGANISM: Artificial Sequence
<220> FEATURE:
<223> OTHER INFORMATION: synthesized

<400> SEQUENCE: 1

```
gaccctgtgc tgacccagac tccagcctct gtggaggtag ctgtgggagg cacagtcacc        60
atcaagtgcc aggccagtca gagcattagt tcccacttaa actggtatca gcagaaacca       120
gggcagcctc ccaagctcct gatctacaag gcatccactc tggcatctgg gtcccatcg        180 cgtttcaaag gcagtggatc tgggacagag ttcactctca ccatcagcag tgtgcagtgt       240
gacaatgctg ccacttatta ctgtcaacag ggttatagtt ggggtaatgt tgataatgtt       300
ttcggcggag ggaccgaggt ggtggtcaaa cgtacggtgg ctgcaccatc tgtcttcatc       360
ttcccgccat ctgatgagca gttgaaatct ggaactgcct ctgttgtgtg cctgctgaat       420
aacttctatc ccagagaggc caaagtacag tggaaggtgg ataacgccct ccaatcgggt       480
aactcccagg agagtgtcac agagcaggac agcaaggaca gcacctacag cctcagcagc       540
accctgacgc tgagcaaagc agactacgag aaacacaaag tctacgcctg cgaagtcacc       600
catcagggcc tgagctcgcc cgtcacaaag agcttcaaca ggggagagtg t                651
```

<210> SEQ ID NO 2
<211> LENGTH: 330
<212> TYPE: DNA
<213> ORGANISM: Artificial Sequence
<220> FEATURE:
<223> OTHER INFORMATION: synthesized

<400> SEQUENCE: 2

```
gaccctgtgc tgacccagac tccagcctct gtggaggtag ctgtgggagg cacagtcacc        60
atcaagtgcc aggccagtca gagcattagt tcccacttaa actggtatca gcagaaacca       120
```

-continued

```
gggcagcctc ccaagctcct gatctacaag gcatccactc tggcatctgg ggtcccatcg    180
cgtttcaaag gcagtggatc tgggacagag ttcactctca ccatcagcag tgtgcagtgt    240
gacaatgctg ccacttatta ctgtcaacag ggttatagtt ggggtaatgt tgataatgtt    300
ttcggcggag ggaccgaggt ggtggtcaaa                                      330
```

<210> SEQ ID NO 3
<211> LENGTH: 217
<212> TYPE: PRT
<213> ORGANISM: Artificial Sequence
<220> FEATURE:
<223> OTHER INFORMATION: synthesized

<400> SEQUENCE: 3

```
Asp Pro Val Leu Thr Gln Thr Pro Ala Ser Val Glu Val Ala Val Gly
1               5                   10                  15

Gly Thr Val Thr Ile Lys Cys Gln Ala Ser Gln Ser Ile Ser Ser His
            20                  25                  30

Leu Asn Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
 50                  55                  60

Ser Gly Ser Gly Thr Glu Phe Thr Leu Thr Ile Ser Ser Val Gln Cys
65                  70                  75                  80

Asp Asn Ala Ala Thr Tyr Tyr Cys Gln Gln Gly Tyr Ser Trp Gly Asn
                85                  90                  95

Val Asp Asn Val Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 4
<211> LENGTH: 110
<212> TYPE: PRT
<213> ORGANISM: Artificial Sequence
<220> FEATURE:
<223> OTHER INFORMATION: Synthesized

<400> SEQUENCE: 4

```
Asp Pro Val Leu Thr Gln Thr Pro Ala Ser Val Glu Val Ala Val Gly
1               5                   10                  15

Gly Thr Val Thr Ile Lys Cys Gln Ala Ser Gln Ser Ile Ser Ser His
            20                  25                  30

Leu Asn Trp Tyr Gln Gln Lys Pro Gly Gln Pro Pro Lys Leu Leu Ile
        35                  40                  45
```

```
Tyr Lys Ala Ser Thr Leu Ala Ser Gly Val Pro Ser Arg Phe Lys Gly
    50                  55                  60

Ser Gly Ser Gly Thr Glu Phe Thr Leu Thr Ile Ser Ser Val Gln Cys
65                  70                  75                  80

Asp Asn Ala Ala Thr Tyr Tyr Cys Gln Gln Gly Tyr Ser Trp Gly Asn
                85                  90                  95

Val Asp Asn Val Phe Gly Gly Gly Thr Glu Val Val Val Lys
            100                 105                 110

<210> SEQ ID NO 5
<211> LENGTH: 1353
<212> TYPE: DNA
<213> ORGANISM: Artificial Sequence
<220> FEATURE:
<223> OTHER INFORMATION: Synthesized

<400> SEQUENCE: 5
caggagcagc tggtggagtc cggggggaggc ctggtccagc ctgagggatc cctgacactc      60
acctgtaaag cctctggatt ctccttcagt agcgggtacg acatgtgctg ggtccgccgg     120
gctccaggga aggggctgga gtggatcgca tgcattgctg ctggtagtgc tggtatcact     180
tacgacgcga actgggcgaa aggccgattc accatctcca aaacctcgtc gaccacggtg     240
actctacaaa tgaccagtct gacagccgcg gacacggcca cctatttctg tgcgagatcg     300
gcgttttcgt tcgactacgc catggacctc tggggcccag ggaccctcgt caccgtctcg     360
agcgctagca ccaagggccc atcggtcttc cccctggcac cctcctccaa gagcacctct     420
gggggcacag cggccctggg ctgcctggtc aaggactact ccccgaacc ggtgacggtg     480 tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc     780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353

<210> SEQ ID NO 6
<211> LENGTH: 363
<212> TYPE: DNA
<213> ORGANISM: Artificial Sequence
<220> FEATURE:
<223> OTHER INFORMATION: Synthesized

<400> SEQUENCE: 6
caggagcagc tggtggagtc cggggggaggc ctggtccagc ctgagggatc cctgacactc      60
```

```
acctgtaaag cctctggatt ctccttcagt agcgggtacg acatgtgctg ggtccgccgg      120
gctccaggga aggggctgga gtggatcgca tgcattgctg ctggtagtgc tggtatcact      180
tacgacgcga actgggcgaa aggccgattc accatctcca aacctcgtc gaccacggtg       240 actctacaaa tgaccagtct gacagccgcg gacacggcca cctatttctg tgcgagatcg      300
gcgttttcgt tcgactacgc catggacctc tggggcccag ggaccctcgt caccgtctcg      360
agc                                                                    363
```

<210> SEQ ID NO 7
<211> LENGTH: 451
<212> TYPE: PRT
<213> ORGANISM: Artificial Sequence
<220> FEATURE:
<223> OTHER INFORMATION: Synthesized

<400> SEQUENCE: 7

```
Gln Glu Gln Leu Val Glu Ser Gly Gly Gly Leu Val Gln Pro Glu Gly
1               5                   10                  15

Ser Leu Thr Leu Thr Cys Lys Ala Ser Gly Phe Ser Phe Ser Ser Gly
                20                  25                  30

Tyr Asp Met Cys Trp Val Arg Arg Ala Pro Gly Lys Gly Leu Glu Trp
            35                  40                  45

Ile Ala Cys Ile Ala Ala Gly Ser Ala Gly Ile Thr Tyr Asp Ala Asn
        50                  55                  60

Trp Ala Lys Gly Arg Phe Thr Ile Ser Lys Thr Ser Thr Thr Val
65                  70                  75                  80

Thr Leu Gln Met Thr Ser Leu Thr Ala Ala Asp Thr Ala Tyr Phe
                85                  90                  95

Cys Ala Arg Ser Ala Phe Ser Phe Asp Tyr Ala Met Asp Leu Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 8
<211> LENGTH: 121
<212> TYPE: PRT
<213> ORGANISM: Artificial Sequence
<220> FEATURE:
<223> OTHER INFORMATION: Synthesized

<400> SEQUENCE: 8

Gln Glu Gln Leu Val Glu Ser Gly Gly Gly Leu Val Gln Pro Glu Gly
1               5                   10                  15

Ser Leu Thr Leu Thr Cys Lys Ala Ser Gly Phe Ser Phe Ser Ser Gly
            20                  25                  30

Tyr Asp Met Cys Trp Val Arg Arg Ala Pro Gly Lys Gly Leu Glu Trp
        35                  40                  45

Ile Ala Cys Ile Ala Ala Gly Ser Ala Gly Ile Thr Tyr Asp Ala Asn
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Ser Ala Phe Ser Phe Asp Tyr Ala Met Asp Leu Trp Gly
            100                 105                 110

Pro Gly Thr Leu Val Thr Val Ser Ser
        115                 120

<210> SEQ ID NO 9
<211> LENGTH: 651
<212> TYPE: DNA
<213> ORGANISM: Artificial Sequence
<220> FEATURE:
<223> OTHER INFORMATION: synthesized

<400> SEQUENCE: 9
gacatccaga tgacccagtc tccttccacc ctgtctgcat ctgtaggaga cagagtcacc      60
atcacttgcc aggccagtca gagcattagt tcccacttaa actggtatca gcagaaacca     120

```
gggaaagccc ctaagctcct gatctataag gcatccactc tggcatctgg ggtcccatca    180
aggttcagcg gcagtggatc tgggacagaa tttactctca ccatcagcag cctgcagcct    240
gatgattttg caacttatta ctgccaacag ggttatagtt ggggtaatgt tgataatgtt    300
ttcggcggag ggaccaaggt ggagatcaaa cgtacggtgg ctgccaccat cgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t            651
```

<210> SEQ ID NO 10
<211> LENGTH: 330
<212> TYPE: DNA
<213> ORGANISM: Artificial Sequence
<220> FEATURE:
<223> OTHER INFORMATION: synthesized

<400> SEQUENCE: 10

```
gacatccaga tgacccagtc tccttccacc ctgtctgcat ctgtaggaga cagagtcacc     60
atcacttgcc aggccagtca gagcattagt tcccacttaa actggtatca gcagaaacca    120
gggaaagccc ctaagctcct gatctataag gcatccactc tggcatctgg ggtcccatca    180
aggttcagcg gcagtggatc tgggacagaa tttactctca ccatcagcag cctgcagcct    240
gatgattttg caacttatta ctgccaacag ggttatagtt ggggtaatgt tgataatgtt    300
ttcggcggag ggaccaaggt ggagatcaaa                                     330
```

<210> SEQ ID NO 11
<211> LENGTH: 217
<212> TYPE: PRT
<213> ORGANISM: Artificial Sequence
<220> FEATURE:
<223> OTHER INFORMATION: synthesized

<400> SEQUENCE: 11

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Trp Gly Asn
                85                  90                  95

Val Asp Asn Val Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160
```

```
Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
        180                 185                 190

Lys Val Tyr Ala Cys Glu Val Thr His Gln Gly Leu Ser Ser Pro Val
    195                 200                 205

Thr Lys Ser Phe Asn Arg Gly Glu Cys
    210                 215

<210> SEQ ID NO 12
<211> LENGTH: 110
<212> TYPE: PRT
<213> ORGANISM: Artificial Sequence
<220> FEATURE:
<223> OTHER INFORMATION: synthesized

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Gln Gly Tyr Ser Trp Gly Asn
                85                  90                  95

Val Asp Asn Val Phe Gly Gly Gly Thr Lys Val Glu Ile Lys
            100                 105                 110

<210> SEQ ID NO 13
<211> LENGTH: 1356
<212> TYPE: DNA
<213> ORGANISM: Artificial Sequence
<220> FEATURE:
<223> OTHER INFORMATION: synthesized

<400> SEQUENCE: 13
gaggtgcagc tgttggagtc tgggggaggc ttggtacagc ctggggggtc cctgagactc      60
tcctgtgcag cctctggatt ctccttcagt agcgggtacg acatgtgctg ggtccgccag     120
gctccaggga aggggctgga gtggatcgca tgcattgctg ctggtagtgc tggtatcact     180
tacgacgcga actgggcgaa aggccggttc accatctcca gagacaattc caagaacacg     240
ctgtatctgc aaatgaacag cctgagagcc gaggacacgg ccgtatatta ctgtgcgaga     300
tcggcgtttt cgttcgacta cgccatggac tctgggggcc agggaaccct ggtcaccgtc     360
tcgagcgcta gcaccaaggg cccatcggtc ttccccctgg cacccctcc caagagcacc     420 tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg     780
```

```
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagcccttcc cagcccccat cgagaaaacc   1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga caactacaa gaccacgcct     1200 cccgtgctgg actccgacgg ctccttcttc ctctatagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                              1356

<210> SEQ ID NO 14
<211> LENGTH: 366
<212> TYPE: DNA
<213> ORGANISM: Artificial Sequence
<220> FEATURE:
<223> OTHER INFORMATION: synthesized

<400> SEQUENCE: 14
gaggtgcagc tgttggagtc tgggggaggc ttggtacagc ctggggggtc cctgagactc     60
tcctgtgcag cctctggatt ctccttcagt agcgggtacg acatgtgctg ggtccgccag    120
gctccaggga aggggctgga gtggatcgca tgcattgctg ctggtagtgc tggtatcact    180
tacgacgcga actgggcgaa aggccggttc accatctcca gagacaattc caagaacacg    240
ctgtatctgc aaatgaacag cctgagagcc gaggacacgg ccgtatatta ctgtgcgaga    300
tcggcgtttt cgttcgacta cgccatggac ctctggggcc agggaaccct ggtcaccgtc    360
tcgagc                                                              366

<210> SEQ ID NO 15
<211> LENGTH: 452
<212> TYPE: PRT
<213> ORGANISM: Artificial Sequence
<220> FEATURE:
<223> OTHER INFORMATION: synthesized

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Ile Ala Cys Ile Ala Ala Gly Ser Ala Gly Ile Thr Tyr Asp Ala Asn
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ser Ala Phe Ser Phe Asp Tyr Ala Met Asp Leu Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 16
<211> LENGTH: 122
<212> TYPE: PRT
<213> ORGANISM: Artificial Sequence
<220> FEATURE:
<223> OTHER INFORMATION: synthesized

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30
```

```
Tyr Asp Met Cys Trp Val Arg Gln Ala Pro Gly Lys Gly Leu Glu Trp
         35                  40                  45

Ile Ala Cys Ile Ala Ala Gly Ser Ala Gly Ile Thr Tyr Asp Ala Asn
 50                  55                  60

Trp Ala Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Ser Ala Phe Ser Phe Asp Tyr Ala Met Asp Leu Trp
                100                 105                 110

Gly Gln Gly Thr Leu Val Thr Val Ser Ser
            115                 120
```

<210> SEQ ID NO 17
<211> LENGTH: 651
<212> TYPE: DNA
<213> ORGANISM: Artificial Sequence
<220> FEATURE:
<223> OTHER INFORMATION: synthesized

<400> SEQUENCE: 17

```
gcctatgata tgacccagac tccagcctcc gtgtctgcag ctgtgggagg cacagtcacc      60
atcaattgcc aggccagtga gagcattagt agcttcttat cctggtatca gcagaaacca     120
gggcagcgtc ccaggctcct gatctttttct gcatccactc tggcatctgg ggtcccatcg    180
cggttcaaag gcagtggatc tgggacagag ttcactctca ccatcagcgg cgtggagtgt    240
gccgatgctg ccacttatta ttgtcaacag ggttatagta aaagtaatgt ggataatgct    300
ttcggcggag ggaccgaggt ggtggtcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t              651
```

<210> SEQ ID NO 18
<211> LENGTH: 330
<212> TYPE: DNA
<213> ORGANISM: Artificial Sequence
<220> FEATURE:
<223> OTHER INFORMATION: synthesized

<400> SEQUENCE: 18

```
gcctatgata tgacccagac tccagcctcc gtgtctgcag ctgtgggagg cacagtcacc      60
atcaattgcc aggccagtga gagcattagt agcttcttat cctggtatca gcagaaacca     120
gggcagcgtc ccaggctcct gatctttttct gcatccactc tggcatctgg ggtcccatcg    180
cggttcaaag gcagtggatc tgggacagag ttcactctca ccatcagcgg cgtggagtgt    240
gccgatgctg ccacttatta ttgtcaacag ggttatagta aaagtaatgt ggataatgct    300
ttcggcggag ggaccgaggt ggtggtcaaa                                      330
```

<210> SEQ ID NO 19
<211> LENGTH: 217
<212> TYPE: PRT
<213> ORGANISM: Artificial Sequence
<220> FEATURE:
<223> OTHER INFORMATION: synthesized

<400> SEQUENCE: 19

Ala Tyr Asp Met Thr Gln Thr Pro Ala Ser Val Ser Ala Ala Val Gly
1               5                   10                  15

Gly Thr Val Thr Ile Asn Cys Gln Ala Ser Glu Ser Ile Ser Ser Phe
            20                  25                  30

Leu Ser Trp Tyr Gln Gln Lys Pro Gly Gln Arg Pro Arg Leu Leu Ile
        35                  40                  45

Phe Ser Ala Ser Thr Leu Ala Ser Gly Val Pro Ser Arg Phe Lys Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Gly Tyr Ser Lys Ser Asn
                85                  90                  95

Val Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
210                 215

<210> SEQ ID NO 20
<211> LENGTH: 110
<212> TYPE: PRT
<213> ORGANISM: Artificial Sequence
<220> FEATURE:
<223> OTHER INFORMATION: synthesized

<400> SEQUENCE: 20

Ala Tyr Asp Met Thr Gln Thr Pro Ala Ser Val Ser Ala Ala Val Gly
1               5                   10                  15

Gly Thr Val Thr Ile Asn Cys Gln Ala Ser Glu Ser Ile Ser Ser Phe
            20                  25                  30

Leu Ser Trp Tyr Gln Gln Lys Pro Gly Gln Arg Pro Arg Leu Leu Ile
        35                  40                  45

Phe Ser Ala Ser Thr Leu Ala Ser Gly Val Pro Ser Arg Phe Lys Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Gly Tyr Ser Lys Ser Asn
                85                  90                  95

Val Asp Asn Ala Phe Gly Gly Gly Thr Glu Val Val Val Lys
            100                 105                 110

<210> SEQ ID NO 21
<211> LENGTH: 1329

<212> TYPE: DNA
<213> ORGANISM: Artificial Sequence
<220> FEATURE:
<223> OTHER INFORMATION: synthesized

<400> SEQUENCE: 21

```
cagtcgctgg aggagtccgg gggtcgcctg gtcacgcctg ggacacccct gacactcacc      60
tgtacaactt ccggaatcga ccttagtacc tacgacatga tctgggtccg ccaggctcca     120
gggaaggggc tggaatacat cggaatcatt agttatgttg gtaacacata ctacgcgagc     180
tgggcgaaag gccgattcac cctctccaaa acctcgacca cggtggatct gagaatcacc     240
agtccgacaa ccgaggacac ggccacctat ttctgtgcca gggattttat tagtggttcc     300
cacttgtggg gcccgggcac cctggtcacc gtctcgagcg ctagcaccaa gggcccatcg     360
gtcttccccc tggcaccctc ctccaagagc acctctgggg gcacagcggc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acccagacct acatctgcaa cgtgaatcac     600
aagcccagca acaccaaggt ggacaagaga gttgagccca aatcttgtga caaaactcac     660
acatgcccac cgtgcccagc acctgaactc ctggggggac cgtcagtctt cctcttcccc     720
ccaaaaccca aggacaccct catgatctcc cggacccctg aggtcacatg cgtggtggtg     780
gacgtgagcc acgaagaccc tgaggtcaag ttcaactggt acgtggacgg cgtggaggtg     840
cataatgcca agacaaagcc gcgggaggag cagtacaaca gcacgtaccg tgtggtcagc     900
gtcctcaccg tcctgcacca ggactggctg aatggcaagg agtacaagtg caaggtctcc     960
aacaaagccc tcccagcccc catcgagaaa accatctcca aagccaaagg gcagccccga    1020
gaaccacagg tgtacaccct gcccccatcc cgggaggaga tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctata gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaa                                                            1329
```

<210> SEQ ID NO 22
<211> LENGTH: 339
<212> TYPE: DNA
<213> ORGANISM: Artificial Sequence
<220> FEATURE:
<223> OTHER INFORMATION: synthesized

<400> SEQUENCE: 22

```
cagtcgctgg aggagtccgg gggtcgcctg gtcacgcctg ggacacccct gacactcacc      60
tgtacaactt ccggaatcga ccttagtacc tacgacatga tctgggtccg ccaggctcca     120
gggaaggggc tggaatacat cggaatcatt agttatgttg gtaacacata ctacgcgagc     180
tgggcgaaag gccgattcac cctctccaaa acctcgacca cggtggatct gagaatcacc     240
agtccgacaa ccgaggacac ggccacctat ttctgtgcca gggattttat tagtggttcc     300
cacttgtggg gcccgggcac cctggtcacc gtctcgagc                             339
```

<210> SEQ ID NO 23
<211> LENGTH: 443
<212> TYPE: PRT

<213> ORGANISM: Artificial Sequence
<220> FEATURE:
<223> OTHER INFORMATION: synthesized

<400> SEQUENCE: 23

```
Gln Ser Leu Glu Glu Ser Gly Gly Arg Leu Val Thr Pro Gly Thr Pro
1               5                   10                  15
Leu Thr Leu Thr Cys Thr Thr Ser Gly Ile Asp Leu Ser Thr Tyr Asp
            20                  25                  30
Met Ile Trp Val Arg Gln Ala Pro Gly Lys Gly Leu Glu Tyr Ile Gly
        35                  40                  45
Ile Ile Ser Tyr Val Gly Asn Thr Tyr Tyr Ala Ser Trp Ala Lys Gly
50                  55                  60
Arg Phe Thr Leu Ser Lys Thr Ser Thr Val Asp Leu Arg Ile Thr
65                  70                  75                  80
Ser Pro Thr Thr Glu Asp Thr Ala Thr Tyr Phe Cys Ala Arg Asp Phe
                85                  90                  95
Ile Ser Gly Ser His Leu Trp Gly Pro Gly Thr Leu Val Thr Val Ser
            100                 105                 110
Ser Ala Ser Thr Lys Gly Pro Ser Val Phe Pro Leu Ala Pro Ser Ser
        115                 120                 125
Lys Ser Thr Ser Gly Gly Thr Ala Ala Leu Gly Cys Leu Val Lys Asp
130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
        195                 200                 205
Lys Arg Val Glu Pro Lys Ser Cys Asp Lys Thr His Thr Cys Pro Pro
210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Val Leu Asp Ser Asp Gly Ser Phe
```

```
                    385                 390                 395                 400
Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 24
<211> LENGTH: 113
<212> TYPE: PRT
<213> ORGANISM: Artificial Sequence
<220> FEATURE:
<223> OTHER INFORMATION: synthesized

<400> SEQUENCE: 24

Gln Ser Leu Glu Glu Ser Gly Gly Arg Leu Val Thr Pro Gly Thr Pro
1               5                   10                  15

Leu Thr Leu Thr Cys Thr Thr Ser Gly Ile Asp Leu Ser Thr Tyr Asp
                20                  25                  30

Met Ile Trp Val Arg Gln Ala Pro Gly Lys Gly Leu Glu Tyr Ile Gly
            35                  40                  45

Ile Ile Ser Tyr Val Gly Asn Thr Tyr Tyr Ala Ser Trp Ala Lys Gly
        50                  55                  60

Arg Phe Thr Leu Ser Lys Thr Ser Thr Thr Val Asp Leu Arg Ile Thr
65                  70                  75                  80

Ser Pro Thr Thr Glu Asp Thr Ala Thr Tyr Phe Cys Ala Arg Asp Phe
                85                  90                  95

Ile Ser Gly Ser His Leu Trp Gly Pro Gly Thr Leu Val Thr Val Ser
                100                 105                 110

Ser

<210> SEQ ID NO 25
<211> LENGTH: 651
<212> TYPE: DNA
<213> ORGANISM: Artificial Sequence
<220> FEATURE:
<223> OTHER INFORMATION: synthesized

<400> SEQUENCE: 25
gcctatgata tgacccagtc tccatcttcc gtgtctgcat ctgtaggaga cagagtcacc      60
atcaattgtc aggccagtga gagcattagt agcttcttat cctggtatca gcagaaacca    120
gggaaagccc ctaagctcct gatctttttct gcatccactc tggcatctgg ggtcccatca   180
aggttcagcg gcagtggatc tgggacagat ttcactctca ccatcagcag cctgcagcct    240
gaagattttg caacttacta ttgtcaacag ggttatagta aaagtaatgt ggataatgct    300
ttcggcggag ggaccaaggt ggagatcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651

<210> SEQ ID NO 26
<211> LENGTH: 330
```

<212> TYPE: DNA
<213> ORGANISM: Artificial Sequence
<220> FEATURE:
<223> OTHER INFORMATION: synthesized

<400> SEQUENCE: 26

```
gcctatgata tgacccagtc tccatcttcc gtgtctgcat ctgtaggaga cagagtcacc    60
atcaattgtc aggccagtga gagcattagt agcttcttat cctggtatca gcagaaacca   120
gggaaagccc ctaagctcct gatctttct gcatccactc tggcatctgg ggtcccatca   180
aggttcagcg gcagtggatc tgggacagat ttcactctca ccatcagcag cctgcagcct   240
gaagattttg caacttacta ttgtcaacag ggttatagta aaagtaatgt ggataatgct   300
ttcggcggag ggaccaaggt ggagatcaaa                                    330
```

<210> SEQ ID NO 27
<211> LENGTH: 217
<212> TYPE: PRT
<213> ORGANISM: Artificial Sequence
<220> FEATURE:
<223> OTHER INFORMATION: synthesized

<400> SEQUENCE: 27

```
Ala Tyr Asp Met Thr Gln Ser Pro Ser Ser Val Ser Ala Ser Val Gly
 1               5                  10                  15

Asp Arg Val Thr Ile Asn Cys Gln Ala Ser Glu Ser Ile Ser Ser Phe
            20                  25                  30

Leu Ser Trp Tyr Gln Gln Lys Pro Gly Lys Ala Pro Lys Leu Leu Ile
        35                  40                  45

Phe Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Lys Ser Asn
                85                  90                  95

Val Asp Asn Ala Phe Gly Gly Gly Thr Lys Val Glu Ile Lys Arg Thr
           100                 105                 110

Val Ala Ala Pro Ser Val Phe Ile Phe Pro Pro Ser Asp Glu Gln Leu
       115                 120                 125

Lys Ser Gly Thr Ala Ser Val Val Cys Leu Leu Asn Asn Phe Tyr Pro
   130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 28
<211> LENGTH: 110
<212> TYPE: PRT
<213> ORGANISM: Artificial Sequence
<220> FEATURE:
<223> OTHER INFORMATION: synthesized

<400> SEQUENCE: 28

Ala Tyr Asp Met Thr Gln Ser Pro Ser Ser Val Ser Ala Ser Val Gly
1               5                   10                  15

Asp Arg Val Thr Ile Asn Cys Gln Ala Ser Glu Ser Ile Ser Ser Phe
            20                  25                  30

Leu Ser Trp Tyr Gln Gln Lys Pro Gly Lys Ala Pro Lys Leu Leu Ile
        35                  40                  45

Phe Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Lys Ser Asn
                85                  90                  95

Val Asp Asn Ala Phe Gly Gly Gly Thr Lys Val Glu Ile Lys
            100                 105                 110

<210> SEQ ID NO 29
<211> LENGTH: 1329
<212> TYPE: DNA
<213> ORGANISM: Artificial Sequence
<220> FEATURE:
<223> OTHER INFORMATION: synthesized

<400> SEQUENCE: 29

| | |
|---|---|
| caggtgcagc tggtggagtc tgggggaggc ctggtccagc ctgggggctc cctgagactc | 60 |
| tcctgtacaa cttctggaat cgaccttagt acctacgaca tgatctgggt ccgccaggct | 120 |
| ccaggcaagg ggctagagtg ggtgggaatc attagttatg ttggtaacac atactacgcg | 180 |
| agctgggcga aaggccgatt caccctctcc aaaaccaaga acacggtgta tctgcaaatg | 240 |
| aacagcctga gagctgagga cacggctgtg tattactgtg cgagagattt tattagtggt | 300 |
| tcccacttgt ggggccaggg aaccctggtc accgtctcga gcgctagcac caagggccca | 360 |
| tcggtcttcc ccctggcacc ctcctccaag agcacctctg ggggcacagc ggccctgggc | 420 |
| tgcctggtca aggactactt ccccgaaccg gtgacggtgt cgtggaactc aggcgccctg | 480 |
| accagcggcg tgcacacctt cccggctgtc ctacagtcct caggactcta ctccctcagc | 540 |
| agcgtggtga ccgtgccctc agcagcttg gcacccaga cctacatctg caacgtgaat | 600 |
| cacaagccca gcaacaccaa ggtggacaag agagttgagc ccaaatcttg tgacaaaact | 660 |
| cacacatgcc caccgtgccc agcacctgaa gccgcggggg gaccgtcagt cttcctcttc | 720 |
| cccccaaaac ccaaggacac cctcatgatc tcccggaccc ctgaggtcac atgcgtggtg | 780 |
| gtggacgtga gccacgaaga ccctgaggtc aagttcaact ggtacgtgga cggcgtggag | 840 |
| gtgcataatg ccaagacaaa gccgcgggag gagcagtaca acagcacgta ccgtgtggtc | 900 |
| agcgtcctca ccgtcctgca ccaggactgg ctgaatggca aggagtacaa gtgcgcggtc | 960 |
| tccaacaaag cccteccagc ccccatcgag aaaaccatct ccaaagccaa agggcagccc | 1020 |
| cgagaaccac aggtgtacac cctgccccca tcccgggatg agctgaccaa gaaccaggtc | 1080 |
| agcctgacct gcctggtcaa aggcttctat cccagcgaca tcgccgtgga gtgggagagc | 1140 |
| aatgggcagc cggagaacaa ctacaagacc acgcctcccg tgctggactc cgacggctcc | 1200 |
| ttcttcctct atagcaagct caccgtggac aagagcaggt ggcagcaggg gaacgtcttc | 1260 |
| tcatgctccg tgatgcatga ggctctgcac aaccactaca cgcagaagag cctctccctg | 1320 |
| tctccgggt | 1329 |

<210> SEQ ID NO 30
<211> LENGTH: 342
<212> TYPE: DNA
<213> ORGANISM: Artificial Sequence
<220> FEATURE:
<223> OTHER INFORMATION: synthesized

<400> SEQUENCE: 30

```
caggtgcagc tggtggagtc tgggggaggc ctggtccagc ctgggggctc cctgagactc      60
tcctgtacaa cttctggaat cgaccttagt acctacgaca tgatctgggt ccgccaggct     120
ccaggcaagg ggctagagtg ggtgggaatc attagttatg ttggtaacac atactacgcg     180
agctgggcga aaggccgatt caccctctcc aaaaccaaga acacggtgta tctgcaaatg     240
aacagcctga gagctgagga cacggctgtg tattactgtg cgagagattt tattagtggt     300
tcccacttgt ggggccaggg aaccctggtc accgtctcga gc                        342
```

<210> SEQ ID NO 31
<211> LENGTH: 443
<212> TYPE: PRT
<213> ORGANISM: Artificial Sequence
<220> FEATURE:
<223> OTHER INFORMATION: synthesized

<400> SEQUENCE: 31

```
Gln Val Gln Leu Val Glu Ser Gly Gly Gly Leu Val Gln Pro Gly Gly
1               5                   10                  15

Ser Leu Arg Leu Ser Cys Thr Thr Ser Gly Ile Asp Leu Ser Thr Tyr
            20                  25                  30

Asp Met Ile Trp Val Arg Gln Ala Pro Gly Lys Gly Leu Glu Trp Val
        35                  40                  45

Gly Ile Ile Ser Tyr Val Gly Asn Thr Tyr Tyr Ala Ser Trp Ala Lys
    50                  55                  60

Gly Arg Phe Thr Leu Ser Lys Thr Lys Asn Thr Val Tyr Leu Gln Met
65                  70                  75                  80

Asn Ser Leu Arg Ala Glu Asp Thr Ala Val Tyr Tyr Cys Ala Arg Asp
                85                  90                  95

Phe Ile Ser Gly Ser His Leu Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Ala Ala Gly Ala Pro Ser Val Phe Leu Phe
225                 230                 235                 240

Pro Pro Lys Pro Lys Asp Thr Leu Met Ile Ser Arg Thr Pro Glu Val
                245                 250                 255
```

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Ala Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 32
<211> LENGTH: 114
<212> TYPE: PRT
<213> ORGANISM: Artificial Sequence
<220> FEATURE:
<223> OTHER INFORMATION: synthesized

<400> SEQUENCE: 32

Gln Val Gln Leu Val Glu Ser Gly Gly Gly Leu Val Gln Pro Gly Gly
1               5                   10                  15

Ser Leu Arg Leu Ser Cys Thr Thr Ser Gly Ile Asp Leu Ser Thr Tyr
            20                  25                  30

Asp Met Ile Trp Val Arg Gln Ala Pro Gly Lys Gly Leu Glu Trp Val
        35                  40                  45

Gly Ile Ile Ser Tyr Val Gly Asn Thr Tyr Tyr Ala Ser Trp Ala Lys
    50                  55                  60

Gly Arg Phe Thr Leu Ser Lys Thr Lys Asn Thr Val Tyr Leu Gln Met
65                  70                  75                  80

Asn Ser Leu Arg Ala Glu Asp Thr Ala Val Tyr Tyr Cys Ala Arg Asp
                85                  90                  95

Phe Ile Ser Gly Ser His Leu Trp Gly Gln Gly Thr Leu Val Thr Val
            100                 105                 110

Ser Ser

<210> SEQ ID NO 33
<211> LENGTH: 651
<212> TYPE: DNA
<213> ORGANISM: Artificial Sequence
<220> FEATURE:
<223> OTHER INFORMATION: synthesized

<400> SEQUENCE: 33

```
gccgtgctga cccagactcc atctcccgtg tctgcagctg tgggaggcac agtcagcatc    60
agttgccagt ccagtcagag tgtttataat ggctactggt tatcctggta tcagcagaag   120
ccagggcagc ctcccaagct cctgatctat ggtgcatcca ctctggcatc tggggtccca   180
tcgcggttca aaggcagtgg atctgggaca cagttcactc tcaccatcaa cgacgtgcag   240
tgtgacgatg ctgccactta ctactgtcta ggcagttata ctagtagtac tgagaattct   300
ttcggcggag ggaccgaggt ggtggtcaaa cgtacggtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaag tctacgcctg cgaagtcacc   600
catcagggcc tgagctcgcc cgtcacaaag agcttcaaca ggggagagtg t            651
```

<210> SEQ ID NO 34
<211> LENGTH: 330
<212> TYPE: DNA
<213> ORGANISM: Artificial Sequence
<220> FEATURE:
<223> OTHER INFORMATION: synthesized

<400> SEQUENCE: 34

```
gccgtgctga cccagactcc atctcccgtg tctgcagctg tgggaggcac agtcagcatc    60
agttgccagt ccagtcagag tgtttataat ggctactggt tatcctggta tcagcagaag   120
ccagggcagc ctcccaagct cctgatctat ggtgcatcca ctctggcatc tggggtccca   180
tcgcggttca aaggcagtgg atctgggaca cagttcactc tcaccatcaa cgacgtgcag   240
tgtgacgatg ctgccactta ctactgtcta ggcagttata ctagtagtac tgagaattct   300
ttcggcggag ggaccgaggt ggtggtcaaa                                    330
```

<210> SEQ ID NO 35
<211> LENGTH: 217
<212> TYPE: PRT
<213> ORGANISM: Artificial Sequence
<220> FEATURE:
<223> OTHER INFORMATION: synthesized

<400> SEQUENCE: 35

```
Ala Val Leu Thr Gln Thr Pro Ser Pro Val Ser Ala Ala Val Gly Gly
1               5                   10                  15

Thr Val Ser Ile Ser Cys Gln Ser Ser Gln Ser Val Tyr Asn Gly Tyr
            20                  25                  30

Trp Leu Ser Trp Tyr Gln Gln Lys Pro Gly Gln Pro Pro Lys Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Thr Gln Phe Thr Leu Thr Ile Asn Asp Val Gln
65                  70                  75                  80

Cys Asp Asp Ala Ala Thr Tyr Tyr Cys Leu Gly Ser Tyr Thr Ser Ser
                85                  90                  95

Thr Glu Asn Ser Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125
```

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 36
<211> LENGTH: 110
<212> TYPE: PRT
<213> ORGANISM: Artificial Sequence
<220> FEATURE:
<223> OTHER INFORMATION: synthesized

<400> SEQUENCE: 36

Ala Val Leu Thr Gln Thr Pro Ser Pro Val Ser Ala Ala Val Gly Gly
1               5                   10                  15

Thr Val Ser Ile Ser Cys Gln Ser Ser Gln Ser Val Tyr Asn Gly Tyr
            20                  25                  30

Trp Leu Ser Trp Tyr Gln Gln Lys Pro Gly Gln Pro Pro Lys Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Thr Gln Phe Thr Leu Thr Ile Asn Asp Val Gln
65                  70                  75                  80

Cys Asp Asp Ala Ala Thr Tyr Tyr Cys Leu Gly Ser Tyr Thr Ser Ser
                85                  90                  95

Thr Glu Asn Ser Phe Gly Gly Gly Thr Glu Val Val Val Lys
            100                 105                 110

<210> SEQ ID NO 37
<211> LENGTH: 1341
<212> TYPE: DNA
<213> ORGANISM: Artificial Sequence
<220> FEATURE:
<223> OTHER INFORMATION: synthesized

<400> SEQUENCE: 37
caggagcagc tggaggagtc cggggggaggc ctggtcacgc ctggaggaac cctgacactc      60
acctgcacag tctctggatt ctccctcagt agctactgga tgagctgggt ccgccaggct     120
ccagggaagg ggctggagtg gatcggagtc attgatacta atgtttatat atactacgcg     180
aactgggcaa aggccgatt caccatctcc aaaaacctcg accacgtgga tctgaagatc     240
accagtccga caaccgagga cacggccacc tatttctgtg ccagatatgt gggtaataat     300
gatgattata ttaacttgtg gggcccgggc accctggtca ccgtctcgag cgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600

-continued

```
aacgtgaatc acaagcccag caacaccaag gtggacaaga gagttgagcc caaatcttgt      660
gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga tgaccaag      1080 aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta tagcaagctc accgtggaca agagcaggtg gcagcagggg     1260
aacgtcttct catgctccgt gatgcatgag gctctgcaca accactacac gcagaagagc     1320
ctctccctgt ctccgggtaa a                                                1341
```

<210> SEQ ID NO 38
<211> LENGTH: 351
<212> TYPE: DNA
<213> ORGANISM: Artificial Sequence
<220> FEATURE:
<223> OTHER INFORMATION: synthesized

<400> SEQUENCE: 38

```
caggagcagc tggaggagtc cggggggaggc ctggtcacgc ctggaggaac cctgacactc       60
acctgcacag tctctggatt ctccctcagt agctactgga tgagctgggt ccgccaggct      120
ccagggaagg ggctggagtg gatcggagtc attgatacta atgtttatat atactacgcg      180
aactgggcaa aaggccgatt caccatctcc aaaacctcga ccacggtgga tctgaagatc      240
accagtccga caaccgagga cacggccacc tatttctgtg ccagatatgt gggtaataat      300
gatgattata ttaacttgtg gggcccgggc accctggtca ccgtctcgag c              351
```

<210> SEQ ID NO 39
<211> LENGTH: 447
<212> TYPE: PRT
<213> ORGANISM: Artificial Sequence
<220> FEATURE:
<223> OTHER INFORMATION: synthesized

<400> SEQUENCE: 39

```
Gln Glu Gln Leu Glu Glu Ser Gly Gly Gly Leu Val Thr Pro Gly Gly
1               5                   10                  15

Thr Leu Thr Leu Thr Cys Thr Val Ser Gly Phe Ser Leu Ser Ser Tyr
            20                  25                  30

Trp Met Ser Trp Val Arg Gln Ala Pro Gly Lys Gly Leu Glu Trp Ile
        35                  40                  45

Gly Val Ile Asp Thr Asn Val Tyr Ile Tyr Tyr Ala Asn Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Tyr
                85                  90                  95

Val Gly Asn Asn Asp Asp Tyr Ile Asn Leu Trp Gly Pro Gly Thr Leu
            100                 105                 110
```

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 40
<211> LENGTH: 117
<212> TYPE: PRT
<213> ORGANISM: Artificial Sequence
<220> FEATURE:
<223> OTHER INFORMATION: synthesized

<400> SEQUENCE: 40

Gln Glu Gln Leu Glu Glu Ser Gly Gly Gly Leu Val Thr Pro Gly Gly
1               5                   10                  15

Thr Leu Thr Leu Thr Cys Thr Val Ser Gly Phe Ser Leu Ser Ser Tyr
            20                  25                  30

Trp Met Ser Trp Val Arg Gln Ala Pro Gly Lys Gly Leu Glu Trp Ile
            35                  40                  45

Gly Val Ile Asp Thr Asn Val Tyr Ile Tyr Tyr Ala Asn Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Tyr
                85                  90                  95

Val Gly Asn Asn Asp Asp Tyr Ile Asn Leu Trp Gly Pro Gly Thr Leu
            100                 105                 110

Val Thr Val Ser Ser
        115

<210> SEQ ID NO 41
<211> LENGTH: 654
<212> TYPE: DNA
<213> ORGANISM: Artificial Sequence
<220> FEATURE:
<223> OTHER INFORMATION: synthesized

<400> SEQUENCE: 41
gacatccaga tgacccagtc tccttccacc ctgtctgcat ctgtaggaga cagagtcacc    60
atcacttgcc agtccagtca gagtgtttat aatggctact ggttatcctg gtatcagcag   120
aaaccaggga agcccctaa gctcctgatc tatggtgcat ccactctggc atctggggtc    180
ccatcaaggt tcagcggcag tggatctggg acagaattca ctctcaccat cagcagcctg   240
cagcctgatg attttgcaac ttattactgc ctaggcagtt atactagtag tactgagaac   300
tctttcggcg agggaccaa ggtggagatc aaacgtacgg tggctgcacc atctgtcttc    360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600 acccatcagg gcctgagctc gcccgtcaca aagagcttca caggggaga gtgt          654

<210> SEQ ID NO 42
<211> LENGTH: 333
<212> TYPE: DNA
<213> ORGANISM: Artificial Sequence
<220> FEATURE:
<223> OTHER INFORMATION: synthesized

<400> SEQUENCE: 42
gacatccaga tgacccagtc tccttccacc ctgtctgcat ctgtaggaga cagagtcacc    60
atcacttgcc agtccagtca gagtgtttat aatggctact ggttatcctg gtatcagcag   120
aaaccaggga agcccctaa gctcctgatc tatggtgcat ccactctggc atctggggtc    180
ccatcaaggt tcagcggcag tggatctggg acagaattca ctctcaccat cagcagcctg   240
cagcctgatg attttgcaac ttattactgc ctaggcagtt atactagtag tactgagaac   300
tctttcggcg agggaccaa ggtggagatc aaa                                 333

<210> SEQ ID NO 43
<211> LENGTH: 218
<212> TYPE: PRT
<213> ORGANISM: Artificial Sequence
<220> FEATURE:
<223> OTHER INFORMATION: synthesized -continued

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Asn Gly
            20                  25                  30

Tyr Trp Leu Ser Trp Tyr Gln Gln Lys Pro Gly Lys Ala Pro Lys Leu
        35                  40                  45

Leu Ile Tyr Gly Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Leu Gly Ser Tyr Thr Ser
                85                  90                  95

Ser Thr Glu Asn Ser Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 44
<211> LENGTH: 111
<212> TYPE: PRT
<213> ORGANISM: Artificial Sequence
<220> FEATURE:
<223> OTHER INFORMATION: synthesized

<400> SEQUENCE: 44

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Asn Gly
            20                  25                  30

Tyr Trp Leu Ser Trp Tyr Gln Gln Lys Pro Gly Lys Ala Pro Lys Leu
        35                  40                  45

Leu Ile Tyr Gly Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Leu Gly Ser Tyr Thr Ser
                85                  90                  95

Ser Thr Glu Asn Ser Phe Gly Gly Gly Thr Lys Val Glu Ile Lys
            100                 105                 110

<210> SEQ ID NO 45
<211> LENGTH: 1347

<212> TYPE: DNA
<213> ORGANISM: Artificial Sequence
<220> FEATURE:
<223> OTHER INFORMATION: synthesized

<400> SEQUENCE: 45

```
gaggtgcagc tggtggagtc tgggggaggc ttggtccagc ctgggggtc cctgagactc      60
tcctgtgcag cctctggatt ctccctcagt agctactgga tgagctgggt ccgccaggct    120
ccagggaagg ggctggagtg gatcggagtc attgatacta atgtttatat atactacgcg    180
aactgggcaa aaggcagatt caccatctcc agagacaatt ccaagaacac gctgtatctt    240
caaatgaaca gcctgagagc cgaggacacg gctgtgtatt actgtgcgag atatgtgggt    300
aataatgatg attatattaa cttgtggggc cagggaaccc tggtcaccgt ctcgagcgct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaactcct ggggggaccg    720
tcagtcttcc tcttccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 46
<211> LENGTH: 357
<212> TYPE: DNA
<213> ORGANISM: Artificial Sequence
<220> FEATURE:
<223> OTHER INFORMATION: synthesized

<400> SEQUENCE: 46

```
gaggtgcagc tggtggagtc tgggggaggc ttggtccagc ctgggggtc cctgagactc      60
tcctgtgcag cctctggatt ctccctcagt agctactgga tgagctgggt ccgccaggct    120
ccagggaagg ggctggagtg gatcggagtc attgatacta atgtttatat atactacgcg    180
aactgggcaa aaggcagatt caccatctcc agagacaatt ccaagaacac gctgtatctt    240
caaatgaaca gcctgagagc cgaggacacg gctgtgtatt actgtgcgag atatgtgggt    300
aataatgatg attatattaa cttgtggggc cagggaaccc tggtcaccgt ctcgagc      357
```

<210> SEQ ID NO 47
<211> LENGTH: 449
<212> TYPE: PRT

<213> ORGANISM: Artificial Sequence
<220> FEATURE:
<223> OTHER INFORMATION: synthesized

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Trp Met Ser Trp Val Arg Gln Ala Pro Gly Lys Gly Leu Glu Trp Ile
        35                  40                  45

Gly Val Ile Asp Thr Asn Val Tyr Ile Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Val Gly Asn Asn Asp Asp Tyr Ile Asn Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
                385             390             395             400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 48
<211> LENGTH: 119
<212> TYPE: PRT
<213> ORGANISM: Artificial Sequence
<220> FEATURE:
<223> OTHER INFORMATION: synthesized

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Trp Met Ser Trp Val Arg Gln Ala Pro Gly Lys Gly Leu Glu Trp Ile
        35                  40                  45

Gly Val Ile Asp Thr Asn Val Tyr Ile Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Val Gly Asn Asn Asp Asp Tyr Ile Asn Leu Trp Gly Gln Gly
            100                 105                 110

Thr Leu Val Thr Val Ser Ser
        115

<210> SEQ ID NO 49
<211> LENGTH: 648
<212> TYPE: DNA
<213> ORGANISM: Artificial Sequence
<220> FEATURE:
<223> OTHER INFORMATION: synthesized

<400> SEQUENCE: 49
gcattcgaat tgacccagac tccagcctcc gtgtctgaac ctgtgggagg cacagtcacc      60
atcaagtgcc aggccagtga aagcattagc aactactat cctggtatca gcagattcca     120
gggcagcctc ccaacctcct gatctattat gcatccaatc tggcatctgg ggtcccatcg     180
cggttcaaag gcagtggatc tgggacagag ttcactctca ccatcagcga cctggagtgt     240
gccgatgctg ccacttacta ctgtcaaagc tattatggtg gtggtagtgc ctatactttc     300
ggcggaggga ccgaggtggt ggtcaaacgt acggtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata cgccctcca atcgggtaac     480 tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt               648
```

<210> SEQ ID NO 50
<211> LENGTH: 327
<212> TYPE: DNA
<213> ORGANISM: Artificial Sequence
<220> FEATURE:
<223> OTHER INFORMATION: synthesized

<400> SEQUENCE: 50

```
gcattcgaat tgacccagac tccagcctcc gtgtctgaac ctgtgggagg cacagtcacc        60
atcaagtgcc aggccagtga agcattagc aactacttat cctggtatca gcagattcca       120
gggcagcctc ccaacctcct gatctattat gcatccaatc tggcatctgg ggtcccatcg       180
cggttcaaag gcagtggatc tgggacagag ttcactctca ccatcagcga cctggagtgt       240
gccgatgctg ccacttacta ctgtcaaagc tattatggtg gtggtagtgc ctatactttc       300
ggcggaggga ccgaggtggt ggtcaaa                                           327
```

<210> SEQ ID NO 51
<211> LENGTH: 216
<212> TYPE: PRT
<213> ORGANISM: Artificial Sequence
<220> FEATURE:
<223> OTHER INFORMATION: synthesized

<400> SEQUENCE: 51

```
Ala Phe Glu Leu Thr Gln Thr Pro Ala Ser Val Ser Glu Pro Val Gly
1               5                   10                  15

Gly Thr Val Thr Ile Lys Cys Gln Ala Ser Glu Ser Ile Ser Asn Tyr
            20                  25                  30

Leu Ser Trp Tyr Gln Gln Ile Pro Gly Gln Pro Pro Asn Leu Leu Ile
        35                  40                  45

Tyr Tyr Ala Ser Asn Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Gly Gly Gly Ser
                85                  90                  95

Ala Tyr Thr Phe Gly Gly Gly Thr Glu Val Val Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 52
<211> LENGTH: 109
<212> TYPE: PRT
<213> ORGANISM: Artificial Sequence
<220> FEATURE:
<223> OTHER INFORMATION: synthesized

<400> SEQUENCE: 52

Ala Phe Glu Leu Thr Gln Thr Pro Ala Ser Val Ser Glu Pro Val Gly
1               5                   10                  15

Gly Thr Val Thr Ile Lys Cys Gln Ala Ser Glu Ser Ile Ser Asn Tyr
            20                  25                  30

Leu Ser Trp Tyr Gln Gln Ile Pro Gly Gln Pro Pro Asn Leu Leu Ile
        35                  40                  45

Tyr Tyr Ala Ser Asn Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Gly Gly Gly Ser
                85                  90                  95

Ala Tyr Thr Phe Gly Gly Gly Thr Glu Val Val Val Lys
                100                 105

<210> SEQ ID NO 53
<211> LENGTH: 1341
<212> TYPE: DNA
<213> ORGANISM: Artificial Sequence
<220> FEATURE:
<223> OTHER INFORMATION: synthesized

<400> SEQUENCE: 53
cagtcggtgg aggagtccgg gggtcgcctg gtcacgcctg gacacccct gacactcacc      60
tgcacagtgt ctggaatcga cctcagtgtc atcaatatgg gctgggtccg ccaggctcca    120
ggggaggggc tggaatggat cggaaccatt acttatgttg gtaacacata ttacgcgagc    180
tgggcgaaag ccgattcac catctccaaa acctcgacca cggtggatct gaaaatcacc     240
agtccgacaa ccgaggacac ggccacttat ttctgtgcca gagaatctgg tactattat     300
tacagttact ttaacttgtg gggccaaggc accctggtca ccgtctcgag cgctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaccatctc caaagccaaa    1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta tagcaagctc accgtggaca gagcaggtg gcagcagggg   1260
aacgtcttct catgctccgt gatgcatgag gctctgcaca accactacac gcagaagagc   1320
ctctccctgt ctccgggtaa a                                              1341

<210> SEQ ID NO 54
<211> LENGTH: 351
<212> TYPE: DNA
<213> ORGANISM: Artificial Sequence
<220> FEATURE:
<223> OTHER INFORMATION: synthesized

<400> SEQUENCE: 54
cagtcggtgg aggagtccgg gggtcgcctg gtcacgcctg gacacccct gacactcacc      60
tgcacagtgt ctggaatcga cctcagtgtc atcaatatgg gctgggtccg ccaggctcca    120
ggggaggggc tggaatggat cggaaccatt acttatgttg gtaacacata ttacgcgagc    180
tgggcgaaag gccgattcac catctccaaa acctcgacca cggtggatct gaaaatcacc    240
agtccgacaa ccgaggacac ggccacttat ttctgtgcca gagaatctgg tactatttat    300
tacagttact ttaacttgtg gggccaaggc accctggtca ccgtctcgag c             351

<210> SEQ ID NO 55
<211> LENGTH: 447
<212> TYPE: PRT
<213> ORGANISM: Artificial Sequence
<220> FEATURE:
<223> OTHER INFORMATION: synthesized

<400> SEQUENCE: 55

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Val Ile Asn
            20                  25                  30

Met Gly Trp Val Arg Gln Ala Pro Gly Glu Gly Leu Glu Trp Ile Gly
        35                  40                  45

Thr Ile Thr Tyr Val Gly Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Ser
                85                  90                  95

Gly Thr Ile Tyr Tyr Ser Tyr Phe Asn Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

```
Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 56
<211> LENGTH: 117
<212> TYPE: PRT
<213> ORGANISM: Artificial Sequence
<220> FEATURE:
<223> OTHER INFORMATION: synthesized

<400> SEQUENCE: 56

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Val Ile Asn
            20                  25                  30

Met Gly Trp Val Arg Gln Ala Pro Gly Glu Gly Leu Glu Trp Ile Gly
        35                  40                  45

Thr Ile Thr Tyr Val Gly Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Ser
                85                  90                  95

Gly Thr Ile Tyr Tyr Ser Tyr Phe Asn Leu Trp Gly Gln Gly Thr Leu
            100                 105                 110

Val Thr Val Ser Ser
        115

<210> SEQ ID NO 57
<211> LENGTH: 648
<212> TYPE: DNA
<213> ORGANISM: Artificial Sequence
```

<220> FEATURE:
<223> OTHER INFORMATION: synthesized

<400> SEQUENCE: 57

```
gcattcgaat tgacccagtc tccatcctcc ctgtctgcat ctgtaggaga cagagtcacc      60
atcaagtgcc aggccagtga aagcattagc aactacttat cctggtatca gcagattcca     120
gggaaagttc ctaagctcct gatctattat gcatccaatc tggcatctgg ggtcccatct     180
cggttcagtg gcagtggatc tgggacagat ttcactctca ccatcagcag cctgcagcct     240
gaagatgttg caacttatta ctgtcaaagc tattatggtg gtggtagtgc ctatactttc     300
ggcggaggga ccaaggtgga gatcaaacgt acggtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                  648
```

<210> SEQ ID NO 58
<211> LENGTH: 327
<212> TYPE: DNA
<213> ORGANISM: Artificial Sequence
<220> FEATURE:
<223> OTHER INFORMATION: synthesized

<400> SEQUENCE: 58

```
gcattcgaat tgacccagtc tccatcctcc ctgtctgcat ctgtaggaga cagagtcacc      60
atcaagtgcc aggccagtga aagcattagc aactacttat cctggtatca gcagattcca     120
gggaaagttc ctaagctcct gatctattat gcatccaatc tggcatctgg ggtcccatct     180
cggttcagtg gcagtggatc tgggacagat ttcactctca ccatcagcag cctgcagcct     240
gaagatgttg caacttatta ctgtcaaagc tattatggtg gtggtagtgc ctatactttc     300
ggcggaggga ccaaggtgga gatcaaa                                         327
```

<210> SEQ ID NO 59
<211> LENGTH: 216
<212> TYPE: PRT
<213> ORGANISM: Artificial Sequence
<220> FEATURE:
<223> OTHER INFORMATION: synthesized

<400> SEQUENCE: 59

```
Ala Phe Glu Leu Thr Gln Ser Pro Ser Ser Leu Ser Ala Ser Val Gly
1               5                   10                  15
Asp Arg Val Thr Ile Lys Cys Gln Ala Ser Glu Ser Ile Ser Asn Tyr
            20                  25                  30
Leu Ser Trp Tyr Gln Gln Ile Pro Gly Lys Val Pro Lys Leu Leu Ile
        35                  40                  45
Tyr Tyr Ala Ser Asn Leu Ala Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Ser Tyr Tyr Gly Gly Gly Ser
                85                  90                  95
Ala Tyr Thr Phe Gly Gly Gly Thr Lys Val Glu Ile Lys Arg Thr Val
            100                 105                 110
```

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 60
<211> LENGTH: 109
<212> TYPE: PRT
<213> ORGANISM: Artificial Sequence
<220> FEATURE:
<223> OTHER INFORMATION: synthesized

<400> SEQUENCE: 60

Ala Phe Glu Leu Thr Gln Ser Pro Ser Ser Leu Ser Ala Ser Val Gly
1               5                   10                  15

Asp Arg Val Thr Ile Lys Cys Gln Ala Ser Glu Ser Ile Ser Asn Tyr
            20                  25                  30

Leu Ser Trp Tyr Gln Gln Ile Pro Gly Lys Val Pro Lys Leu Leu Ile
        35                  40                  45

Tyr Tyr Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Tyr Tyr Gly Gly Gly Ser
                85                  90                  95

Ala Tyr Thr Phe Gly Gly Gly Thr Lys Val Glu Ile Lys
            100                 105

<210> SEQ ID NO 61
<211> LENGTH: 1341
<212> TYPE: DNA
<213> ORGANISM: Artificial Sequence
<220> FEATURE:
<223> OTHER INFORMATION: synthesized

<400> SEQUENCE: 61
gaggtgcagc tggtggagtc tgggggaggc ttggtccagc ctggggggtc cctgagactc      60
tcctgtacag tgtctggaat cgacctcagt gtcatcaata tggctggggt ccgccaggct     120
ccagggaagg ggctggagtg gatcggaacc attacttatg ttggtaacac atattacgcg     180
agctgggcga aaggcagatt caccatctcc aaaacctcga ccacggtgga tcttaaaatc     240
accagtccga caaccgagga cacggctgtg tattactgtg cgagagaatc tggtactatt     300
tattacagtt actttaactt gtggggccaa gggaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480

```
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600 tgcaacgtga atcacaagcc cagcaacacc aaggtggaca agagagttga gcccaaatct    660
tgtgacaaaa ctcacacatg cccaccgtgc ccagcacctg aagccgcggg ggcaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcgcgg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341

<210> SEQ ID NO 62
<211> LENGTH: 354
<212> TYPE: DNA
<213> ORGANISM: Artificial Sequence
<220> FEATURE:
<223> OTHER INFORMATION: synthesized

<400> SEQUENCE: 62
gaggtgcagc tggtggagtc tgggggaggc ttggtccagc ctgggggtc cctgagactc     60 tcctgtacag tgtctggaat cgacctcagt gtcatcaata tgggctgggt ccgccaggct    120
ccagggaagg ggctggagtg gatcggaacc attacttatg ttggtaacac atattacgcg    180
agctgggcga aaggcagatt caccatctcc aaaacctcga ccacggtgga tcttaaaatc    240
accagtccga caaccgagga cacggctgtg tattactgtg cgagagaatc tggtactatt    300
tattacagtt actttaactt gtggggccaa gggaccctgg tcaccgtctc gagc          354

<210> SEQ ID NO 63
<211> LENGTH: 447
<212> TYPE: PRT
<213> ORGANISM: Artificial Sequence
<220> FEATURE:
<223> OTHER INFORMATION: synthesized

<400> SEQUENCE: 63

Glu Val Gln Leu Val Glu Ser Gly Gly Gly Leu Val Gln Pro Gly Gly
 1               5                  10                  15

Ser Leu Arg Leu Ser Cys Thr Val Ser Gly Ile Asp Leu Ser Val Ile
            20                  25                  30

Asn Met Gly Trp Val Arg Gln Ala Pro Gly Lys Gly Leu Glu Trp Ile
        35                  40                  45

Gly Thr Ile Thr Tyr Val Gly Asn Thr Tyr Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Val Tyr Tyr Cys Ala Arg Glu
                85                  90                  95
```

Ser Gly Thr Ile Tyr Tyr Ser Tyr Phe Asn Leu Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 64
<211> LENGTH: 118
<212> TYPE: PRT
<213> ORGANISM: Artificial Sequence
<220> FEATURE:
<223> OTHER INFORMATION: synthesized

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Thr Val Ser Gly Ile Asp Leu Ser Val Ile
            20                  25                  30

Asn Met Gly Trp Val Arg Gln Ala Pro Gly Lys Gly Leu Glu Trp Ile
        35                  40                  45

Gly Thr Ile Thr Tyr Val Gly Asn Thr Tyr Tyr Ala Ser Trp Ala Lys
50                  55                  60

Gly Arg Phe Thr Ile Ser Lys Thr Ser Thr Val Asp Leu Lys Ile
65                  70                  75                  80

Thr Ser Pro Thr Thr Glu Asp Thr Ala Val Tyr Tyr Cys Ala Arg Glu
                85                  90                  95

Ser Gly Thr Ile Tyr Tyr Ser Tyr Phe Asn Leu Trp Gly Gln Gly Thr
            100                 105                 110

Leu Val Thr Val Ser Ser
        115

<210> SEQ ID NO 65
<211> LENGTH: 651
<212> TYPE: DNA
<213> ORGANISM: Artificial Sequence
<220> FEATURE:
<223> OTHER INFORMATION: synthesized

<400> SEQUENCE: 65
gcctatgata tgacccagac tccagcctct gtggaggtag ctgtgggagg cacagtcacc    60
atcaagtgcc aggccagtga ggacatttat agcttcttgg cctggtatca gctgaaacca   120
gggcagtctc ccaagctcct gatccattct gcatcctctc tggcatctgg ggtctcttcg   180
cggttcaaag gcagtggatc tgggacacac ttcactctca ccatcagcgg cgtggagtgt   240
gccgatgctg ccacttatta ttgtcaacag ggttatggta aaaataatgt tgataatgct   300
ttcggcggag ggaccgaggt ggtggtcaaa cgtacggtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaag tctacgcctg cgaagtcacc   600
catcagggcc tgagctcgcc cgtcacaaag agcttcaaca ggggagagtg t           651

<210> SEQ ID NO 66
<211> LENGTH: 330
<212> TYPE: DNA
<213> ORGANISM: Artificial Sequence
<220> FEATURE:
<223> OTHER INFORMATION: synthesized

<400> SEQUENCE: 66
gcctatgata tgacccagac tccagcctct gtggaggtag ctgtgggagg cacagtcacc    60
atcaagtgcc aggccagtga ggacatttat agcttcttgg cctggtatca gctgaaacca   120
gggcagtctc ccaagctcct gatccattct gcatcctctc tggcatctgg ggtctcttcg   180
cggttcaaag gcagtggatc tgggacacac ttcactctca ccatcagcgg cgtggagtgt   240
gccgatgctg ccacttatta ttgtcaacag ggttatggta aaaataatgt tgataatgct   300
ttcggcggag ggaccgaggt ggtggtcaaa                                    330

<210> SEQ ID NO 67
<211> LENGTH: 217

```
<212> TYPE: PRT
<213> ORGANISM: Artificial Sequence
<220> FEATURE:
<223> OTHER INFORMATION: synthesized

<400> SEQUENCE: 67

Ala Tyr Asp Met Thr Gln Thr Pro Ala Ser Val Glu Val Ala Val Gly
1               5                   10                  15

Gly Thr Val Thr Ile Lys Cys Gln Ala Ser Glu Asp Ile Tyr Ser Phe
                20                  25                  30

Leu Ala Trp Tyr Gln Leu Lys Pro Gly Gln Ser Pro Lys Leu Leu Ile
            35                  40                  45

His Ser Ala Ser Ser Leu Ala Ser Gly Val Ser Ser Arg Phe Lys Gly
    50                  55                  60

Ser Gly Ser Gly Thr His Phe Thr Leu Thr Ile Ser Gly Val Glu Cys
65                  70                  75                  80

Ala Asp Ala Ala Thr Tyr Tyr Cys Gln Gln Gly Tyr Gly Lys Asn Asn
                85                  90                  95

Val Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 68
<211> LENGTH: 110
<212> TYPE: PRT
<213> ORGANISM: Artificial Sequence
<220> FEATURE:
<223> OTHER INFORMATION: synthesized

<400> SEQUENCE: 68

Ala Tyr Asp Met Thr Gln Thr Pro Ala Ser Val Glu Val Ala Val Gly
1               5                   10                  15

Gly Thr Val Thr Ile Lys Cys Gln Ala Ser Glu Asp Ile Tyr Ser Phe
                20                  25                  30

Leu Ala Trp Tyr Gln Leu Lys Pro Gly Gln Ser Pro Lys Leu Leu Ile
            35                  40                  45

His Ser Ala Ser Ser Leu Ala Ser Gly Val Ser Ser Arg Phe Lys Gly
    50                  55                  60

Ser Gly Ser Gly Thr His Phe Thr Leu Thr Ile Ser Gly Val Glu Cys
65                  70                  75                  80

Ala Asp Ala Ala Thr Tyr Tyr Cys Gln Gln Gly Tyr Gly Lys Asn Asn
                85                  90                  95

Val Asp Asn Ala Phe Gly Gly Gly Thr Glu Val Val Val Lys
            100                 105                 110
```

<210> SEQ ID NO 69
<211> LENGTH: 1329
<212> TYPE: DNA
<213> ORGANISM: Artificial Sequence
<220> FEATURE:
<223> OTHER INFORMATION: synthesized

<400> SEQUENCE: 69

```
cagtcggtgg aggagtccgg gggtcgcctg gtcacgcctg ggacacccct gacactcacc      60
tgcacagtct ccggaatcga ccttaatacc tacgacatga tctgggtccg ccaggctcca     120
gggaaggggc tggagtggat cggaatcatt acttatagtg gtagtagata ctacgcgaac     180
tgggcgaaag gccgattcac catctccaaa acctcgacca cggtggatct gagaatcacc     240
agtccgacaa ccgaggacac ggccacctat ttctgtgcca gggattatat gagtggttcc     300
cacttgtggg gcccaggcac cctcgtcacc gtctcgagcg ctagcaccaa gggcccatcg     360
gtcttccccc tggcaccctc ctccaagagc acctctgggg gcacagcggc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acccagacct acatctgcaa cgtgaatcac     600
aagcccagca acaccaaggt ggacaagaga gttgagccca aatcttgtga caaaactcac     660
acatgcccac cgtgcccagc acctgaactc ctggggggac cgtcagtctt cctcttcccc     720
ccaaaaccca aggacaccct catgatctcc cggacccctg aggtcacatg cgtggtggtg     780
gacgtgagcc acgaagaccc tgaggtcaag ttcaactggt acgtggacgg cgtggaggtg     840
cataatgcca agacaaagcc gcgggaggag cagtacaaca gcacgtaccg tgtggtcagc     900
gtcctcaccg tcctgcacca ggactggctg aatggcaagg agtacaagtg caaggtctcc     960
aacaaagccc tcccagcccc catcgagaaa accatctcca aagccaaagg gcagccccga    1020
gaaccacagg tgtacaccct gcccccatcc cgggaggaga tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctata gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaa                                                            1329
```

<210> SEQ ID NO 70
<211> LENGTH: 339
<212> TYPE: DNA
<213> ORGANISM: Artificial Sequence
<220> FEATURE:
<223> OTHER INFORMATION: synthesized

<400> SEQUENCE: 70

```
cagtcggtgg aggagtccgg gggtcgcctg gtcacgcctg ggacacccct gacactcacc      60
tgcacagtct ccggaatcga ccttaatacc tacgacatga tctgggtccg ccaggctcca     120
gggaaggggc tggagtggat cggaatcatt acttatagtg gtagtagata ctacgcgaac     180
tgggcgaaag gccgattcac catctccaaa acctcgacca cggtggatct gagaatcacc     240
agtccgacaa ccgaggacac ggccacctat ttctgtgcca gggattatat gagtggttcc     300
cacttgtggg gcccaggcac cctcgtcacc gtctcgagc                            339
```

```
<210> SEQ ID NO 71
<211> LENGTH: 443
<212> TYPE: PRT
<213> ORGANISM: Artificial Sequence
<220> FEATURE:
<223> OTHER INFORMATION: synthesized

<400> SEQUENCE: 71

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Thr Tyr Asp
            20                  25                  30

Met Ile Trp Val Arg Gln Ala Pro Gly Lys Gly Leu Glu Trp Ile Gly
        35                  40                  45

Ile Ile Thr Tyr Ser Gly Ser Arg Tyr Tyr Ala Asn Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Arg Asp Tyr
                85                  90                  95

Met Ser Gly Ser His Leu Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365
```

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 72
<211> LENGTH: 113
<212> TYPE: PRT
<213> ORGANISM: Artificial Sequence
<220> FEATURE:
<223> OTHER INFORMATION: synthesized

<400> SEQUENCE: 72

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Thr Tyr Asp
            20                  25                  30

Met Ile Trp Val Arg Gln Ala Pro Gly Lys Gly Leu Glu Trp Ile Gly
        35                  40                  45

Ile Ile Thr Tyr Ser Gly Ser Arg Tyr Tyr Ala Asn Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Arg Asp Tyr
                85                  90                  95

Met Ser Gly Ser His Leu Trp Gly Pro Gly Thr Leu Val Thr Val Ser
            100                 105                 110

Ser

<210> SEQ ID NO 73
<211> LENGTH: 651
<212> TYPE: DNA
<213> ORGANISM: Artificial Sequence
<220> FEATURE:
<223> OTHER INFORMATION: synthesized

<400> SEQUENCE: 73
gcctatgata tgacccagtc tccatcttcc gtgtctgcat ctgtaggaga cagagtcacc      60
atcaagtgtc aggccagtga ggacatttat agcttcttgg cctggtatca gcagaaacca     120
gggaaagccc ctaagctcct gatccattct gcatcctctc tggcatctgg ggtcccatca     180
aggttcagcg gcagtggatc tgggacagat tcactctcac ccatcagcag cctgcagcct     240
gaagattttg caacttacta ttgtcaacag ggttatggta aaaataatgt tgataatgct     300
ttcggcggag ggaccaaggt ggagatcaaa cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t              651

<210> SEQ ID NO 74
<211> LENGTH: 330
<212> TYPE: DNA
<213> ORGANISM: Artificial Sequence
<220> FEATURE:
<223> OTHER INFORMATION: synthesized

<400> SEQUENCE: 74

```
gcctatgata tgacccagtc tccatcttcc gtgtctgcat ctgtaggaga cagagtcacc      60
atcaagtgtc aggccagtga ggacatttat agcttcttgg cctggtatca gcagaaacca     120
gggaaagccc ctaagctcct gatccattct gcatcctctc tggcatctgg ggtcccatca     180
aggttcagcg gcagtggatc tgggacagat tcactctca ccatcagcag cctgcagcct     240
gaagattttg caacttacta ttgtcaacag ggttatggta aaaataatgt tgataatgct     300
ttcggcggag ggaccaaggt ggagatcaaa                                      330
```

<210> SEQ ID NO 75
<211> LENGTH: 217
<212> TYPE: PRT
<213> ORGANISM: Artificial Sequence
<220> FEATURE:
<223> OTHER INFORMATION: synthesized

<400> SEQUENCE: 75

```
Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 76
<211> LENGTH: 110
<212> TYPE: PRT

<213> ORGANISM: Artificial Sequence
<220> FEATURE:
<223> OTHER INFORMATION: synthesized

<400> SEQUENCE: 76

```
Ala Tyr Asp Met Thr Gln Ser Pro Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys
            100                 105                 110
```

<210> SEQ ID NO 77
<211> LENGTH: 1335
<212> TYPE: DNA
<213> ORGANISM: Artificial Sequence
<220> FEATURE:
<223> OTHER INFORMATION: synthesized

<400> SEQUENCE: 77

| | | | | | |
|---|---|---|---|---|---|
| cagtcggtgg | aggagtctgg | gggaggcttg | gtccagcctg | ggggtccct | gagactctcc | 60 |
| tgtaccgcct | ctggaatcga | ccttaatacc | tacgacatga | tctgggtccg | ccaggctcca | 120 |
| ggcaagggc | tagagtgggt | tggaatcatt | acttatagtg | gtagtagata | ctacgcgaac | 180 |
| tgggcgaaag | gccgattcac | catctccaaa | gacaatacca | agaacacggt | gtatctgcaa | 240 |
| atgaacagcc | tgagagctga | ggacacggct | gtgtattact | gtgcgagaga | ttatatgagt | 300 |
| ggttccact | tgtggggcca | gggaaccctg | gtcaccgtct | cgagcgctag | caccaagggc | 360 |
| ccatcggtct | tccccctggc | accctcctcc | aagagcacct | ctgggggcac | agcggccctg | 420 |
| ggctgcctgg | tcaaggacta | cttccccgaa | ccggtgacgg | tgtcgtggaa | ctcaggcgcc | 480 |
| ctgaccagcg | gcgtgcacac | cttcccggct | gtcctacagt | cctcaggact | ctactccctc | 540 |
| agcagcgtgg | tgaccgtgcc | ctccagcagc | ttgggcaccc | agacctacat | ctgcaacgtg | 600 |
| aatcacaagc | ccagcaacac | caaggtggac | aagagagttg | agcccaaatc | ttgtgacaaa | 660 |
| actcacacat | gcccaccgtg | cccagcacct | gaactcctgg | ggggaccgtc | agtcttcctc | 720 |
| ttcccccaa | aacccaagga | caccctcatg | atctcccgga | ccctgaggt | cacatgcgtg | 780 |
| gtggtggacg | tgagccacga | agaccctgag | gtcaagttca | actggtacgt | ggacggcgtg | 840 |
| gaggtgcata | atgccaagac | aaagccgcgg | gaggagcagt | acaacagcac | gtaccgtgtg | 900 |
| gtcagcgtcc | tcaccgtcct | gcaccaggac | tggctgaatg | gcaaggagta | caagtgcaag | 960 |
| gtctccaaca | aagccctccc | agcccccatc | gagaaaacca | tctccaaagc | caaagggcag | 1020 |
| ccccgagaac | cacaggtgta | caccctgccc | ccatcccggg | aggagatgac | caagaaccag | 1080 |
| gtcagcctga | cctgcctggt | caaaggcttc | tatcccagcg | acatcgccgt | ggagtgggag | 1140 |
| agcaatgggc | agccggagaa | caactacaag | accacgcctc | ccgtgctgga | ctccgacggc | 1200 |
| tccttcttcc | tctatagcaa | gctcaccgtg | gacaagagca | ggtggcagca | ggggaacgtc | 1260 |

```
ttctcatgct ccgtgatgca tgaggctctg cacaaccact acacgcagaa gagcctctcc    1320
ctgtctccgg gtaaa                                                     1335
```

<210> SEQ ID NO 78
<211> LENGTH: 345
<212> TYPE: DNA
<213> ORGANISM: Artificial Sequence
<220> FEATURE:
<223> OTHER INFORMATION: synthesized

<400> SEQUENCE: 78

```
cagtcggtgg aggagtctgg ggaggcttg gtccagcctg ggggtccct gagactctcc      60 tgtaccgcct ctggaatcga ccttaatacc tacgacatga tctgggtccg ccaggctcca    120
ggcaaggggc tagagtgggt tggaatcatt acttatagtg gtagtagata ctacgcgaac    180
tgggcgaaag gccgattcac catctccaaa gacaatacca gaacacggt gtatctgcaa    240 atgaacagcc tgagagctga ggacacggct gtgtattact gtgcgagaga ttatatgagt    300
ggttcccact gtgggggcca gggaaccctg gtcaccgtct cgagc                    345
```

<210> SEQ ID NO 79
<211> LENGTH: 445
<212> TYPE: PRT
<213> ORGANISM: Artificial Sequence
<220> FEATURE:
<223> OTHER INFORMATION: synthesized

<400> SEQUENCE: 79

```
Gln Ser Val Glu Glu Ser Gly Gly Gly Leu Val Gln Pro Gly Gly Ser
1               5                   10                  15

Leu Arg Leu Ser Cys Thr Ala Ser Gly Ile Asp Leu Asn Thr Tyr Asp
            20                  25                  30

Met Ile Trp Val Arg Gln Ala Pro Gly Lys Gly Leu Glu Trp Val Gly
        35                  40                  45

Ile Ile Thr Tyr Ser Gly Ser Arg Tyr Tyr Ala Asn Trp Ala Lys Gly
    50                  55                  60

Arg Phe Thr Ile Ser Lys Asp Asn Thr Lys Asn Thr Val Tyr Leu Gln
65                  70                  75                  80

Met Asn Ser Leu Arg Ala Glu Asp Thr Ala Val Tyr Tyr Cys Ala Arg
                85                  90                  95

Asp Tyr Met Ser Gly Ser His Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
```

```
            225                 230                 235                 240
        Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                        260                 265                 270

Phe Asn Trp Tyr Val Asp Gly Val Glu Val His Asn Ala Lys Thr Lys
                        275                 280                 285

Pro Arg Glu Glu Gln Tyr Asn Ser Thr Tyr Arg Val Val Ser Val Leu
                        290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Tyr Thr Leu Pro Pro Ser
                        340                 345                 350

Arg Glu Glu Met Thr Lys Asn Gln Val Ser Leu Thr Cys Leu Val Lys
                        355                 360                 365

Gly Phe Tyr Pro Ser Asp Ile Ala Val Glu Trp Glu Ser Asn Gly Gln
                        370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro Gly Lys
                        435                 440                 445

<210> SEQ ID NO 80
<211> LENGTH: 115
<212> TYPE: PRT
<213> ORGANISM: Artificial Sequence
<220> FEATURE:
<223> OTHER INFORMATION: synthesized

<400> SEQUENCE: 80

Gln Ser Val Glu Glu Ser Gly Gly Leu Val Gln Pro Gly Gly Ser
1               5                   10                  15

Leu Arg Leu Ser Cys Thr Ala Ser Gly Ile Asp Leu Asn Thr Tyr Asp
                20                  25                  30

Met Ile Trp Val Arg Gln Ala Pro Gly Lys Gly Leu Glu Trp Val Gly
                35                  40                  45

Ile Ile Thr Tyr Ser Gly Ser Arg Tyr Tyr Ala Asn Trp Ala Lys Gly
                50                  55                  60

Arg Phe Thr Ile Ser Lys Asp Asn Thr Lys Asn Thr Val Tyr Leu Gln
65                  70                  75                  80

Met Asn Ser Leu Arg Ala Glu Asp Thr Ala Val Tyr Tyr Cys Ala Arg
                85                  90                  95

Asp Tyr Met Ser Gly Ser His Leu Trp Gly Gln Gly Thr Leu Val Thr
                100                 105                 110

Val Ser Ser
        115

<210> SEQ ID NO 81
<211> LENGTH: 816
<212> TYPE: DNA
```

<213> ORGANISM: Artificial Sequence
<220> FEATURE:
<223> OTHER INFORMATION: synthesized

<400> SEQUENCE: 81

```
tttactgtca cggttcccaa ggacctatat gtggtagagt atggtagcaa tatgacaatt      60
gaatgcaaat tcccagtaga aaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcagggtgt accgctgcat gatcagctat      300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctaccca aggccgaagt catctggaca agcagtgacc atcaagtcct gagtggtaag      480
accaccacca ccaattccaa gagagaggag aagcttttca atgtgaccag cacactgaga     540
atcaacacaa caactaatga atttcctac tgcactttta ggagattaga tcctgaggaa      600
aaccatacag ctgaattggt catcccagaa ctacctctgg cacatcctcc aaatgaaagg     660
actcacttgg taattctggg agccatctta ttatgccttg gtgtagcact gacattcatc     720
ttccgtttaa gaaagggag aatgatggat gtgaaaaaat gtggcatcca agatacaaac      780
tcaaagaagc aaagtgatac acatttggag gagacg                              816
```

<210> SEQ ID NO 82
<211> LENGTH: 272
<212> TYPE: PRT
<213> ORGANISM: Artificial Sequence
<220> FEATURE:
<223> OTHER INFORMATION: synthesized

<400> SEQUENCE: 82

```
Phe Thr Val Thr Val Pro Lys Asp Leu Tyr Val Val Glu Tyr Gly Ser
1               5                   10                  15
Asn Met Thr Ile Glu Cys Lys Phe Pro Val Glu Lys Gln Leu Asp Leu
            20                  25                  30
Ala Ala Leu Ile Val Tyr Trp Glu Met Glu Asp Lys Asn Ile Ile Gln
        35                  40                  45
Phe Val His Gly Glu Glu Asp Leu Lys Val Gln His Ser Ser Tyr Arg
    50                  55                  60
Gln Arg Ala Arg Leu Leu Lys Asp Gln Leu Ser Leu Gly Asn Ala Ala
65                  70                  75                  80
Leu Gln Ile Thr Asp Val Lys Leu Gln Asp Ala Gly Val Tyr Arg Cys
                85                  90                  95
Met Ile Ser Tyr Gly Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
Val Thr Ser Glu His Glu Leu Thr Cys Gln Ala Glu Gly Tyr Pro Lys
    130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Phe Asn Val Thr
                165                 170                 175
Ser Thr Leu Arg Ile Asn Thr Thr Thr Asn Glu Ile Phe Tyr Cys Thr
            180                 185                 190
```

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
            245                 250                 255

Gln Asp Thr Asn Ser Lys Lys Gln Ser Asp Thr His Leu Glu Glu Thr
            260                 265                 270

<210> SEQ ID NO 83
<211> LENGTH: 663
<212> TYPE: DNA
<213> ORGANISM: Artificial Sequence
<220> FEATURE:
<223> OTHER INFORMATION: synthesized

<400> SEQUENCE: 83
tttactgtca cggttcccaa ggacctatat gtggtagagt atggtagcaa tatgacaatt    60
gaatgcaaat tcccagtaga aaacaattga gacctggctg cactaattgt ctattgggaa   120
atggaggata gaacattat tcaatttgtg catggagagg aagacctgaa ggttcagcat    180
agtagctaca gacagagggc ccggctgttg aaggaccagc tctccctggg aaatgctgca   240
cttcagatca cagatgtgaa attgcaggat gcaggggtgt accgctgcat gatcagctat   300
ggtggtgccg actacaagcg aattactgtg aagtcaatg ccccatacaa caaaatcaac    360
caaagaattt tggttgtgga tccagtcacc tctgaacatg aactgacatg tcaggctgag   420
ggctacccca aggccgaagt catctggaca agcagtgacc atcaagtcct gagtggtaag   480
accaccacca ccaattccaa gagagaggag aagcttttca atgtgaccag cacactgaga   540
atcaacacaa caactaatga gattttctac tgcacttttta ggagattaga tcctgaggaa   600
aaccatacag ctgaattggt catcccagaa ctacctctgg cacatcctcc aaatgaaagg   660
act                                                                 663

<210> SEQ ID NO 84
<211> LENGTH: 221
<212> TYPE: PRT
<213> ORGANISM: Artificial Sequence
<220> FEATURE:
<223> OTHER INFORMATION: synthesized

<400> SEQUENCE: 84

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val

```
                    100                 105                 110
Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr
    210                 215                 220
```

ANTI-PD-L1 ANTIBODIES AND METHODS OF MAKING AND USING THEREOF

REFERENCE TO SEQUENCE LISTING

In accordance with MPEP 502.05(L), the present specification makes reference to a Sequence Listing submitted electronically as a .txt file named "SIBA010_ST25.txt" on Nov. 19, 2019. The .txt file was generated on Aug. 15, 2018 and is 127 kb in size. The entire contents of the Sequence Listing are herein incorporated by reference.

CROSS REFERENCE TO RELATED APPLICATIONS

This application claims the benefit of U.S. Provisional Patent Application No. 62/524,553 filed Jun. 25, 2017, which application is expressly incorporated herein by reference in its entirety.

TECHNICAL FIELD

The present disclosure generally relates to the technical field of antibodies, and more particularly relates to making and using anti-PD-L1 antibodies.

BACKGROUND

Cancer is a major health problem across the world. In the United States alone it is estimated that in 2016 there were 1,685,210 new cases of cancer diagnosed and 595,690 deaths from the disease (http://www.cancer.gov). As such, any pharmaceutical agent that can reduce the severity or mortality rate from cancer is desirable.

In the immune system, resting T-cells can be activated to respond to antigen through a primary signal delivered through the T-cell receptor (TCR) by foreign antigen peptides presented by antigen-presenting cells (APCs). In addition to this primary signal, there are secondary positive and negative co-stimulatory signals which further influence the response of the T-cells. A secondary positive signal is required for full T-cell activation (Lafferty et al., Ausl. J. Exp. Biol. Med. Sci. 53: 27-42 (1975)). Negative secondary signals can result in T-cell suppression and tolerance.

Programmed death 1 (PD-1) is a member of the CD28 family of receptors and is expressed on T-cells and other cell types. PD-1 is one of the routes used by to transmit negative secondary signals into T-cells. PD-L1 is a cell-surface ligand glycoproteins for PD-1 which was shown to downregulate T-cell activation upon binding to PD-1 (Freeman et al. J. Exp. Med. 192: 1027-34 (2000)).

Cancerous tumors can adopt a variety of mechanisms to avoid detection and/or destruction by the host immune system. One method utilized by a variety of tumors is to suppress the immune T-cell response by the expression of PD-L1 on the surface of tumor cells. When the PD-L1 engages its receptor PD-1 on the surface of T-cells, a negative co-stimulatory signal is sent into the T-cell that results in the suppression of the T-cell. In this manner, tumor cells are able to avoid a T-cell mediated response of the host immune system.

PD-L1, also known as B7-H1 or CD274, is a 40 kDa type 1 transmembrane protein that has been shown to be expressed in several human cancers and is associated with increased tumor aggressiveness and an increased risk of death (Thomson et al. PNAS 101: 17174-9 (2004)). PD-L1 expression in cancers is thought to suppress the immune response to tumors via suppression of T-cells (Dong et al. Nat. Med. 8: 793-800 (2002)).

While pharmaceutical agents that are able to bind to PD-L1 and block the negative co-stimulatory signal from suppressing the T-cell response have been shown to increase the host immune response to cancerous tumors, the beneficial response for cancer patients varies (see Reiss et al. Immunotherapy. 6:459-75 (2014)). It remains unclear what is the optimal PD-L1 binding site(s) and relevant affinity for developing the most effective and tumor cell-specific anti-PD-L1 antibodies for cancer treatment.

SUMMARY

The present disclosure provides, among others, anti-PD-L1 monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

In one aspect, the application provides an isolated monoclonal antibody (mAb) or antigen-binding fragment thereof with binding specificity to human PD-1.

In one embodiment, the isolated mAb or antigen-binding fragment may have an amino acid sequence have a percentage homology with SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, or SEQ ID NO:80. The percentage homology may be at or above the level of 70%, 75%, 80%, 85%, 90%, 95%, 99%, or any range between 70-100%.

In one embodiment, the isolated mAb or antigen-binding fragment may have a binding affinity to PD-L1 with a Kd not greater than 30 nM, 40 nM, 50 nM, 60 nM, 70 nM, 80 nM, 90 nM, or 100 nM.

In one embodiment, the isolated mAb or antigen-binding fragment may exhibit one or more functional properties. Example functional properties include high affinity binding to PD-L1, inhibiting binding of PD-L1 to PD-1, enhancing T cell activation, the ability to stimulate antibody responses and/or the ability to reverse the suppressive function of immunosuppressive cells, such as T regulatory cells. In one embodiment, the isolated mAb or antigen-binding fragment may enhance T-cell activation via T-cell proliferation, IFN-γ and/or IL-2 secretion, or a combination thereof.

The isolated mAb or antigen-binding fragment may include a human framework region. In one embodiment, the isolated mAb or antigen-binding fragment may be a humanized antibody, a chimeric antibody, or a recombinant antibody.

In one embodiment, the isolated mAb may be an antibody in IgG family. In one embodiment, the isolated mAb is an IgG. In one embodiment, the isolated mAb may be a bispecific antibody, tri-specific antibody, or multi-specific antibody. In one embodiment, the antigen-binding fragment may include a Fv, a Fab, a F(ab')2, a scFV or a scFV2 fragment.

In one embodiment, the isolated mAb or antigen-binding fragment may have an IgG1 heavy chain that include an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, or SEQ ID NO:79. In one embodiment, the percentage homology may be at or above the level of 70%, 75%, 80%, 85%, 90%, 95%, 99%, or any range between 70-100%.

In one embodiment, the isolated mAb or antigen-binding fragment may have a kappa light chain that include an amino acid sequence having a percentage homology with SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, and SEQ ID NO:75. In one embodiment, the percentage homology may be at or above the level of 70%, 75%, 80%, 85%, 90%, 95%, 99%, or any range between 70-100%.

In one embodiment, the isolated mAb or antigen-binding fragment may have a variable light chain that include an amino acid sequence having a percentage homology with SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, or SEQ ID NO:76. In one embodiment, the percentage homology may be at or above the level of 70%, 75%, 80%, 85%, 90%, 95%, 99%, or any range between 70-100%.

In one embodiment, the isolated mAb or antigen-binding fragment may have a variable heavy chain that comprises an amino acid sequence having a percentage homology with SEQ ID NO:8, SEQ ID NO:16, SEQ ID NO:24, SEQ ID NO:32, SEQ ID NO:40, SEQ ID NO:48, SEQ ID NO:56, SEQ ID NO:64, and SEQ ID NO:72, or SEQ ID NO:80. In one embodiment, the percentage homology may be at or above the level of 70%, 75%, 80%, 85%, 90%, 95%, 99%, or any range between 70-100%.

The application further provides isolated nucleic acids that encode the isolated mAB or antigen-binding fragment disclosed thereof. In one embodiment the nucleic acid encodes an amino acid sequence having a percentage homology with an IgG1 heavy chain SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71 or SEQ ID NO:79. In one embodiment, the nucleic acid encodes an amino acid sequence having a percentage homology with a kappa light chain SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, or SEQ ID NO:75. In one embodiment, the nucleic acid encodes an amino acid sequence having a percentage homology with a variable light chain SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, or SEQ ID NO:76. In one embodiment, the nucleic acid encodes an amino acid sequence having a percentage homology with a variable heavy chain SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, or SEQ ID NO:80. In one embodiment, the percentage homology may be at or above the level of 70%, 75%, 80%, 85%, 90%, 95%, 99%, or any range between 70-100%.

The application further provides expression vectors containing one or more of the nucleic acid sequence disclosed herein. In some embodiments, the nucleic acid sequence encodes a peptide or protein disclosed herein.

In one embodiment, the expression vector described herein is present in a cell and expressible. In one embodiment, the cell is a host cell. In one embodiment, host cell can be a prokaryotic cell or a eukaryotic cell.

In another aspect, the application provides methods for producing the antibodies or antigen-binding fragment disclosed thereof. In one embodiment, the method includes the steps of providing a host that contains an expression vector expressible in the host cell, the expression vector comprises a nucleic acid sequence disclosed herein, to produce an antibody by the expression of the nucleic acid sequence.

The application further provides an immuno-conjugate that includes the anti-PD-L1 antibodies or fragments thereof. In one embodiment, the immuno-conjugate comprises a drug unit or an imaging agent linked to an anti-PDL1 mAb or antigen-binding fragment thereof through a linker.

The linker may be cleavable or noncleavable. In one embodiment, the linker is a chemical linker. In one embodiment, the linker comprises a covalent bond such as an ester bond, an ether bond, an amine bond, an amide bond, a disulphide bond, an imide bond, a sulfone bond, a phosphate bond, a phosphorus ester bond, a peptide bond, a hydrazone bond or a combination thereof. In one embodiment, the linker comprises a hydrophobic poly(ethylene glycol) linker. In one embodiment, the linker comprises a peptide bond.

In one embodiment, the drug unit in the immuno-conjugate may be a chemotherapeutic agent, a growth inhibitory agent, a drug unit from class of calicheamicin, an antimitotic agent, a toxin, a radioactive isotope, a therapeutic agent, or a combination thereof. In one embodiment, the drug unit comprises a calicheamicin, ozogamicin, monomethyl auristatin E, emtansine, a derivative or a combination thereof.

In one embodiment, the drug unit is selected from a cytotoxic agent, an immune regulatory reagent, an imaging agent or a combination thereof. In one embodiment, the cytotoxic agent is selected from a growth inhibitory agent or a chemotherapeutic agent from a class of tubulin binders, DNA intercalators, DNA alkylators, enzyme inhibitors, immune modulators, antimetabolite agents, radioactive isotopes, or a combination thereof. In one embodiment, the cytotoxic agent is selected from a calicheamicin, ozogamicin, monomethyl auristatin E, emtansine, a derivative or a combination thereof.

In one embodiment, the immune regulatory reagents activate or suppress immune cells, T cell, NK cell, B cell, macrophage, or dendritic cell.

In one embodiment, the imaging agent may be radionuclide, a florescent agent, a quantum dots, or a combination thereof.

The application further provides a pharmaceutical composition. In one embodiment, the pharmaceutical composition includes an isolated mAb or antigen-binding fragment disclosed herein and a pharmaceutically acceptable carrier. In one embodiment, the pharmaceutical composition includes an immuno-conjugate disclosed herein and a pharmaceutically acceptable carrier.

In one embodiment, the pharmaceutical composition may further include a radioisotope, radionuclide, a toxin, a therapeutic agent, a chemotherapeutic agent or a combination thereof. In one embodiment, a pharmaceutical composition may include a drug unit, an isolated mAb or antigen-binding fragment that binds specifically to human PD-L1 and a pharmaceutically acceptable carrier. Example drug unit that are useful in the present application may include without limitation capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemcitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, letrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, calicheamicin, monomethyl auristatin E, emtansine, ozogamicin, or a derivative or a combination thereof.

In another aspect, the application provides methods for treating a cancer using the anti-PD-L1 antibodies and antigen-binding fragments disclosed herein. In one embodiment, the method includes the step of administering to the subject an effective amount of the isolated mAb or antigen-binding fragment disclosed herein. In some embodiments, the cancer has cells that express PD-1.

In one embodiment, the method includes directly injecting into the tumour site an effective amount of the monoclonal antibodies, the antigen-binding fragment thereof, and the immuno-conjugates and disclosed herein.

In one embodiment, the method includes administering to the subject an effective amount of the isolated mAb or antigen-binding fragment disclosed herein, and co-administering an effective amount of a therapeutic agent. In some embodiments, the therapeutic agent can be an antibody, a chemotherapy agent, an enzyme, or a combination thereof. Example therapeutic agents include, without limitation, capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, a derivative or a combination thereof.

Varieties of cancer may be treated using disclosed anti-PD-L1 antibodies or antigen-binding fragments. Example cancers include, without limitation, breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer.

In some embodiment, the subject receiving treatment is a human. In one embodiment, a solution is provided that comprises an effective concentration of the isolated mAb or an antigen-binding fragment that binds specifically to human PD-L1, wherein the solution is blood plasma in a subject.

BRIEF DESCRIPTION OF THE DRAWINGS

The foregoing and other features of this disclosure will become more fully apparent from the following description and appended claims, taken in conjunction with the accompanying drawings.

Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 shows an example of the PD-L1 binding ELISA performed on the supernatants from a B cell culture plate. Shaded wells indicate wells that were identified as positive for anti-PD-L1 antibodies.

FIG. 2 is an example of bio-layer interferometry analysis of the ability of an antibody supernatant to block the association between PD-L1 to PD-1. The black trace utilizes a block antibody supernatant whereas the gray trace is with a non-blocking antibody supernatant. Octet analysis measures PD-1 binding to biotinylated PD-L1 loaded onto a streptavidin sensor after the addition of PD-L1 specific antibodies that block or do not block PD-1 binding to PD-L1.

FIG. 3 shows bio-layer interferometry analysis of the ability of antibodies AB1-AB5 to block the association between PD-L1 to PD-1, starting from PD-L1 binding followed by baseline followed by PD-L1 binding. Negative control is an anti-PD-L1 antibody which can bind to PD-L1 but does not block the association between PD-L1 to PD-1. Octet analysis indicates that a control PD-L1 specific antibody binding to biotinylated PD-L1 loaded onto a streptavidin sensor does not block PD-1 binding to PD-L1.

FIG. 5 shows the example antibodies binding to lung cancer cell line A441.

DETAILED DESCRIPTION

Figure 4C:
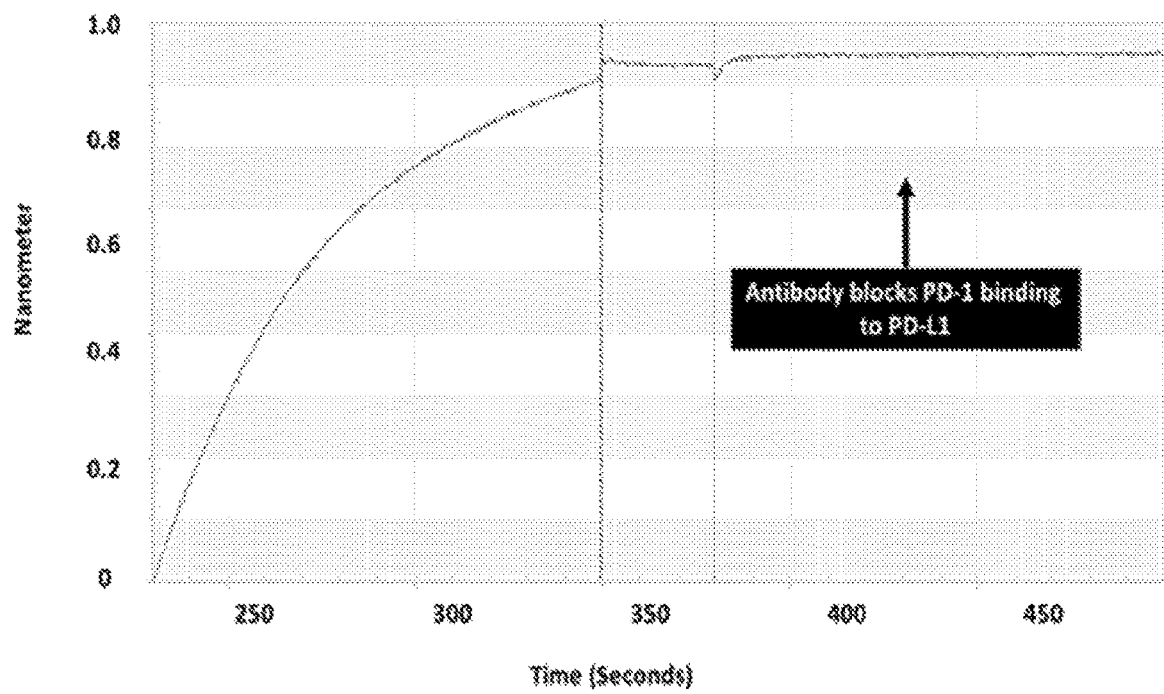
FIG. 4 is an example of binding kinetics data for two anti-PD-L1 antibodies binding to PD-L1. The data shown is for the 5-minute association followed by the 15-minute dissociation for various concentrations of PD-L1. 4A shows AB1HU blocking recombinant PD-1 binding to recombinant PD-L1; 4B shows AB2HU blocking recombinant PD-1 binding to recombinant PD-L1; 4C shows AB3HU blocking recombinant PD-1 binding to recombinant PD-L1; 4D shows AB4HU blocking recombinant PD-1 binding to recombinant PD-L1; and 4E shows AB5HU blocking recombinant PD-1 binding to recombinant PD-L1.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The disclosure provides, among others, isolated antibodies, methods of making such antibodies, bispecific or multi-specific molecules, antibody-drug conjugates and/or immuno-conjugates composed of such antibodies or antigen binding fragments, pharmaceutical compositions containing the antibodies, bispecific or multi-specific molecules, antibody-drug conjugates and/or immuno-conjugates, methods for making disclosed antibodies, antigen-binding fragments, and compositions, and method of using the above for treatment of cancer.

In one aspect, the present disclosure provides isolated monoclonal antibodies that bind to human PD-L1 and the antigen-binding fragments thereof. The antibodies and the antigen-binding fragments thereof exhibit one or more desirable functional properties, such as high affinity binding to PD-L1, the ability to inhibit binding of PD-L1 to PD-1, the ability to enhance T cell activation including proliferation, IFN-γ and/or IL-2 secretion, the ability to stimulate antibody responses and/or the ability to reverse the suppressive function of immunosuppressive cells, such as T regulatory cells. In one embodiment, the antibodies and the antigen-binding fragments thereof may be derived from specific heavy and light chain amino acid sequences and/or structural features such as complementarity determining regions (CDRs) composed of specific amino acid sequences.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity. In some embodiments, the antibody may be monoclonal, polyclonal, chimeric, single chain, bispecific or bi-effective, and humanized antibodies, as well as active fragments thereof. Examples of active fragments of molecules that bind to known antigens include Fab, F(ab')$_2$, scFv and Fv fragments, including the products of a Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site with immunologic binding specificity to an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, Nature, 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with both human PD-L1 protein and cells transiently expressing human PD-L1 on the cell surface. Rabbits are known to create antibodies of high affinity, diversity and specificity (Weber et al. Exp. Mol. Med. 49:e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9:e86184 (2014).

The term "antigen- or epitope-binding portion or fragment" refers to fragments of an antibody that are capable of binding to an antigen (PD-L1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller sub-fragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen- or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and µ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)). In one embodiment, the "humanized antibody" may be obtained by genetic engineering approach that enables production of affinity-matured humanlike polyclonal antibodies in large animals such as, for example, rabbits (see, e.g. U.S. Pat. No. 7,129,084).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$, alternatively at least about $10^{-10}$ M, at least about $10^{-11}$ M, at least about $10^{-12}$ M, or greater, where KD refers to a dissociation rate of a particular antibody-antigen interaction. In some embodiments, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

In another aspect, the application provides pharmaceutical compositions. Formulation of the pharmaceutical composition according to the disclosure can be accomplished according to standard methodology know to those of ordinary skill in the art. The antibodies according to the disclosure can be prepared in a physiologically acceptable formulation and may comprise a pharmaceutically acceptable carrier, diluent and/or excipient using known techniques. For example, the antibody according to the disclosure and as described herein including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

In a further aspect, the application provides methods for treating a subject using the mAbs, their antigen-binding fragments, and compositions disclosed herein. In one embodiment, the method is used to inhibit growth of tumor cells. In some embodiments, the application provides methods of using the antibodies to stimulate a protective autoimmune response, to modify an immune response or to stimulate antigen-specific immune responses. In some embodiments, the methods including the steps of using the antibodies to stimulate a protective autoimmune response, to modify an immune response or to stimulate antigen-specific immune responses. In some embodiments, the methods include administering the disclosed composition into a subject for treating a cancer.

The compositions of the present disclosure may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. For example, the composition may be administered by topical, oral, rectal, nasal, interdermal, intraperitoneal, or parenteral (for example, intravenous, subcutaneous, or intramuscular) routes. In one embodiment, the administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

In one embodiment, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

Further, the term "therapeutically effective amount" refers to the amount of antibody which, when administered to a human or animal, elicits a response which is sufficient to result in a therapeutic effect in said human or animal. The effective amount is readily determined by one of ordinary skill in the art following routine procedures.

Further biologically active agents may be present in the pharmaceutical composition of the disclosure dependent on the intended use. In one embodiment, the composition may be administered in combination with other compositions comprising a biologically active substance or compound.

Example biologically active substances or compounds include without limitation compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B12, cysteine, a precursor of acetylcholine, lecithin, choline, *Ginkgo biloba*, acyetyl-L-carnitine, idebenone, propentofylline, or a xanthine derivative, together with an antibody according to the present disclosure and, optionally, a pharmaceutically acceptable carrier and/or a diluent and/or an excipient and instructions for the treatment of diseases.

The pharmaceutical composition may further comprise proteinaceous carriers such as, for example, serum albumin or immunoglobulin, particularly of human origin. Proteinaceous pharmaceutically active matter may be present in amounts between 1 ng and 10 mg per dose. Generally, the regime of administration should be in the range of between 0.1 µg and 10 mg of the antibody according to the disclosure, particularly in a range 1.0 µg to 1.0 mg, and more particularly in a range of between 1.0 µg and 100 µg, with all individual numbers falling within these ranges also being part of the disclosure. If the administration occurs through continuous infusion a more proper dosage may be in the range of between 0.01 µg and 10 mg units per kilogram of body weight per hour with all individual numbers falling within these ranges also being part of the disclosure.

The present disclosure may be understood more readily by reference to the following detailed description of specific embodiments included herein. Although the present disclosure has been described with reference to specific details of certain embodiments thereof, it is not intended that such details should be regarded as limitations upon the scope of the disclosure. All references cited or referred to in this disclosure are hereby specifically incorporated by reference in their entireties.

EXAMPLES

Example 1: Generation of Anti-PD-L1 Antibodies

Monoclonal antibodies against human PD-L1 were developed by immunizing New Zealand white rabbits. The initial immunizations were with 100 μg of recombinant human PD-L1 extracellular domain mixed 1:1 v/v with Complete Freund's Adjuvant performed by subcutaneous injection. Subsequent boosts were performed at weeks 3, 6, 9, and 10 with 50 μg of antigen in Incomplete Freund's Adjuvant. In addition to antigen, on weeks 6, 9, and 10, the animals were also boosted with 1×106 HEK-293 cells which were transiently transfected to express full-length human PD-L1.

On weeks 9 and 12 the serum from the animals was tested for anti-PD-L1 titer by ELISA. 96-well plates were coated overnight by passive adsorption at 4° C. with goat anti-rabbit IgG antibody (Jackson ImmunoResearch). The coated wells were washed and blocked with 1% milk for 1 hour at room temperature followed by a 1 hour room temperature incubation with human PD-L1 extracellular domain human Fc domain fusion protein. After washing, undiluted serum is added to the wells and serially diluted 1:10 across the plate over a total of 7 wells each. After a 1 hour incubation at room temperature the plates were washed and then incubated with a goat anti-human IgG Fc-specific horseradish peroxidase-conjugated antibody (Jackson ImmunoResearch). The plates were washed and then incubated with Ultra TMB Substrate (Fisher Scientific) for 30 minutes at room temperature. The signal in the wells was detected by an absorbance plate reader at 450 nm wave length to generate a titer curve. The anti-PD-L1 titer is compared to an ELISA performed with serum from the same animal that was obtained prior to immunization.

Rabbits with significant anti-PD-L1 titers were selected for harvest and the generation of monoclonal antibodies.

B-cells from anti-PD-L1 positive rabbits were harvested from the spleen and lymph nodes at week 13 following the initial immunization. The B cells were cultured for one week in 96-well plates to allow their differentiation into plasma cells and for secretion of antibodies. The supernatants from these plasma cell cultures were screened by ELISA as described above for the presence of PD-L1-specific antibodies as shown in FIG. 1.

B cells secreting anti-PD-L1 antibodies were isolated from positive wells using a magnetic capture method. Briefly, streptavidin magnetic beads (ThermoFisher Scientific) were coated with biotin-conjugated human PD-L1 extracellular domain protein. The coated beads were incubated with the cells from an anti-PD-L1 positive well. The bead cell complexes were washed using a magnet to remove any non-specific cells and the bead cell complexes were added directly to a tube containing an RT-PCR master mix.

The light and heavy chain variable sequences were amplified by multiplex RT-PCR using degenerate primers designed to anneal to leader sequences and the constant regions of rabbit IgG and rabbit kappa sequences. Secondary PCR was performed separately for the light and heavy chains using nested primers containing restriction sites. Amplicons from the variable heavy chain PCR were cloned into an expression vector containing human IgG1. Light chain amplicons were cloned into an expression vector containing human IgK. Resulting clones were sequenced and analyzed.

The heavy and light chain expression plasmids generated from each well were transiently co-transfected to produce rabbit/human chimeric antibodies. The resulting supernatants containing the recombinant antibodies were clarified by centrifugation.

Recombinant antibody supernatants were confirmed to contain anti-PD-L1 antibodies using bio-layer interferometry analysis on a ForteBio Octet Red 96 instrument. Anti-human Fc biosensors (Pall ForteBio) were used to capture antibodies in the supernatants. Association to PD-L1 was observed by real-time interferometry by placing the biosensors in wells containing recombinant human PD-L1 extracellular domain protein. Dissociation was measured after transfer of the biosensors into wells containing 10× kinetics buffer (Pall ForteBio). The software provided by the manufacturer was used to analyze the interferometry data.

The ability of the antibody to block the biochemical association between PD-1 and PD-L1 was performed by bio-layer interferometry analysis on a ForteBio Octet Red 96 instrument. Streptavidin biosensors (Pall ForteBio) were used to immobilize biotin-conjugated human PD-L1 extracellular domain. The biosensors were then placed into wells containing the recombinant antibody supernatants. Biosensors were then transferred to wells containing human PD-1 extracellular domain protein. A positive binding signal for PD-1 association indicates an antibody that is unable to block the PD-L1 to PD-1 association, whereas a blocking antibody does not produce a positive binding signal when the biosensor is transferred to PD-1 wells. Control antibody supernatants containing known antibodies that can bind to PD-L1 but are unable to block subsequent PD-1 binding result in a positive binding signal when transferred to the wells containing PD-1. The data was monitored in real time using the software provided by the manufacturer. Example overall data is shown in FIG. 2. Anti-PD-L1 antibodies AB1-AB5 were tested in this assay and the results are shown in FIG. 3.

Humanized forms for anti-PD-L1 antibodies AB1-AB5 were produced and are indicated by an appended "HU" following their original designation. For example, AB1HU is the humanized form of antibody AB1.

Example 2: Binding Affinities of Anti-PD-L1 Antibodies

Figure 4D:
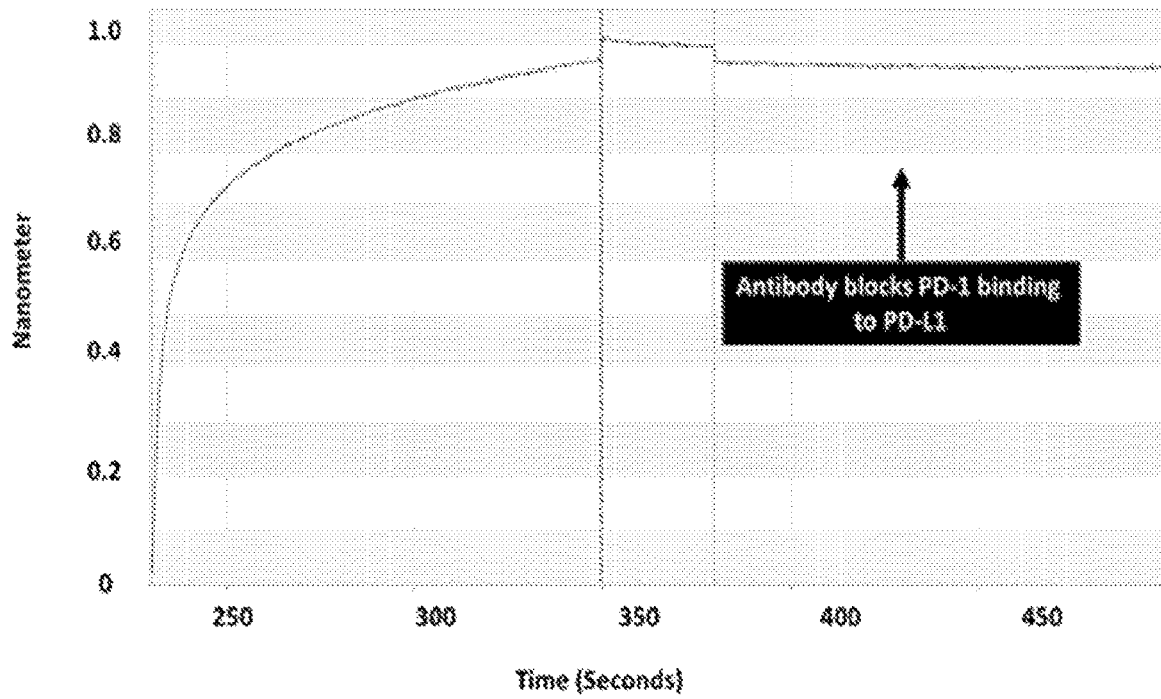
Figure 4E:
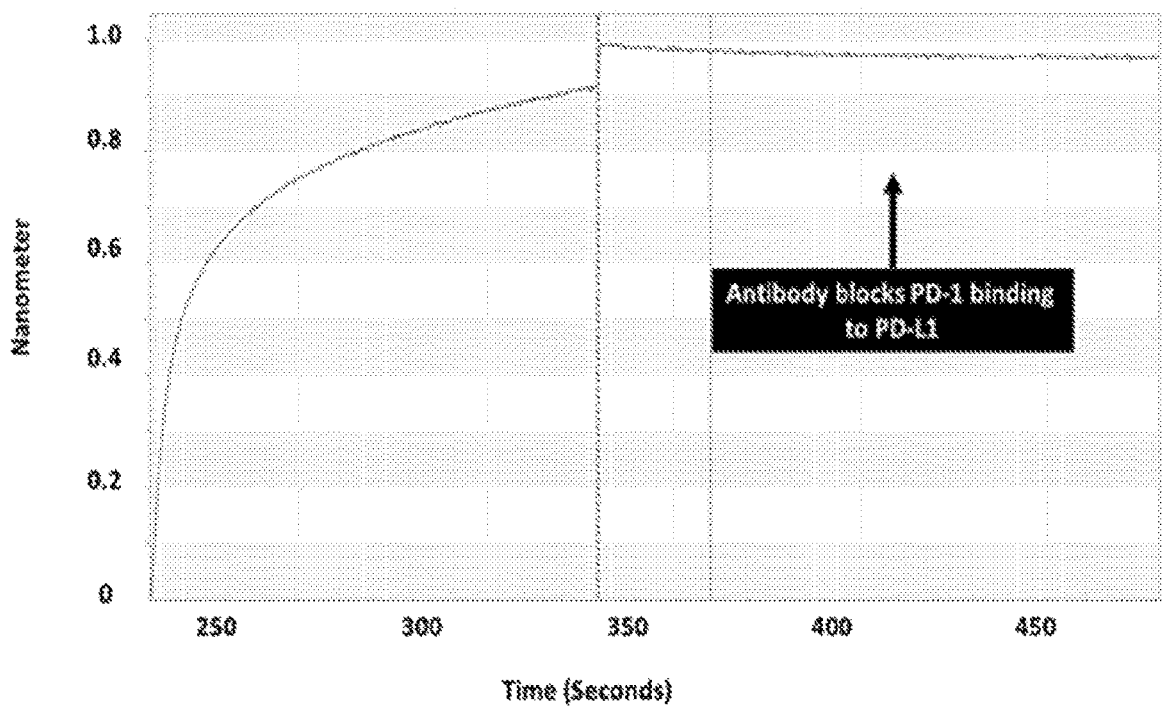

The binding kinetics of selected anti-PD-L1 antibodies AB1-AB5 and AB1HU-AB5HU was determined by bio-layer interferometry analysis on a ForteBio Octet Red 96 instrument. First, purified antibodies were produced by protein A chromatography using HEK-293 transiently-transfected antibody supernatants. This assay was performed by immobilizing the purified antibodies to anti-human Fc biosensors. PD-L1 binding to and dissociation from the biosensors was then observed at various concentrations of PD-L1. Specifically, eight anti-human Fc biosensors were placed into wells containing the same purified antibody for 5 minutes. Biosensors were equilibrated in kinetics buffer (Pall ForteBio) for 1 minute to establish a baseline. Association of PD-L1 was observed by placing the biosensors into wells containing various concentrations of human PD-L1 extracellular domain for 5 minutes. Dissociation was measured after transfer of the biosensors into kinetics buffer and monitoring the interferometry signals for 15 minutes. All steps of the assay were performed at 30° C. with shaking at 1000 RPM. The on and off rates (kon and koff) and the equilibrium binding constant KD were determined using the software provided by the manufacturer and were fit using a 1:1 binding global fit model comprising several of the concentrations tested. Results of the kinetic studies are presented in Table 1 and representative data is shown in FIG. 4.

TABLE 1

| mAb | KD [M] | Kon [1/Ms] | Koff [1/s] |
| --- | --- | --- | --- |
| AB1 | 3.47E−10 | 4.33E+05 | 1.50E−04 |
| AB1HU | 4.22E−10 | 5.68E+05 | 2.39E−04 |
| AB2 | 3.79E−10 | 4.38E+05 | 1.66E−04 |
| AB2HU | 3.66E−10 | 5.53E+05 | 2.03E−04 |
| AB3 | 4.67E−10 | 3.08E+05 | 1.44E−04 |
| AB3HU | 1.81E−09 | 1.86E+05 | 3.37E−04 |
| AB4 | 1.01E−09 | 4.17E+05 | 4.22E−04 |
| AB4HU | 1.70E−09 | 4.51E+05 | 7.66E−04 |
| AB5 | 2.86E−10 | 6.13E+05 | 1.75E−04 |
| AB5HU | 4.01E−10 | 5.83E+05 | 2.34E−04 |

Example 3: Antibodies Binding to Cell-Surface Expressed PD-L1

The human lung cancer cell line H441 was labeled with FVS520 viability dye (BD Biosciences, 1:2000 dilution) for 15 minutes at room temperature. The labeled cells were then diluted in FACS buffer (2% FBS in PBS), added to V-bottom 96-well plates (50,000 cells per well), and incubated with 0-100 nM anti-huPDL1 or negative control isotype-matched or positive control isotype-matched control antibody on ice for 30 minutes. Cells were washed to remove excess primary antibody, then labeled with Alex Fluor 647-conjugated goat anti-human Fc secondary antibody (Jackson Immunoresearch, 1:1600 dilution). Cells were incubated on ice for 20 minutes, then washed with FACS buffer before acquisition on a FACSCalibur flow cytometer equipped with the Cytek AMS plate loader system. FIG. 5 shows the median fluorescence intensity (MFI) on the AF647 channel after gating on live cells. Error bars represent the SEM of duplicate samples.

While the disclosure has been particularly shown and described as referenced to the embodiments thereof, those skilled in the art will understand that the foregoing and other changes in form and detail may be made therein without departing from the spirit and scope. All references cited or referred to in this disclosure are hereby incorporated by reference in their entireties.

```
SEQUENCE LISTING
AB1 CHIMERIC LIGHT CHAIN FULL-LENGTH NUCLEOTIDE SEQUENCE
                                                          SEQ ID NO: 1
GACCCTGTGCTGACCCAGACTCCAGCCTCTGTGGAGGTAGCTGTGGGAGGCACAGTCACCATCAAGTGCCAGGCC

AGTCAGAGCATTAGTTCCCACTTAAACTGGTATCAGCAGAAACCAGGGCAGCCTCCCAAGCTCCTGATCTACAAGG

CATCCACTCTGGCATCTGGGGTCCCATCGCGTTTCAAAGGCAGTGGATCTGGGACAGAGTTCACTCTCACCATCAG

CAGTGTGCAGTGTGACAATGCTGCCACTTATTACTGTCAACAGGGTTATAGTTGGGGTAATGTTGATAATGTTTTC

GGCGGAGGGACCGAGGTGGTGGTCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

AB1 CHIMERIC LIGHT CHAIN VARIABLE LIGHT CHAIN NUCLEOTIDE SEQUENCE
                                                          SEQ ID NO: 2
GACCCTGTGCTGACCCAGACTCCAGCCTCTGTGGAGGTAGCTGTGGGAGGCACAGTCACCATCAAGTGCCAGGCC

AGTCAGAGCATTAGTTCCCACTTAAACTGGTATCAGCAGAAACCAGGGCAGCCTCCCAAGCTCCTGATCTACAAGG

CATCCACTCTGGCATCTGGGGTCCCATCGCGTTTCAAAGGCAGTGGATCTGGGACAGAGTTCACTCTCACCATCAG

CAGTGTGCAGTGTGACAATGCTGCCACTTATTACTGTCAACAGGGTTATAGTTGGGGTAATGTTGATAATGTTTTC

GGCGGAGGGACCGAGGTGGTGGTCAAA

AB1 CHIMERIC LIGHT CHAIN FULL-LENGTH AMINO ACID SEQUENCE. HUMAN KAPPA CONSTANT
DOMAIN IS UNDERLINED
                                                          SEQ ID NO: 3
DPVLTQTPASVEVAVGGTVTIKCQASQSISSHLNWYQQKPGQPPKLLIYKASTLASGVPSRFKGSGSGTEFTLTISSVQCD

NAATYYCQQGYSWGNVDNVFGGGTEVVVKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC
```

AB1 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 4
DPVLTQTPASVEVAVGGTVTIKC<u>QASQSISSHLN</u>WYQQKPGQPPKLLIY<u>KASTLAS</u>GVPSRFKGSGSGTEFTLTISSVQCD

NAATYYC<u>QQGYSWGNVDNV</u>FGGGTEVVVK

AB1 CHIMERIC HEAVY CHAIN FULL-LENGTH NUCLEOTIDE SEQUENCE
SEQ ID NO: 5
CAGGAGCAGCTGGTGGAGTCCGGGGGAGGCCTGGTCCAGCCTGAGGGATCCCTGACACTCACCTGTAAAGCCTC

TGGATTCTCCTTCAGTAGCGGGTACGACATGTGCTGGGTCCGCCGGGCTCCAGGGAAGGGGCTGGAGTGGATCG

CATGCATTGCTGCTGGTAGTGCTGGTATCACTTACGACGCGAACTGGGCGAAAGGCCGATTCACCATCTCCAAAC

CTCGTCGACCACGGTGACTCTACAAATGACCAGTCTGACAGCCGCGGACACGGCCACCTATTTCTGTGCGAGATCG

GCGTTTTCGTTCGACTACGCCATGGACCTCTGGGGCCCAGGGACCCTCGTCACCGTCTCGAGCGCTAGCACCAAGG

GCCCATCGGTCTTCCCCCTGGCACCCTCCTCCAAGAGCACCTCTGGGGGCACAGCGGCCCTGGGCTGCCTGGTCAA

GGACTACTTCCCCGAACCGGTGACGGTGTCGTGGAACTCAGGCGCCCTGACCAGCGGCGTGCACACCTTCCCGGC

TGTCCTACAGTCCTCAGGACTCTACTCCCTCAGCAGCGTGGTGACCGTGCCCTCCAGCAGCTTGGGCACCCAGACC

TACATCTGCAACGTGAATCACAAGCCCAGCAACACCAAGGTGGACAAGAGAGTTGAGCCCAAATCTTGTGACAAA

ACTCACACATGCCCACCGTGCCCAGCACCTGAACTCCTGGGGGGACCGTCAGTCTTCCTCTTCCCCCCAAAACCCAA

GGACACCCTCATGATCTCCCGGACCCCTGAGGTCACATGCGTGGTGGTGGACGTGAGCCACGAAGACCCTGAGGT

CAAGTTCAACTGGTACGTGGACGGCGTGGAGGTGCATAATGCCAAGACAAAGCCGCGGGAGGAGCAGTACAACA

GCACGTACCGTGTGGTCAGCGTCCTCACCGTCCTGCACCAGGACTGGCTGAATGGCAAGGAGTACAAGTGCAAGG

TCTCCAACAAAGCCCTCCCAGCCCCCATCGAGAAAACCATCTCCAAAGCCAAAGGGCAGCCCCGAGAACCACAGG

TGTACACCCTGCCCCCATCCCGGGAGGAGATGACCAAGAACCAGGTCAGCCTGACCTGCCTGGTCAAAGGCTTCT

ATCCCAGCGACATCGCCGTGGAGTGGGAGAGCAATGGGCAGCCGGAGAACAACTACAAGACCACGCCTCCCGTG

CTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGTAAA

AB1 CHIMERIC HEAVY CHAIN VARIABLE HEAVY CHAIN NUCLEOTIDE SEQUENCE
SEQ ID NO: 6
CAGGAGCAGCTGGTGGAGTCCGGGGGAGGCCTGGTCCAGCCTGAGGGATCCCTGACACTCACCTGTAAAGCCTC

TGGATTCTCCTTCAGTAGCGGGTACGACATGTGCTGGGTCCGCCGGGCTCCAGGGAAGGGGCTGGAGTGGATCG

CATGCATTGCTGCTGGTAGTGCTGGTATCACTTACGACGCGAACTGGGCGAAAGGCCGATTCACCATCTCCAAAC

CTCGTCGACCACGGTGACTCTACAAATGACCAGTCTGACAGCCGCGGACACGGCCACCTATTTCTGTGCGAGATCG

GCGTTTTCGTTCGACTACGCCATGGACCTCTGGGGCCCAGGGACCCTCGTCACCGTCTCGAGC

AB1 CHIMERIC HEAVY CHAIN FULL-LENGTH AMINO ACID SEQUENCE. HUMAN GAMMA-1 CONSTANT
DOMAIN IS UNDERLINED
SEQ ID NO: 7
QEQLVESGGGLVQPEGSLTLTCKASGFSFSSGYDMCWVRRAPGKGLEWIACIAAGSAGITYDANWAKGRFTISKTSSTT

VTLQMTSLTAADTATYFCARSAFSFDYAMDLWGPGTLVTVSS<u>ASTKGPSVFPLAPSSKSTSGGTAALGCLVKDYFPEPV</u>

<u>TVSWNSGALTSGVHTFPAVLQSSGLYSLSSVVTVPSSSLGTQTYICNVNHKPSNTKVDKRVEPKSCDKTHTCPPCPAPEL</u>

<u>LGGPSVFLFPPKPKDTLMISRTPEVTCVVVDVSHEDPEVKFNWYVDGVEVHNAKTKPREEQYNSTYRVVSVLTVLHQD</u>

<u>WLNGKEYKCKVSNKALPAPIEKTISKAKGQPREPQVYTLPPSREEMTKNQVSLTCLVKGFYPSDIAVEWESNGQPENNY</u>

<u>KTTPPVLDSDGSFFLYSKLTVDKSRWQQGNVFSCSVMHEALHNHYTQKSLSLSPGK</u>

AB1 CHIMERIC HEAVY CHAIN VARIABLE HEAVY CHAIN AMINO ACID SEQUENCE. COMPLIMENTARITY
DETERMINING REGIONS ARE UNDERLINED
SEQ ID NO: 8
QEQLVESGGGLVQPEGSLTLTCKASGFSFSS<u>GYDMC</u>WVRRAPGKGLEWIA<u>CIAAGSAGITYDANWAKG</u>RFTISKTSSTT

VTLQMTSLTAADTATYFCAR<u>SAFSFDYAMDL</u>WGPGTLVTVSS

AB1HU HUMANIZED LIGHT CHAIN FULL-LENGTH NUCLEOTIDE SEQUENCE
SEQ ID NO: 9
GACATCCAGATGACCCAGTCTCCTTCCACCCTGTCTGCATCTGTAGGAGACAGAGTCACCATCACTTGCCAGGCCA

GTCAGAGCATTAGTTCCCACTTAAACTGGTATCAGCAGAAACCAGGGAAAGCCCCTAAGCTCCTGATCTATAAGGC

ATCCACTCTGGCATCTGGGGTCCCATCAAGGTTCAGCGGCAGTGGATCTGGGACAGAATTTACTCTCACCATCAGC

AGCCTGCAGCCTGATGATTTTGCAACTTATTACTGCCAACAGGGTTATAGTTGGGGTAATGTTGATAATGTTTTCG

GCGGAGGGACCAAGGTGGAGATCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

AB1HU HUMANIZED LIGHT CHAIN VARIABLE LIGHT CHAIN NUCLEOTIDE SEQUENCE
SEQ ID NO: 10
GACATCCAGATGACCCAGTCTCCTTCCACCCTGTCTGCATCTGTAGGAGACAGAGTCACCATCACTTGCCAGGCCA

GTCAGAGCATTAGTTCCCACTTAAACTGGTATCAGCAGAAACCAGGGAAAGCCCCTAAGCTCCTGATCTATAAGGC

ATCCACTCTGGCATCTGGGGTCCCATCAAGGTTCAGCGGCAGTGGATCTGGGACAGAATTTACTCTCACCATCAGC

AGCCTGCAGCCTGATGATTTTGCAACTTATTACTGCCAACAGGGTTATAGTTGGGGTAATGTTGATAATGTTTTCG

GCGGAGGGACCAAGGTGGAGATCAAA

AB1HU HUMANIZED LIGHT CHAIN FULL-LENGTH AMINO ACID SEQUENCE. HUMAN KAPPA CONSTANT
DOMAIN IS UNDERLINED
SEQ ID NO: 11
DIQMTQSPSTLSASVGDRVTITCQASQSISSHLNWYQQKPGKAPKLLIYKASTLASGVPSRFSGSGSGTEFTLTISSLQPD

DFATYYCQQGYSWGNVDNVFGGGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

AB1HU HUMANIZED LIGHT CHAIN VARIABLE LIGHT CHAIN AMINO ACID SEQUENCE.
COMPLEMENTARITY DETERMINING REGIONS ARE UNDERLINED
SEQ ID NO: 12
DIQMTQSPSTLSASVGDRVTITCQASQSISSHLNWYQQKPGKAPKLLIYKASTLASGVPSRFSGSGSGTEFTLTISSLQPD

DFATYYCQQGYSWGNVDNVFGGGTKVEIK

AB1HU HUMANIZED HEAVY CHAIN FULL-LENGTH NUCLEOTIDE SEQUENCE
SEQ ID NO: 13
GAGGTGCAGCTGTTGGAGTCTGGGGGAGGCTTGGTACAGCCTGGGGGGTCCCTGAGACTCTCCTGTGCAGCCTCT

GGATTCTCCTTCAGTAGCGGGTACGACATGTGCTGGGTCCGCCAGGCTCCAGGGAAGGGGCTGGAGTGGATCGC

ATGCATTGCTGCTGGTAGTGCTGGTATCACTTACGACGCGAACTGGGCGAAAGGCCGGTTCACCATCTCCAGAGA

CAATTCCAAGAACACGCTGTATCTGCAAATGAACAGCCTGAGAGCCGAGGACACGGCCGTATATTACTGTGCGAG

ATCGGCGTTTTCGTTCGACTACGCCATGGACCTCTGGGGCCAGGGAACCCTGGTCACCGTCTCGAGCGCTAGCACC

AAGGGCCCATCGGTCTTCCCCCTGGCACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGCCCTGACCAGCGGCGTGCACACCTTC

CCGGCTGTCCTACAGTCCTCAGGACTCTACTCCCTCAGCAGCGTGGTGACCGTGCCCTCCAGCAGCTTGGGCACCC

AGACCTACATCTGCAACGTGAATCACAAGCCCAGCAACACCAAGGTGGACAAGAGAGTTGAGCCCAAATCTTGTG

ACAAAACTCACACATGCCCACCGTGCCCAGCACCTGAACTCCTGGGGGGACCGTCAGTCTTCCTCTTCCCCCCAAA

ACCCAAGGACACCCTCATGATCTCCCGGACCCCTGAGGTCACATGCGTGGTGGTGGACGTGAGCCACGAAGACCC

TGAGGTCAAGTTCAACTGGTACGTGGACGGCGTGGAGGTGCATAATGCCAAGACAAAGCCGCGGGAGGAGCAG

TACAACAGCACGTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGAGGAGATGACCAAGAACCAGGTCAGCCTGACCTGCCTGGTCAAA

```
GGCTTCTATCCCAGCGACATCGCCGTGGAGTGGGAGAGCAATGGGCAGCCGGAGAACAACTACAAGACCACGCC

TCCCGTGCTGGACTCCGACGGCTCCTTCTTCCTCTATAGCAAGCTCACCGTGGACAAGAGCAGGTGGCAGCAGGG

GAACGTCTTCTCATGCTCCGTGATGCATGAGGCTCTGCACAACCACTACACGCAGAAGAGCCTCTCCCTGTCTCCG

GGTAAA
```

AB1HU HUMANIZED HEAVY CHAIN VARIABLE HEAVY CHAIN NUCLEOTIDE SEQUENCE
SEQ ID NO: 14
```
GAGGTGCAGCTGTTGGAGTCTGGGGGAGGCTTGGTACAGCCTGGGGGGTCCCTGAGACTCTCCTGTGCAGCCTCT

GGATTCTCCTTCAGTAGCGGGTACGACATGTGCTGGGTCCGCCAGGCTCCAGGGAAGGGGCTGGAGTGGATCGC

ATGCATTGCTGCTGGTAGTGCTGGTATCACTTACGACGCGAACTGGGCGAAAGGCCGGTTCACCATCTCCAGAGA

CAATTCCAAGAACACGCTGTATCTGCAAATGAACAGCCTGAGAGCCGAGGACACGGCCGTATATTACTGTGCGAG

ATCGGCGTTTTCGTTCGACTACGCCATGGACCTCTGGGGCCAGGGAACCCTGGTCACCGTCTCGAGC
```

AB1HU HUMANIZED HEAVY CHAIN FULL-LENGTH AMINO ACID SEQUENCE. HUMAN GAMMA1 CONSTANT DOMAIN IS UNDERLINED
SEQ ID NO: 15
```
EVQLLESGGGLVQPGGSLRLSCAASGFSFSSGYDMCWVRQAPGKGLEWIACIAAGSAGITYDANWAKGRFTISRDNSK

NTLYLQMNSLRAEDTAVYYCARSAFSFDYAMDLWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKRVEPKSCDKTHTCPPCPAP

ELLGGPSVFLFPPKPKDTLMISRTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPGK
```

AB1HU HUMANIZED HEAVY CHAIN VARIABLE HEAVY CHAIN AMINO ACID SEQUENCE. COMPLEMENTARITY DETERMINING REGIONS ARE UNDERLINED
SEQ ID NO: 16
```
EVQLLESGGGLVQPGGSLRLSCAASGFSFSSGYDMCWVRQAPGKGLEWIACIAAGSAGITYDANWAKGRFTISRDNSK

NTLYLQMNSLRAEDTAVYYCARSAFSFDYAMDLWGQGTLVTVSS
```

AB2 CHIMERIC LIGHT CHAIN FULL-LENGTH NUCLEOTIDE SEQUENCE
SEQ ID NO: 17
```
GCCTATGATATGACCCAGACTCCAGCCTCCGTGTCTGCAGCTGTGGGAGGCACAGTCACCATCAATTGCCAGGCCA

GTGAGAGCATTAGTAGCTTCTTATCCTGGTATCAGCAGAAACCAGGGCAGCGTCCCAGGCTCCTGATCTTTTCTGC

ATCCACTCTGGCATCTGGGGTCCCATCGCGGTTCAAAGGCAGTGGATCTGGGACAGAGTTCACTCTCACCATCAGC

GGCGTGGAGTGTGCCGATGCTGCCACTTATTATTGTCAACAGGGTTATAGTAAAAGTAATGTGGATAATGCTTTCG

GCGGAGGGACCGAGGTGGTGGTCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT
```

AB2 CHIMERIC LIGHT CHAIN VARIABLE LIGHT CHAIN NUCLEOTIDE SEQUENCE
SEQ ID NO: 18
```
GCCTATGATATGACCCAGACTCCAGCCTCCGTGTCTGCAGCTGTGGGAGGCACAGTCACCATCAATTGCCAGGCCA

GTGAGAGCATTAGTAGCTTCTTATCCTGGTATCAGCAGAAACCAGGGCAGCGTCCCAGGCTCCTGATCTTTTCTGC

ATCCACTCTGGCATCTGGGGTCCCATCGCGGTTCAAAGGCAGTGGATCTGGGACAGAGTTCACTCTCACCATCAGC

GGCGTGGAGTGTGCCGATGCTGCCACTTATTATTGTCAACAGGGTTATAGTAAAAGTAATGTGGATAATGCTTTCG

GCGGAGGGACCGAGGTGGTGGTCAAA
```

AB2 CHIMERIC LIGHT CHAIN FULL-LENGTH AMINO ACID SEQUENCE. HUMAN KAPPA CONSTANT
DOMAIN IS UNDERLINED
SEQ ID NO: 19
AYDMTQTPASVSAAVGGTVTINCQASESISSFLSWYQQKPGQRPRLLIFSASTLASGVPSRFKGSGSGTEFTLTISGVECA

DAATYYCQQGYSKSNVDNAFGGGTEVVVK<u>RTVAAPSVFIFPPSDEQLKSGTASVVCLLNNFYPREAKVQWKVDNALQ</u>

<u>SGNSQESVTEQDSKDSTYSLSSTLTLSKADYEKHKVYACEVTHQGLSSPVTKSFNRGEC</u>

AB2 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 20
AYDMTQTPASVSAAVGGTVTINC<u>QASESISSFLS</u>WYQQKPGQRPRLLIF<u>SASTLAS</u>GVPSRFKGSGSGTEFTLTISGVECA

DAATYYC<u>QQGYSKSNVDN</u>AFGGGTEVVVK

AB2 CHIMERIC HEAVY CHAIN FULL-LENGTH NUCLEOTIDE SEQUENCE
SEQ ID NO: 21
CAGTCGCTGGAGGAGTCCGGGGGTCGCCTGGTCACGCCTGGGACACCCCTGACACTCACCTGTACAACTTCCGGA

ATCGACCTTAGTACCTACGACATGATCTGGGTCCGCCAGGCTCCAGGGAAGGGGCTGGAATACATCGGAATCATT

AGTTATGTTGGTAACACATACTACGCGAGCTGGGCGAAAGGCCGATTCACCCTCTCCAAAACCTCGACCACGGTG

GATCTGAGAATCACCAGTCCGACAACCGAGGACACGGCCACCTATTTCTGTGCCAGGGATTTTATTAGTGGTTCCC

ACTTGTGGGGCCCGGGCACCCTGGTCACCGTCTCGAGCGCTAGCACCAAGGGCCCATCGGTCTTCCCCCTGGCACC

CTCCTCCAAGAGCACCTCTGGGGGCACAGCGGCCCTGGGCTGCCTGGTCAAGGACTACTTCCCCGAACCGGTGAC

GGTGTCGTGGAACTCAGGCGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCTGCAACGTGAATCACAAGC

CCAGCAACACCAAGGTGGACAAGAGAGTTGAGCCCAAATCTTGTGACAAAACTCACACATGCCCACCGTGCCCAG

CACCTGAACTCCTGGGGGGACCGTCAGTCTTCCTCTTCCCCCCAAAACCCAAGGACACCCTCATGATCTCCCGGACC

CCTGAGGTCACATGCGTGGTGGTGGACGTGAGCCACGAAGACCCTGAGGTCAAGTTCAACTGGTACGTGGACGG

CGTGGAGGTGCATAATGCCAAGACAAAGCCGCGGGAGGAGCAGTACAACAGCACGTACCGTGTGGTCAGCGTCC

TCACCGTCCTGCACCAGGACTGGCTGAATGGCAAGGAGTACAAGTGCAAGGTCTCCAACAAAGCCCTCCCAGCCC

CCATCGAGAAAACCATCTCCAAAGCCAAAGGGCAGCCCCGAGAACCACAGGTGTACACCCTGCCCCCATCCCGGG

AGGAGATGACCAAGAACCAGGTCAGCCTGACCTGCCTGGTCAAAGGCTTCTATCCCAGCGACATCGCCGTGGAGT

GGGAGAGCAATGGGCAGCCGGAGAACAACTACAAGACCACGCCTCCCGTGCTGGACTCCGACGGCTCCTTCTTCC

TCTATAGCAAGCTCACCGTGGACAAGAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

AB2 CHIMERIC HEAVY CHAIN VARIABLE HEAVY CHAIN NUCLEOTIDE SEQUENCE
SEQ ID NO: 22
CAGTCGCTGGAGGAGTCCGGGGGTCGCCTGGTCACGCCTGGGACACCCCTGACACTCACCTGTACAACTTCCGGA

ATCGACCTTAGTACCTACGACATGATCTGGGTCCGCCAGGCTCCAGGGAAGGGGCTGGAATACATCGGAATCATT

AGTTATGTTGGTAACACATACTACGCGAGCTGGGCGAAAGGCCGATTCACCCTCTCCAAAACCTCGACCACGGTG

GATCTGAGAATCACCAGTCCGACAACCGAGGACACGGCCACCTATTTCTGTGCCAGGGATTTTATTAGTGGTTCCC

ACTTGTGGGGCCCGGGCACCCTGGTCACCGTCTCGAGC

AB2 CHIMERIC HEAVY CHAIN FULL-LENGTH AMINO ACID SEQUENCE. HUMAN GAMMA-1 CONSTANT
DOMAIN IS UNDERLINED
SEQ ID NO: 23
QSLEESGGRLVTPGTPLTLTCTTSGIDLSTYDMIWVRQAPGKGLEYIGIISYVGNTYYASWAKGRFTLSKTSTTVDLRITSP

TTEDTATYFCARDFISGSHLWGPGTLVTVS<u>SASTKGPSVFPLAPSSKSTSGGTAALGCLVKDYFPEPVTVSWNSGALTSG</u>

<u>VHTFPAVLQSSGLYSLSSVVTVPSSSLGTQTYICNVNHKPSNTKVDKRVEPKSCDKTHTCPPCPAPELLGGPSVFLFPPKP</u>

<u>KDTLMISRTPEVTCVVVDVSHEDPEVKFNWYVDGVEVHNAKTKPREEQYNSTYRVVSVLTVLHQDWLNGKEYKCKVS</u>

<u>NKALPAPIEKTISKAKGQPREPQVYTLPPSREEMTKNQVSLTCLVKGFYPSDIAVEWESNGQPENNYKTTPPVLDSDGSF</u>

<u>FLYSKLTVDKSRWQQGNVFSCSVMHEALHNHYTQKSLSLSPGK</u>

AB2 CHIMERIC HEAVY CHAIN VARIABLE HEAVY CHAIN AMINO ACID SEQUENCE. COMPLIMENTARITY
DETERMINING REGIONS ARE UNDERLINED
SEQ ID NO: 24
QSLEESGGRLVTPGTPLTLTCTTSGIDLS<u>TYDMI</u>WVRQAPGKGLEYIGI<u>ISYVGNTYYASWAKG</u>RFTLSKTSTTVDLRITSP

TTEDTATYFCAR<u>DFISGSHL</u>WGPGTLVTVSS

AB2HU HUMANIZED LIGHT CHAIN FULL-LENGTH NUCLEOTIDE SEQUENCE
SEQ ID NO: 25
GCCTATGATATGACCCAGTCTCCATCTTCCGTGTCTGCATCTGTAGGAGACAGAGTCACCATCAATTGTCAGGCCA

GTGAGAGCATTAGTAGCTTCTTATCCTGGTATCAGCAGAAACCAGGGAAAGCCCCTAAGCTCCTGATCTTTTCTGC

ATCCACTCTGGCATCTGGGGTCCCATCAAGGTTCAGCGGCAGTGGATCTGGGACAGATTTCACTCTCACCATCAGC

AGCCTGCAGCCTGAAGATTTTGCAACTTACTATTGTCAACAGGGTTATAGTAAAAGTAATGTGGATAATGCTTTCG

GCGGAGGGACCAAGGTGGAGATCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

AB2HU HUMANIZED LIGHT CHAIN VARIABLE LIGHT CHAIN NUCLEOTIDE SEQUENCE
SEQ ID NO: 26
GCCTATGATATGACCCAGTCTCCATCTTCCGTGTCTGCATCTGTAGGAGACAGAGTCACCATCAATTGTCAGGCCA

GTGAGAGCATTAGTAGCTTCTTATCCTGGTATCAGCAGAAACCAGGGAAAGCCCCTAAGCTCCTGATCTTTTCTGC

ATCCACTCTGGCATCTGGGGTCCCATCAAGGTTCAGCGGCAGTGGATCTGGGACAGATTTCACTCTCACCATCAGC

AGCCTGCAGCCTGAAGATTTTGCAACTTACTATTGTCAACAGGGTTATAGTAAAAGTAATGTGGATAATGCTTTCG

GCGGAGGGACCAAGGTGGAGATCAAA

AB2HU HUMANIZED LIGHT CHAIN FULL-LENGTH AMINO ACID SEQUENCE. HUMAN KAPPA CONSTANT
DOMAIN IS UNDERLINED
SEQ ID NO: 27
AYDMTQSPSSVSASVGDRVTINCQASESISSFLSWYQQKPGKAPKLLIFSASTLASGVPSRFSGSGSGTDFTLTISSLQPED

FATYYCQQGYSKSNVDNAFGGGTKVEIK<u>RTVAAPSVFIFPPSDEQLKSGTASVVCLLNNFYPREAKVQWKVDNALQSG</u>

<u>NSQESVTEQDSKDSTYSLSSTLTLSKADYEKHKVYACEVTHQGLSSPVTKSFNRGEC</u>

AB2HU HUMANIZED LIGHT CHAIN VARIABLE LIGHT CHAIN AMINO ACID SEQUENCE.
COMPLEMENTARITY DETERMINING REGIONS ARE UNDERLINED
SEQ ID NO: 28
AYDMTQSPSSVSASVGDRVTINC<u>QASESISSFLS</u>WYQQKPGKAPKLLIF<u>SASTLAS</u>GVPSRFSGSGSGTDFTLTISSLQPED

FATYYC<u>QQGYSKSNVDNA</u>FGGGTKVEIK

AB2HU HUMANIZED HEAVY CHAIN FULL-LENGTH NUCLEOTIDE SEQUENCE
SEQ ID NO: 29
CAGGTGCAGCTGGTGGAGTCTGGGGGAGGCCTGGTCCAGCCTGGGGGCTCCCTGAGACTCTCCTGTACAACTTCT

GGAATCGACCTTAGTACCTACGACATGATCTGGGTCCGCCAGGCTCCAGGCAAGGGGCTAGAGTGGGTGGGAAT

CATTAGTTATGTTGGTAACACATACTACGCGAGCTGGGCGAAAGGCCGATTCACCCTCTCCAAAACCAAGAACACG

GTGTATCTGCAAATGAACAGCCTGAGAGCTGAGGACACGGCTGTGTATTACTGTGCGAGAGATTTTATTAGTGGT

TCCCACTTGTGGGGCCAGGGAACCCTGGTCACCGTCTCGAGCGCTAGCACCAAGGGCCCATCGGTCTTCCCCCTGG

CACCCTCCTCCAAGAGCACCTCTGGGGGCACAGCGGCCCTGGGCTGCCTGGTCAAGGACTACTTCCCCGAACCGG

TGACGGTGTCGTGGAACTCAGGCGCCCTGACCAGCGGCGTGCACACCTTCCCGGCTGTCCTACAGTCCTCAGGACT

CTACTCCCTCAGCAGCGTGGTGACCGTGCCCTCCAGCAGCTTGGGCACCCAGACCTACATCTGCAACGTGAATCAC

AAGCCCAGCAACACCAAGGTGGACAAGAGAGTTGAGCCCAAATCTTGTGACAAAACTCACACATGCCCACCGTGC

CCAGCACCTGAAGCCGCGGGGGCACCGTCAGTCTTCCTCTTCCCCCCAAAACCCAAGGACACCCTCATGATCTCCC

GGACCCCTGAGGTCACATGCGTGGTGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTACAACAGCACGTACCGTGTGGTCA

```
GCGTCCTCACCGTCCTGCACCAGGACTGGCTGAATGGCAAGGAGTACAAGTGCGCGGTCTCCAACAAAGCCCTCC

CAGCCCCCATCGAGAAAACCATCTCCAAAGCCAAAGGGCAGCCCCGAGAACCACAGGTGTACACCCTGCCCCCAT

CCCGGGATGAGCTGACCAAGAACCAGGTCAGCCTGACCTGCCTGGTCAAAGGCTTCTATCCCAGCGACATCGCCG

TGGAGTGGGAGAGCAATGGGCAGCCGGAGAACAACTACAAGACCACGCCTCCCGTGCTGGACTCCGACGGCTCC

TTCTTCCTCTATAGCAAGCTCACCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGT
```

AB2HU HUMANIZED HEAVY CHAIN VARIABLE HEAVY CHAIN NUCLEOTIDE SEQUENCE

SEQ ID NO: 30

```
CAGGTGCAGCTGGTGGAGTCTGGGGGAGGCCTGGTCCAGCCTGGGGGCTCCCTGAGACTCTCCTGTACAACTTCT

GGAATCGACCTTAGTACCTACGACATGATCTGGGTCCGCCAGGCTCCAGGCAAGGGGCTAGAGTGGGTGGGAAT

CATTAGTTATGTTGGTAACACATACTACGCGAGCTGGGCGAAAGGCCGATTCACCCTCTCCAAAACCAAGAACACG

GTGTATCTGCAAATGAACAGCCTGAGAGCTGAGGACACGGCTGTGTATTACTGTGCGAGAGATTTTATTAGTGGT

TCCCACTTGTGGGGCCAGGGAACCCTGGTCACCGTCTCGAGC
```

AB2HU HUMANIZED HEAVY CHAIN FULL-LENGTH AMINO ACID SEQUENCE. HUMAN GAMMA1
CONSTANT DOMAIN IS UNDERLINED

SEQ ID NO: 31

QVQLVESGGGLVQPGGSLRLSCTTSGIDLSTYDMIWVRQAPGKGLEWVGIISYVGNTYYASWAKGRFTLSKTKNTVYL

QMNSLRAEDTAVYYCARDFISGSHLWGQGTLVTVSS<u>ASTKGPSVFPLAPSSKSTSGGTAALGCLVKDYFPEPVTVSWNS</u>

<u>GALTSGVHTFPAVLQSSGLYSLSSVVTVPSSSLGTQTYICNVNHKPSNTKVDKRVEPKSCDKTHTCPPCPAPEAAGAPSV</u>

<u>FLFPPKPKDTLMISRTPEVTCVVVDVSHEDPEVKFNWYVDGVEVHNAKTKPREEQYNSTYRVVSVLTVLHQDWLNGKE</u>

<u>YKCAVSNKALPAPIEKTISKAKGQPREPQVYTLPPSRDELTKNQVSLTCLVKGFYPSDIAVEWESNGQPENNYKTTPPVL</u>

<u>DSDGSFFLYSKLTVDKSRWQQGNVFSCSVMHEALHNHYTQKSLSLSPG</u>

AB2HU HUMANIZED HEAVY CHAIN VARIABLE HEAVY CHAIN AMINO ACID SEQUENCE.
COMPLEMENTARITY DETERMINING REGIONS ARE UNDERLINED

SEQ ID NO: 32

QVQLVESGGGLVQPGGSLRLSCTTSGIDLS<u>TYDMI</u>WVRQAPGKGLEWVG<u>IISYVGNTYYASWAKG</u>RFTLSKTKNTVYL

QMNSLRAEDTAVYYCAR<u>DFISGSHL</u>WGQGTLVTVSS

AB3 CHIMERIC LIGHT CHAIN FULL-LENGTH NUCLEOTIDE SEQUENCE

SEQ ID NO: 33

```
GCCGTGCTGACCCAGACTCCATCTCCCGTGTCTGCAGCTGTGGGAGGCACAGTCAGCATCAGTTGCCAGTCCAGTC

AGAGTGTTTATAATGGCTACTGGTTATCCTGGTATCAGCAGAAGCCAGGGCAGCCTCCCAAGCTCCTGATCTATGG

TGCATCCACTCTGGCATCTGGGGTCCCATCGCGGTTCAAAGGCAGTGGATCTGGGACACAGTTCACTCTCACCATC

AACGACGTGCAGTGTGACGATGCTGCCACTTACTACTGTCTAGGCAGTTATACTAGTAGTACTGAGAATTCTTTCG

GCGGAGGGACCGAGGTGGTGGTCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT
```

AB3 CHIMERIC LIGHT CHAIN VARIABLE LIGHT CHAIN NUCLEOTIDE SEQUENCE

SEQ ID NO: 34

```
GCCGTGCTGACCCAGACTCCATCTCCCGTGTCTGCAGCTGTGGGAGGCACAGTCAGCATCAGTTGCCAGTCCAGTC

AGAGTGTTTATAATGGCTACTGGTTATCCTGGTATCAGCAGAAGCCAGGGCAGCCTCCCAAGCTCCTGATCTATGG

TGCATCCACTCTGGCATCTGGGGTCCCATCGCGGTTCAAAGGCAGTGGATCTGGGACACAGTTCACTCTCACCATC

AACGACGTGCAGTGTGACGATGCTGCCACTTACTACTGTCTAGGCAGTTATACTAGTAGTACTGAGAATTCTTTCG

GCGGAGGGACCGAGGTGGTGGTCAAA
```

AB3 CHIMERIC LIGHT CHAIN FULL-LENGTH AMINO ACID SEQUENCE. HUMAN KAPPA CONSTANT
DOMAIN IS UNDERLINED

SEQ ID NO: 35

AVLTQTPSPVSAAVGGTVSISCQSSQSVYNGYWLSWYQQKPGQPPKLLIYGASTLASGVPSRFKGSGSGTQFTLTINDV

QCDDAATYYCLGSYTSSTENSFGGGTEVVVKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

AB3 CHIMERIC LIGHT CHAIN VARIABLE LIGHT CHAIN AMINO ACID SEQUENCE. COMPIMENTARITY
DETERMINING REGIONS ARE UNDERLINED

SEQ ID NO: 36

AVLTQTPSPVSAAVGGTVSISCQSSQSVYNGYWLSWYQQKPGQPPKLLIYGASTLASGVPSRFKGSGSGTQFTLTINDV

QCDDAATYYCLGSYTSSTENSFGGGTEVVVK

AB3 CHIMERIC HEAVY CHAIN FULL-LENGTH NUCLEOTIDE SEQUENCE

SEQ ID NO: 37

CAGGAGCAGCTGGAGGAGTCCGGGGGAGGCCTGGTCACGCCTGGAGGAACCCTGACACTCACCTGCACAGTCTC

TGGATTCTCCCTCAGTAGCTACTGGATGAGCTGGGTCCGCCAGGCTCCAGGGAAGGGGCTGGAGTGGATCGGAG

TCATTGATACTAATGTTTATATATACTACGCGAACTGGGCAAAAGGCCGATTCACCATCTCCAAAACCTCGACCACG

GTGGATCTGAAGATCACCAGTCCGACAACCGAGGACACGGCCACCTATTTCTGTGCCAGATATGTGGGTAATAAT

GATGATTATATTAACTTGTGGGGCCCGGGCACCCTGGTCACCGTCTCGAGCGCTAGCACCAAGGGCCCATCGGTCT

TCCCCCTGGCACCCTCCTCCAAGAGCACCTCTGGGGGCACAGCGGCCCTGGGCTGCCTGGTCAAGGACTACTTCCC

CGAACCGGTGACGGTGTCGTGGAACTCAGGCGCCCTGACCAGCGGCGTGCACACCTTCCCGGCTGTCCTACAGTC

CTCAGGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAGAGTTGAGCCCAAATCTTGTGACAAAACTCACACATGC

CCACCGTGCCCAGCACCTGAACTCCTGGGGGGACCGTCAGTCTTCCTCTTCCCCCCAAAACCCAAGGACACCCTCA

TGATCTCCCGGACCCCTGAGGTCACATGCGTGGTGGTGGACGTGAGCCACGAAGACCCTGAGGTCAAGTTCAACT

GGTACGTGGACGGCGTGGAGGTGCATAATGCCAAGACAAAGCCGCGGGAGGAGCAGTACAACAGCACGTACCG

TGTGGTCAGCGTCCTCACCGTCCTGCACCAGGACTGGCTGAATGGCAAGGAGTACAAGTGCAAGGTCTCCAACAA

AGCCCTCCCAGCCCCCATCGAGAAAACCATCTCCAAAGCCAAAGGGCAGCCCCGAGAACCACAGGTGTACACCCT

GCCCCCATCCCGGGAGGAGATGACCAAGAACCAGGTCAGCCTGACCTGCCTGGTCAAAGGCTTCTATCCCAGCGA

CATCGCCGTGGAGTGGGAGAGCAATGGGCAGCCGGAGAACAACTACAAGACCACGCCTCCCGTGCTGGACTCCG

ACGGCTCCTTCTTCCTCTATAGCAAGCTCACCGTGGACAAGAGCAGGTGGCAGCAGGGGAACGTCTTCTCATGCTC

CGTGATGCATGAGGCTCTGCACAACCACTACACGCAGAAGAGCCTCTCCCTGTCTCCGGGTAAA

AB3 CHIMERIC HEAVY CHAIN VARIABLE HEAVY CHAIN NUCLEOTIDE SEQUENCE

SEQ ID NO: 38

CAGGAGCAGCTGGAGGAGTCCGGGGGAGGCCTGGTCACGCCTGGAGGAACCCTGACACTCACCTGCACAGTCTC

TGGATTCTCCCTCAGTAGCTACTGGATGAGCTGGGTCCGCCAGGCTCCAGGGAAGGGGCTGGAGTGGATCGGAG

TCATTGATACTAATGTTTATATATACTACGCGAACTGGGCAAAAGGCCGATTCACCATCTCCAAAACCTCGACCACG

GTGGATCTGAAGATCACCAGTCCGACAACCGAGGACACGGCCACCTATTTCTGTGCCAGATATGTGGGTAATAAT

GATGATTATATTAACTTGTGGGGCCCGGGCACCCTGGTCACCGTCTCGAGC

AB3 CHIMERIC HEAVY CHAIN FULL-LENGTH AMINO ACID SEQUENCE. HUMAN GAMMA-1 CONSTANT
DOMAIN IS UNDERLINED

SEQ ID NO: 39

QEQLEESGGGLVTPGGTLTLTCTVSGFSLSSYWMSWVRQAPGKGLEWIGVIDTNVYIYYANWAKGRFTISKTSTTVDLK

ITSPTTEDTATYFCARYVGNNDDYINLWGPGTLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSNTKVDKRVEPKSCDKTHTCPPCPAPELLGGPSV

FLFPPKPKDTLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

AB3 CHIMERIC HEAVY CHAIN VARIABLE HEAVY CHAIN AMINO ACID SEQUENCE. COMPLIMENTARITY
DETERMINING REGIONS ARE UNDERLINED
SEQ ID NO: 40
QEQLEESGGGLVTPGGTLTLTCTVSGFSLS<u>SYWMS</u>WVRQAPGKGLEWIG<u>VIDTNVYIYYANWAKG</u>RFTISKTSTTVDLK

ITSPTTEDTATYFCARY<u>VGNNDDYINL</u>WGPGTLVTVSS

AB3HU HUMANIZED LIGHT CHAIN FULL-LENGTH NUCLEOTIDE SEQUENCE
SEQ ID NO: 41
GACATCCAGATGACCCAGTCTCCTTCCACCCTGTCTGCATCTGTAGGAGACAGAGTCACCATCACTTGCCAGTCCA

GTCAGAGTGTTTATAATGGCTACTGGTTATCCTGGTATCAGCAGAAACCAGGGAAAGCCCCTAAGCTCCTGATCTA

TGGTGCATCCACTCTGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCCTAGGCAGTTATACTAGTAGTACTGAGAACTCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

AB3HU HUMANIZED LIGHT CHAIN VARIABLE LIGHT CHAIN NUCLEOTIDE SEQUENCE
SEQ ID NO: 42
GACATCCAGATGACCCAGTCTCCTTCCACCCTGTCTGCATCTGTAGGAGACAGAGTCACCATCACTTGCCAGTCCA

GTCAGAGTGTTTATAATGGCTACTGGTTATCCTGGTATCAGCAGAAACCAGGGAAAGCCCCTAAGCTCCTGATCTA

TGGTGCATCCACTCTGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCCTAGGCAGTTATACTAGTAGTACTGAGAACTCTTT

CGGCGGAGGGACCAAGGTGGAGATCAAA

AB3HU HUMANIZED LIGHT CHAIN FULL-LENGTH AMINO ACID SEQUENCE. HUMAN KAPPA CONSTANT
DOMAIN IS UNDERLINED
SEQ ID NO: 43
DIQMTQSPSTLSASVGDRVTITCQSSQSVYNGYWLSWYQQKPGKAPKLLIYGASTLASGVPSRFSGSGSGTEFTLTISSL

QPDDFATYYCLGSYTSSTENSFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

AB3HU HUMANIZED LIGHT CHAIN VARIABLE LIGHT CHAIN AMINO ACID SEQUENCE.
COMPLEMENTARITY DETERMINING REGIONS ARE UNDERLINED
SEQ ID NO: 44
DIQMTQSPSTLSASVGDRVTITC<u>QSSQSVYNGYWLS</u>WYQQKPGKAPKLLIY<u>GASTLAS</u>GVPSRFSGSGSGTEFTLTISSL

QPDDFATYYC<u>LGSYTSSTENS</u>FGGGTKVEIK

AB3HU HUMANIZED HEAVY CHAIN FULL-LENGTH NUCLEOTIDE SEQUENCE
SEQ ID NO: 45
GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTGGATGAGCTGGGTCCGCCAGGCTCCAGGGAAGGGGCTGGAGTGGATCGGAG

TCATTGATACTAATGTTTATATATACTACGCGAACTGGGCAAAAGGCAGATTCACCATCTCCAGAGACAATTCCAA

GAACACGCTGTATCTTCAAATGAACAGCCTGAGAGCCGAGGACACGGCTGTGTATTACTGTGCGAGATATGTGGG

TAATAATGATGATTATATTAACTTGTGGGGCCAGGGAACCCTGGTCACCGTCTCGAGCGCTAGCACCAAGGGCCC

ATCGGTCTTCCCCCTGGCACCCTCCTCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCACACCTTCCCGGCTGTC

CTACAGTCCTCAGGACTCTACTCCCTCAGCAGCGTGGTGACCGTGCCCTCCAGCAGCTTGGGCACCCAGACCTACA

TCTGCAACGTGAATCACAAGCCCAGCAACACCAAGGTGGACAAGAGAGTTGAGCCCAAATCTTGTGACAAAACTC

ACACATGCCCACCGTGCCCAGCACCTGAACTCCTGGGGGGACCGTCAGTCTTCCTCTTCCCCCCAAAACCCAAGGA

CACCCTCATGATCTCCCGGACCCCTGAGGTCACATGCGTGGTGGTGGACGTGAGCCACGAAGACCCTGAGGTCAA

GTTCAACTGGTACGTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTACAAGTGCAAGGTCT

CCAACAAAGCCCTCCCAGCCCCCATCGAGAAAACCATCTCCAAAGCCAAAGGGCAGCCCCGAGAACCACAGGTGT

ACACCCTGCCCCCATCCCGGGAGGAGATGACCAAGAACCAGGTCAGCCTGACCTGCCTGGTCAAAGGCTTCTATC

CCAGCGACATCGCCGTGGAGTGGGAGAGCAATGGGCAGCCGGAGAACAACTACAAGACCACGCCTCCCGTGCTG

GACTCCGACGGCTCCTTCTTCCTCTATAGCAAGCTCACCGTGGACAAGAGCAGGTGGCAGCAGGGGAACGTCTTC

TCATGCTCCGTGATGCATGAGGCTCTGCACAACCACTACACGCAGAAGAGCCTCTCCCTGTCTCCGGGTAAA

AB3HU HUMANIZED HEAVY CHAIN VARIABLE HEAVY CHAIN NUCLEOTIDE SEQUENCE
SEQ ID NO: 46
GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTGGATGAGCTGGGTCCGCCAGGCTCCAGGGAAGGGGCTGGAGTGGATCGGAG

TCATTGATACTAATGTTTATATATACTACGCGAACTGGGCAAAAGGCAGATTCACCATCTCCAGAGACAATTCCAA

GAACACGCTGTATCTTCAAATGAACAGCCTGAGAGCCGAGGACACGGCTGTGTATTACTGTGCGAGATATGTGGG

TAATAATGATGATTATATTAACTTGTGGGGCCAGGGAACCCTGGTCACCGTCTCGAGC

AB3HU HUMANIZED HEAVY CHAIN FULL-LENGTH AMINO ACID SEQUENCE. HUMAN GAMMA1
CONSTANT DOMAIN IS UNDERLINED
SEQ ID NO: 47
EVQLVESGGGLVQPGGSLRLSCAASGFSLSSYWMSWVRQAPGKGLEWIGVIDTNVYIYYANWAKGRFTISRDNSKNTL

YLQMNSLRAEDTAVYYCARYVGNNDDYINLWGQGTLVTVSS<u>ASTKGPSVFPLAPSSKSTSGGTAALGCLVKDYFPEPVT</u>

<u>VSWNSGALTSGVHTFPAVLQSSGLYSLSSVVTVPSSSLGTQTYICNVNHKPSNTKVDKRVEPKSCDKTHTCPPCPAPELL</u>

<u>GGPSVFLFPPKPKDTLMISRTPEVTCVVVDVSHEDPEVKFNWYVDGVEVHNAKTKPREEQYNSTYRVVSVLTVLHQD</u>

<u>WLNGKEYKCKVSNKALPAPIEKTISKAKGQPREPQVYTLPPSREEMTKNQVSLTCLVKGFYPSDIAVEWESNGQPENNY</u>

<u>KTTPPVLDSDGSFFLYSKLTVDKSRWQQGNVFSCSVMHEALHNHYTQKSLSLSPGK</u>

AB3HU HUMANIZED HEAVY CHAIN VARIABLE HEAVY CHAIN AMINO ACID SEQUENCE.
COMPLEMENTARITY DETERMINING REGIONS ARE UNDERLINED
SEQ ID NO: 48
EVQLVESGGGLVQPGGSLRLSCAASGFSL<u>SSYWMS</u>WVRQAPGKGLEWIG<u>VIDTNVYIYYANWAKG</u>RFTISRDNSKNTL

YLQMNSLRAEDTAVYYCAR<u>YVGNNDDYINL</u>WGQGTLVTVSS

AB4 CHIMERIC LIGHT CHAIN FULL-LENGTH NUCLEOTIDE SEQUENCE
SEQ ID NO: 49
GCATTCGAATTGACCCAGACTCCAGCCTCCGTGTCTGAACCTGTGGGAGGCACAGTCACCATCAAGTGCCAGGCC

AGTGAAAGCATTAGCAACTACTTATCCTGGTATCAGCAGATTCCAGGGCAGCCTCCCAACCTCCTGATCTATTATGC

ATCCAATCTGGCATCTGGGGTCCCATCGCGGTTCAAAGGCAGTGGATCTGGGACAGAGTTCACTCTCACCATCAGC

GACCTGGAGTGTGCCGATGCTGCCACTTACTACTGTCAAAGCTATTATGGTGGTGGTAGTGCCTATACTTTCGGCG

GAGGGACCGAGGTGGTGGTCAAACGTACGGTGGCTGCACCATCTGTCTTCATCTTCCCGCCATCTGATGAGCAGTT

GAAATCTGGAACTGCCTCTGTTGTGTGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGGACAGCAAGGACAGCACCTACAGCC

TCAGCAGCACCCTGACGCTGAGCAAAGCAGACTACGAGAAACACAAAGTCTACGCCTGCGAAGTCACCCATCAGG

GCCTGAGCTCGCCCGTCACAAAGAGCTTCAACAGGGGAGAGTGT

AB4 CHIMERIC LIGHT CHAIN VARIABLE LIGHT CHAIN NUCLEOTIDE SEQUENCE
SEQ ID NO: 50
GCATTCGAATTGACCCAGACTCCAGCCTCCGTGTCTGAACCTGTGGGAGGCACAGTCACCATCAAGTGCCAGGCC

AGTGAAAGCATTAGCAACTACTTATCCTGGTATCAGCAGATTCCAGGGCAGCCTCCCAACCTCCTGATCTATTATGC

ATCCAATCTGGCATCTGGGGTCCCATCGCGGTTCAAAGGCAGTGGATCTGGGACAGAGTTCACTCTCACCATCAGC

GACCTGGAGTGTGCCGATGCTGCCACTTACTACTGTCAAAGCTATTATGGTGGTGGTAGTGCCTATACTTTCGGCG

GAGGGACCGAGGTGGTGGTCAAA

AB4 CHIMERIC LIGHT CHAIN FULL-LENGTH AMINO ACID SEQUENCE. HUMAN KAPPA CONSTANT DOMAIN IS UNDERLINED

SEQ ID NO: 51

AFELTQTPASVSEPVGGTVTIKCQASESISNYLSWYQQIPGQPPNLLIYYASNLASGVPSRFKGSGSGTEFTLTISDLECAD

AATYYCQSYYGGGSAYTFGGGTEVVVK<u>RTVAAPSVFIFPPSDEQLKSGTASVVCLLNNFYPREAKVQWKVDNALQSGN</u>

<u>SQESVTEQDSKDSTYSLSSTLTLSKADYEKHKVYACEVTHQGLSSPVTKSFNRGEC</u>

AB4 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 52

AFELTQTPASVSEPVGGTVTIKC<u>QASESISNYLS</u>WYQQIPGQPPNLLIY<u>YASNLAS</u>GVPSRFKGSGSGTEFTLTISDLECAD

AATYYC<u>QSYYGGGSAYT</u>FGGGTEVVVK

AB4 CHIMERIC HEAVY CHAIN FULL-LENGTH NUCLEOTIDE SEQUENCE

SEQ ID NO: 53

CAGTCGGTGGAGGAGTCCGGGGGTCGCCTGGTCACGCCTGGGACACCCCTGACACTCACCTGCACAGTGTCTGGA

ATCGACCTCAGTGTCATCAATATGGGCTGGGTCCGCCAGGCTCCAGGGGAGGGGCTGGAATGGATCGGAACCAT

TACTTATGTTGGTAACACATATTACGCGAGCTGGGCGAAAGGCCGATTCACCATCTCCAAAACCTCGACCACGGTG

GATCTGAAAATCACCAGTCCGACAACCGAGGACACGGCCACTTATTTCTGTGCCAGAGAATCTGGTACTATTTATT

ACAGTTACTTTAACTTGTGGGGCCAAGGCACCCTGGTCACCGTCTCGAGCGCTAGCACCAAGGGCCCATCGGTCTT

CCCCCTGGCACCCTCCTCCAAGAGCACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCTTGGGCACCCAGACCTACATCTGCAACG

TGAATCACAAGCCCAGCAACACCAAGGTGGACAAGAGAGTTGAGCCCAAATCTTGTGACAAAACTCACACATGCC

CACCGTGCCCAGCACCTGAACTCCTGGGGGGACCGTCAGTCTTCCTCTTCCCCCCAAAACCCAAGGACACCCTCAT

GATCTCCCGGACCCCTGAGGTCACATGCGTGGTGGTGGACGTGAGCCACGAAGACCCTGAGGTCAAGTTCAACTG

GTACGTGGACGGCGTGGAGGTGCATAATGCCAAGACAAAGCCGCGGGAGGAGCAGTACAACAGCACGTACCGT

GTGGTCAGCGTCCTCACCGTCCTGCACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCCCCGAGAACCACAGGTGTACACCCTG

CCCCCATCCCGGGAGGAGATGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGCTGGACTCCGA

CGGCTCCTTCTTCCTCTATAGCAAGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCTCCGGGTAAA

AB4 CHIMERIC HEAVY CHAIN VARIABLE HEAVY CHAIN NUCLEOTIDE SEQUENCE

SEQ ID NO: 54

CAGTCGGTGGAGGAGTCCGGGGGTCGCCTGGTCACGCCTGGGACACCCCTGACACTCACCTGCACAGTGTCTGGA

ATCGACCTCAGTGTCATCAATATGGGCTGGGTCCGCCAGGCTCCAGGGGAGGGGCTGGAATGGATCGGAACCAT

TACTTATGTTGGTAACACATATTACGCGAGCTGGGCGAAAGGCCGATTCACCATCTCCAAAACCTCGACCACGGTG

GATCTGAAAATCACCAGTCCGACAACCGAGGACACGGCCACTTATTTCTGTGCCAGAGAATCTGGTACTATTTATT

ACAGTTACTTTAACTTGTGGGGCCAAGGCACCCTGGTCACCGTCTCGAGC

AB4 CHIMERIC HEAVY CHAIN FULL-LENGTH AMINO ACID SEQUENCE. HUMAN GAMMA-1 CONSTANT DOMAIN IS UNDERLINED

SEQ ID NO: 55

QSVEESGGRLVTPGTPLTLTCTVSGIDLSVINMGWVRQAPGEGLEWIGTITYVGNTYYASWAKGRFTISKTSTTVDLKIT

SPTTEDTATYFCARESGTIYYSYFNLWGQGTLVTVSS<u>ASTKGPSVFPLAPSSKSTSGGTAALGCLVKDYFPEPVTVSWNS</u>

<u>GALTSGVHTFPAVLQSSGLYSLSSVVTVPSSSLGTQTYICNVNHKPSNTKVDKRVEPKSCDKTHTCPPCPAPELLGGPSVF</u>

<u>LFPPKPKDTLMISRTPEVTCVVVDVSHEDPEVKFNWYVDGVEVHNAKTKPREEQYNSTYRVVSVLTVLHQDWLNGKEY</u>

<u>KCKVSNKALPAPIEKTISKAKGQPREPQVYTLPPSREEMTKNQVSLTCLVKGFYPSDIAVEWESNGQPENNYKTTPPVLD</u>

<u>SDGSFFLYSKLTVDKSRWQQGNVFSCSVMHEALHNHYTQKSLSLSPGK</u>

AB4 CHIMERIC HEAVY CHAIN VARIABLE HEAVY CHAIN AMINO ACID SEQUENCE. COMPLIMENTARITY
DETERMINING REGIONS ARE UNDERLINED

SEQ ID NO: 56

QSVEESGGRLVTPGTPLTLTCTVSGIDLS<u>VINMG</u>WVRQAPGEGLEWIG<u>TITYVGNTYYASWAKG</u>RFTISKTSTTVDLKIT

SPTTEDTATYFCAR<u>ESGTIYYSYFNL</u>WGQGTLVTVSS

AB4HU HUMANIZED LIGHT CHAIN FULL-LENGTH NUCLEOTIDE SEQUENCE

SEQ ID NO: 57

GCATTCGAATTGACCCAGTCTCCATCCTCCCTGTCTGCATCTGTAGGAGACAGAGTCACCATCAAGTGCCAGGCCA

GTGAAAGCATTAGCAACTACTTATCCTGGTATCAGCAGATTCCAGGGAAAGTTCCTAAGCTCCTGATCTATTATGC

ATCCAATCTGGCATCTGGGGTCCCATCTCGGTTCAGTGGCAGTGGATCTGGGACAGATTTCACTCTCACCATCAGC

AGCCTGCAGCCTGAAGATGTTGCAACTTATTACTGTCAAAGCTATTATGGTGGTGGTAGTGCCTATACTTTCGGCG

GAGGGACCAAGGTGGAGATCAAACGTACGGTGGCTGCACCATCTGTCTTCATCTTCCCGCCATCTGATGAGCAGTT

GAAATCTGGAACTGCCTCTGTTGTGTGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGGACAGCAAGGACAGCACCTACAGCC

TCAGCAGCACCCTGACGCTGAGCAAAGCAGACTACGAGAAACACAAAGTCTACGCCTGCGAAGTCACCCATCAGG

GCCTGAGCTCGCCCGTCACAAAGAGCTTCAACAGGGGAGAGTGT

AB4HU HUMANIZED LIGHT CHAIN VARIABLE LIGHT CHAIN NUCLEOTIDE SEQUENCE

SEQ ID NO: 58

GCATTCGAATTGACCCAGTCTCCATCCTCCCTGTCTGCATCTGTAGGAGACAGAGTCACCATCAAGTGCCAGGCCA

GTGAAAGCATTAGCAACTACTTATCCTGGTATCAGCAGATTCCAGGGAAAGTTCCTAAGCTCCTGATCTATTATGC

ATCCAATCTGGCATCTGGGGTCCCATCTCGGTTCAGTGGCAGTGGATCTGGGACAGATTTCACTCTCACCATCAGC

AGCCTGCAGCCTGAAGATGTTGCAACTTATTACTGTCAAAGCTATTATGGTGGTGGTAGTGCCTATACTTTCGGCG

GAGGGACCAAGGTGGAGATCAAA

AB4HU HUMANIZED LIGHT CHAIN FULL-LENGTH AMINO ACID SEQUENCE. HUMAN KAPPA CONSTANT
DOMAIN IS UNDERLINED

SEQ ID NO: 59

AFELTQSPSSLSASVGDRVTIKCQASESISNYLSWYQQIPGKVPKLLIYYASNLASGVPSRFSGSGSGTDFTLTISSLQPEDV

ATYYCQSYYGGGSAYTFGGGTKVEIK<u>RTVAAPSVFIFPPSDEQLKSGTASVVCLLNNFYPREAKVQWKVDNALQSGNSQ</u>

<u>ESVTEQDSKDSTYSLSSTLTLSKADYEKHKVYACEVTHQGLSSPVTKSFNRGEC</u>

AB4HU HUMANIZED LIGHT CHAIN VARIABLE LIGHT CHAIN AMINO ACID SEQUENCE.
COMPLEMENTARITY DETERMINING REGIONS ARE UNDERLINED

SEQ ID NO: 60

AFELTQSPSSLSASVGDRVTIKC<u>QASESISNYLS</u>WYQQIPGKVPKLLIY<u>YASNLAS</u>GVPSRFSGSGSGTDFTLTISSLQPEDV

ATYYC<u>QSYYGGGSAYT</u>FGGGTKVEIK

AB4HU HUMANIZED HEAVY CHAIN FULL-LENGTH NUCLEOTIDE SEQUENCE

SEQ ID NO: 61

GAGGTGCAGCTGGTGGAGTCTGGGGGAGGCTTGGTCCAGCCTGGGGGGTCCCTGAGACTCTCCTGTACAGTGTC

TGGAATCGACCTCAGTGTCATCAATATGGGCTGGGTCCGCCAGGCTCCAGGGAAGGGGCTGGAGTGGATCGGAA

CCATTACTTATGTTGGTAACACATATTACGCGAGCTGGGCGAAAGGCAGATTCACCATCTCCAAAACCTCGACCAC

GGTGGATCTTAAAATCACCAGTCCGACAACCGAGGACACGGCTGTGTATTACTGTGCGAGAGAATCTGGTACTAT

TTATTACAGTTACTTTAACTTGTGGGGCCAAGGGACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

```
ACCGTGTGGTCAGCGTCCTCACCGTCCTGCACCAGGACTGGCTGAATGGCAAGGAGTACAAGTGCGCGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGATGAGCTGACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACAAGACCACGCCTCCCGTGCTGGACT

CCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT
```

AB4HU HUMANIZED HEAVY CHAIN VARIABLE HEAVY CHAIN NUCLEOTIDE SEQUENCE
                                                                    SEQ ID NO: 62
```
GAGGTGCAGCTGGTGGAGTCTGGGGGAGGCTTGGTCCAGCCTGGGGGGTCCCTGAGACTCTCCTGTACAGTGTC

TGGAATCGACCTCAGTGTCATCAATATGGGCTGGGTCCGCCAGGCTCCAGGGAAGGGGCTGGAGTGGATCGGAA

CCATTACTTATGTTGGTAACACATATTACGCGAGCTGGGCGAAAGGCAGATTCACCATCTCCAAAACCTCGACCAC

GGTGGATCTTAAAATCACCAGTCCGACAACCGAGGACACGGCTGTGTATTACTGTGCGAGAGAATCTGGTACTAT

TTATTACAGTTACTTTAACTTGTGGGGCCAAGGGACCCTGGTCACCGTCTCGAGC
```

AB4HU HUMANIZED HEAVY CHAIN FULL-LENGTH AMINO ACID SEQUENCE. HUMAN GAMMA1
CONSTANT DOMAIN IS UNDERLINED
                                                                    SEQ ID NO: 63
EVQLVESGGGLVQPGGSLRLSCTVSGIDLSVINMGWVRQAPGKGLEWIGTITYVGNTYYASWAKGRFTISKTSTTVDLK

ITSPTTEDTAVYYCARESGTIYYSYFNLWGQGTLVTVSS<u>ASTKGPSVFPLAPSSKSTSGGTAALGCLVKDYFPEPVTVSWN

SGALTSGVHTFPAVLQSSGLYSLSSVVTVPSSSLGTQTYICNVNHKPSNTKVDKRVEPKSCDKTHTCPPCPAPEAAGAPS

VFLFPPKPKDTLMISRTPEVTCVVVDVSHEDPEVKFNWYVDGVEVHNAKTKPREEQYNSTYRVVSVLTVLHQDWLNG</u>

KEYKCAVSNKALPAPIEKTISKAKGQPREPQVYTLPPSRDELTKNQVSLTCLVKGFYPSDIAVEWESNGQPENNYKTTPP

<u>VLDSDGSFFLYSKLTVDKSRWQQGNVFSCSVMHEALHNHYTQKSLSLSPG</u>

AB4HU HUMANIZED HEAVY CHAIN VARIABLE HEAVY CHAIN AMINO ACID SEQUENCE.
COMPLEMENTARITY DETERMINING REGIONS ARE UNDERLINED
                                                                    SEQ ID NO: 64
EVQLVESGGGLVQPGGSLRLSCTVSGIDLS<u>VINMG</u>WVRQAPGKGLEWIGT<u>ITYVGNTYYASWAK</u>GRFTISKTSTTVDLK

ITSPTTEDTAVYYCAR<u>ESGTIYYSYFNL</u>WGQGTLVTVSS

AB5 CHIMERIC LIGHT CHAIN FULL-LENGTH NUCLEOTIDE SEQUENCE
                                                                    SEQ ID NO: 65
```
GCCTATGATATGACCCAGACTCCAGCCTCTGTGGAGGTAGCTGTGGGAGGCACAGTCACCATCAAGTGCCAGGCC

AGTGAGGACATTTATAGCTTCTTGGCCTGGTATCAGCTGAAACCAGGGCAGTCTCCCAAGCTCCTGATCCATTCTG

CATCCTCTCTGGCATCTGGGGTCTCTTCGCGGTTCAAAGGCAGTGGATCTGGGACACACTTCACTCTCACCATCAGC

GGCGTGGAGTGTGCCGATGCTGCCACTTATTATTGTCAACAGGGTTATGGTAAAAATAATGTTGATAATGCTTTCG

GCGGAGGGACCGAGGTGGTGGTCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT
```

AB5 CHIMERIC LIGHT CHAIN VARIABLE LIGHT CHAIN NUCLEOTIDE SEQUENCE
                                                                    SEQ ID NO: 66
```
GCCTATGATATGACCCAGACTCCAGCCTCTGTGGAGGTAGCTGTGGGAGGCACAGTCACCATCAAGTGCCAGGCC

AGTGAGGACATTTATAGCTTCTTGGCCTGGTATCAGCTGAAACCAGGGCAGTCTCCCAAGCTCCTGATCCATTCTG

CATCCTCTCTGGCATCTGGGGTCTCTTCGCGGTTCAAAGGCAGTGGATCTGGGACACACTTCACTCTCACCATCAGC

GGCGTGGAGTGTGCCGATGCTGCCACTTATTATTGTCAACAGGGTTATGGTAAAAATAATGTTGATAATGCTTTCG

GCGGAGGGACCGAGGTGGTGGTCAAA
```

AB5 CHIMERIC LIGHT CHAIN FULL-LENGTH AMINO ACID SEQUENCE. HUMAN KAPPA CONSTANT DOMAIN IS UNDERLINED

SEQ ID NO: 67

AYDMTQTPASVEVAVGGTVTIKCQASEDIYSFLAWYQLKPGQSPKLLIHSASSLASGVSSRFKGSGSGTHFTLTISGVECA

DAATYYCQQGYGKNNVDNAFGGGTEVVVK<u>RTVAAPSVFIFPPSDEQLKSGTASVVCLLNNFYPREAKVQWKVDNALQ</u>

<u>SGNSQESVTEQDSKDSTYSLSSTLTLSKADYEKHKVYACEVTHQGLSSPVTKSFNRGEC</u>

AB5 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 68

AYDMTQTPASVEVAVGGTVTIKC<u>QASEDIYSFL</u>AWYQLKPGQSPKLLIH<u>SASSLAS</u>GVSSRFKGSGSGTHFTLTISGVECA

DAATYYC<u>QQGYGKNNVDNA</u>FGGGTEVVVK

AB5 CHIMERIC HEAVY CHAIN FULL-LENGTH NUCLEOTIDE SEQUENCE

SEQ ID NO: 69

CAGTCGGTGGAGGAGTCCGGGGGTCGCCTGGTCACGCCTGGGACACCCCTGACACTCACCTGCACAGTCTCCGGA

ATCGACCTTAATACCTACGACATGATCTGGGTCCGCCAGGCTCCAGGGAAGGGGCTGGAGTGGATCGGAATCATT

ACTTATAGTGGTAGTAGATACTACGCGAACTGGGCGAAAGGCCGATTCACCATCTCCAAAACCTCGACCACGGTG

GATCTGAGAATCACCAGTCCGACAACCGAGGACACGGCCACCTATTTCTGTGCCAGGGATTATATGAGTGGTTCCC

ACTTGTGGGGCCCAGGCACCCTCGTCACCGTCTCGAGCGCTAGCACCAAGGGCCCATCGGTCTTCCCCCTGGCACC

CTCCTCCAAGAGCACCTCTGGGGGCACAGCGGCCCTGGGCTGCCTGGTCAAGGACTACTTCCCCGAACCGGTGAC

GGTGTCGTGGAACTCAGGCGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCTGCAACGTGAATCACAAGC

CCAGCAACACCAAGGTGGACAAGAGAGTTGAGCCCAAATCTTGTGACAAAACTCACACATGCCCACCGTGCCCAG

CACCTGAACTCCTGGGGGGACCGTCAGTCTTCCTCTTCCCCCCAAAACCCAAGGACACCCTCATGATCTCCCGGACC

CCTGAGGTCACATGCGTGGTGGTGGACGTGAGCCACGAAGACCCTGAGGTCAAGTTCAACTGGTACGTGGACGG

CGTGGAGGTGCATAATGCCAAGACAAAGCCGCGGGAGGAGCAGTACAACAGCACGTACCGTGTGGTCAGCGTCC

TCACCGTCCTGCACCAGGACTGGCTGAATGGCAAGGAGTACAAGTGCAAGGTCTCCAACAAAGCCCTCCCAGCCC

CCATCGAGAAAACCATCTCCAAAGCCAAAGGGCAGCCCCGAGAACCACAGGTGTACACCCTGCCCCCATCCCGGG

AGGAGATGACCAAGAACCAGGTCAGCCTGACCTGCCTGGTCAAAGGCTTCTATCCCAGCGACATCGCCGTGGAGT

GGGAGAGCAATGGGCAGCCGGAGAACAACTACAAGACCACGCCTCCCGTGCTGGACTCCGACGGCTCCTTCTTCC

TCTATAGCAAGCTCACCGTGGACAAGAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

AB5 CHIMERIC HEAVY CHAIN VARIABLE HEAVY CHAIN NUCLEOTIDE SEQUENCE

SEQ ID NO: 70

CAGTCGGTGGAGGAGTCCGGGGGTCGCCTGGTCACGCCTGGGACACCCCTGACACTCACCTGCACAGTCTCCGGA

ATCGACCTTAATACCTACGACATGATCTGGGTCCGCCAGGCTCCAGGGAAGGGGCTGGAGTGGATCGGAATCATT

ACTTATAGTGGTAGTAGATACTACGCGAACTGGGCGAAAGGCCGATTCACCATCTCCAAAACCTCGACCACGGTG

GATCTGAGAATCACCAGTCCGACAACCGAGGACACGGCCACCTATTTCTGTGCCAGGGATTATATGAGTGGTTCCC

ACTTGTGGGGCCCAGGCACCCTCGTCACCGTCTCGAGC

AB5 CHIMERIC HEAVY CHAIN FULL-LENGTH AMINO ACID SEQUENCE. HUMAN GAMMA-1 CONSTANT DOMAIN IS UNDERLINED

SEQ ID NO: 71

QSVEESGGRLVTPGTPLTLTCTVSGIDLNTYDMIWVRQAPGKGLEWIGIITYSGSRYYANWAKGRFTISKTSTTVDLRITS

PTTEDTATYFCARDYMSGSHLWGPGTLVTVSS<u>ASTKGPSVFPLAPSSKSTSGGTAALGCLVKDYFPEPVTVSWNSGALT</u>

<u>SGVHTFPAVLQSSGLYSLSSVVTVPSSSLGTQTYICNVNHKPSNTKVDKRVEPKSCDKTHTCPPCPAPELLGGPSVFLFPP</u>

<u>KPKDTLMISRTPEVTCVVVDVSHEDPEVKFNWYVDGVEVHNAKTKPREEQYNSTYRVVSVLTVLHQDWLNGKEYKCK</u>

<u>VSNKALPAPIEKTISKAKGQPREPQVYTLPPSREEMTKNQVSLTCLVKGFYPSDIAVEWESNGQPENNYKTTPPVLDSDG</u>

<u>SFFLYSKLTVDKSRWQQGNVFSCSVMHEALHNHYTQKSLSLSPGK</u>

AB5 CHIMERIC HEAVY CHAIN VARIABLE HEAVY CHAIN AMINO ACID SEQUENCE. COMPLIMENTARITY
DETERMINING REGIONS ARE UNDERLINED

SEQ ID NO: 72

QSVEESGGRLVTPGTPLTLTCTVSGIDLN<u>TYDMI</u>WVRQAPGKGLEWIG<u>IITYSGSRYYANWAKG</u>RFTISKTSTTVDLRITS

PTTEDTATYFCAR<u>DYMSGSHL</u>WGPGTLVTVSS

AB5HU HUMANIZED LIGHT CHAIN FULL-LENGTH NUCLEOTIDE SEQUENCE

SEQ ID NO: 73

GCCTATGATATGACCCAGTCTCCATCTTCCGTGTCTGCATCTGTAGGAGACAGAGTCACCATCAAGTGTCAGGCCA

GTGAGGACATTTATAGCTTCTTGGCCTGGTATCAGCAGAAACCAGGGAAAGCCCCTAAGCTCCTGATCCATTCTGC

ATCCTCTCTGGCATCTGGGGTCCCATCAAGGTTCAGCGGCAGTGGATCTGGGACAGATTTCACTCTCACCATCAGC

AGCCTGCAGCCTGAAGATTTTGCAACTTACTATTGTCAACAGGGTTATGGTAAAAATAATGTTGATAATGCTTTCG

GCGGAGGGACCAAGGTGGAGATCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

AB5HU HUMANIZED LIGHT CHAIN VARIABLE LIGHT CHAIN NUCLEOTIDE SEQUENCE

SEQ ID NO: 74

GCCTATGATATGACCCAGTCTCCATCTTCCGTGTCTGCATCTGTAGGAGACAGAGTCACCATCAAGTGTCAGGCCA

GTGAGGACATTTATAGCTTCTTGGCCTGGTATCAGCAGAAACCAGGGAAAGCCCCTAAGCTCCTGATCCATTCTGC

ATCCTCTCTGGCATCTGGGGTCCCATCAAGGTTCAGCGGCAGTGGATCTGGGACAGATTTCACTCTCACCATCAGC

AGCCTGCAGCCTGAAGATTTTGCAACTTACTATTGTCAACAGGGTTATGGTAAAAATAATGTTGATAATGCTTTCG

GCGGAGGGACCAAGGTGGAGATCAAA

AB5HU HUMANIZED LIGHT CHAIN FULL-LENGTH AMINO ACID SEQUENCE. HUMAN KAPPA CONSTANT
DOMAIN IS UNDERLINED

SEQ ID NO: 75

AYDMTQSPSSVSASVGDRVTIKCQASEDIYSFLAWYQQKPGKAPKLLIHSASSLASGVPSRFSGSGSGTDFTLTISSLQPE

DFATYYCQQGYGKNNVDNAFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

AB5HU HUMANIZED LIGHT CHAIN VARIABLE LIGHT CHAIN AMINO ACID SEQUENCE.
COMPLEMENTARITY DETERMINING REGIONS ARE UNDERLINED

SEQ ID NO: 76

AYDMTQSPSSVSASVGDRVTIKC<u>QASEDIYSFLA</u>WYQQKPGKAPKLLIHS<u>ASSLAS</u>GVPSRFSGSGSGTDFTLTISSLQPE

DFATYYC<u>QQGYGKNNVDN</u>AFGGGTKVEIK

AB5HU HUMANIZED HEAVY CHAIN FULL-LENGTH NUCLEOTIDE SEQUENCE

SEQ ID NO: 77

CAGTCGGTGGAGGAGTCTGGGGGAGGCTTGGTCCAGCCTGGGGGGTCCCTGAGACTCTCCTGTACCGCCTCTGG

AATCGACCTTAATACCTACGACATGATCTGGGTCCGCCAGGCTCCAGGCAAGGGGCTAGAGTGGGTTGGAATCAT

TACTTATAGTGGTAGTAGATACTACGCGAACTGGGCGAAAGGCCGATTCACCATCTCCAAAGACAATACCAAGAA

CACGGTGTATCTGCAAATGAACAGCCTGAGAGCTGAGGACACGGCTGTGTATTACTGTGCGAGAGATTATATGAG

TGGTTCCCACTTGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAACTCCTGGGGGGACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

```
GTCAGCGTCCTCACCGTCCTGCACCAGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGAGGAGATGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGTAAA
```

AB5HU HUMANIZED HEAVY CHAIN VARIABLE HEAVY CHAIN NUCLEOTIDE SEQUENCE
                                                                SEQ ID NO: 78
```
CAGTCGGTGGAGGAGTCTGGGGGAGGCTTGGTCCAGCCTGGGGGGTCCCTGAGACTCTCCTGTACCGCCTCTGG

AATCGACCTTAATACCTACGACATGATCTGGGTCCGCCAGGCTCCAGGCAAGGGGCTAGAGTGGGTTGGAATCAT

TACTTATAGTGGTAGTAGATACTACGCGAACTGGGCGAAAGGCCGATTCACCATCTCCAAAGACAATACCAAGAA

CACGGTGTATCTGCAAATGAACAGCCTGAGAGCTGAGGACACGGCTGTGTATTACTGTGCGAGAGATTATATGAG

TGGTTCCCACTTGTGGGGCCAGGGAACCCTGGTCACCGTCTCGAGC
```

AB5HU HUMANIZED HEAVY CHAIN FULL-LENGTH AMINO ACID SEQUENCE. HUMAN GAMMA1
CONSTANT DOMAIN IS UNDERLINED
                                                                SEQ ID NO: 79
QSVEESGGGLVQPGGSLRLSCTASGIDLNTYDMIWVRQAPGKGLEWVGIITYSGSRYYANWAKGRFTISKDNTKNTVY

LQMNSLRAEDTAVYYCARDYMSGSHLWGQGTLVTVSS<u>ASTKGPSVFPLAPSSKSTSGGTAALGCLVKDYFPEPVTVSW</u>

<u>NSGALTSGVHTFPAVLQSSGLYSLSSVVTVPSSSLGTQTYICNVNHKPSNTKVDKRVEPKSCDKTHTCPPCPAPELLGGPS</u>

<u>VFLFPPKPKDTLMISRTPEVTCVVVDVSHEDPEVKFNWYVDGVEVHNAKTKPREEQYNSTYRVVSVLTVLHQDWLNG</u>

<u>KEYKCKVSNKALPAPIEKTISKAKGQPREPQVYTLPPSREEMTKNQVSLTCLVKGFYPSDIAVEWESNGQPENNYKTTPP</u>

<u>VLDSDGSFFLYSKLTVDKSRWQQGNVFSCSVMHEALHNHYTQKSLSLSPGK</u>

AB5HU HUMANIZED HEAVY CHAIN VARIABLE HEAVY CHAIN AMINO ACID SEQUENCE.
COMPLEMENTARITY DETERMINING REGIONS ARE UNDERLINED
                                                                SEQ ID NO: 80
QSVEESGGGLVQPGGSLRLSCTASGIDLN<u>TYDMI</u>WVRQAPGKGLEWVG<u>IITYSGSRYYANWAKG</u>RFTISKDNTKNTVY

LQMNSLRAEDTAVYYCAR<u>DYMSGSHL</u>WGQGTLVTVSS

HUMAN PD-L1 FULL-LENGTH NUCLEOTIDE SEQUENCE
                                                                SEQ ID NO: 81
```
TTTACTGTCACGGTTCCCAAGGACCTATATGTGGTAGAGTATGGTAGCAATATGACAATTGAATGCAAATTCCCAG

TAGAAAAACAATTAGACCTGGCTGCACTAATTGTCTATTGGGAAATGGAGGATAAGAACATTATTCAATTTGTGCA

TGGAGAGGAAGACCTGAAGGTTCAGCATAGTAGCTACAGACAGAGGGCCCGGCTGTTGAAGGACCAGCTCTCCC

TGGGAAATGCTGCACTTCAGATCACAGATGTGAAATTGCAGGATGCAGGGGTGTACCGCTGCATGATCAGCTATG

GTGGTGCCGACTACAAGCGAATTACTGTGAAAGTCAATGCCCCATACAACAAAATCAACCAAAGAATTTTGGTTGT

GGATCCAGTCACCTCTGAACATGAACTGACATGTCAGGCTGAGGGCTACCCCAAGGCCGAAGTCATCTGGACAAG

CAGTGACCATCAAGTCCTGAGTGGTAAGACCACCACCACCAATTCCAAGAGAGAGGAGAAGCTTTTCAATGTGAC

CAGCACACTGAGAATCAACACAACAACTAATGAGATTTTCTACTGCACTTTTAGGAGATTAGATCCTGAGGAAAAC

CATACAGCTGAATTGGTCATCCCAGAACTACCTCTGGCACATCCTCCAAATGAAAGGACTCACTTGGTAATTCTGG

GAGCCATCTTATTATGCCTTGGTGTAGCACTGACATTCATCTTCCGTTTAAGAAAAGGGAGAATGATGGATGTGAA

AAAATGTGGCATCCAAGATACAAACTCAAAGAAGCAAAGTGATACACATTTGGAGGAGACG
```

HUMAN PD-L1 FULL-LENGTH AMINO ACID SEQUENCE
                                                                SEQ ID NO: 82
FTVTVPKDLYVVEYGSNMTIECKFPVEKQLDLAALIVYWEMEDKNIIQFVHGEEDLKVQHSSYRQRARLLKDQLSLGNA

ALQITDVKLQDAGVYRCMISYGGADYKRITVKVNAPYNKINQRILVVDPVTSEHELTCQAEGYPKAEVIWTSSDHQVLS

GKTTTTNSKREEKLFNVTSTLRINTTTNEIFYCTFRRLDPEENHTAELVIPELPLAHPPNERTHLVILGAILLCLGVALTFIFRL

RKGRMMDVKKCGIQDTNSKKQSDTHLEET

-continued

HUMAN PD-L1 EXTRACELLULAR DOMAIN NUCLEOTIDE SEQUENCE

SEQ ID NO: 83

TTTACTGTCACGGTTCCCAAGGACCTATATGTGGTAGAGTATGGTAGCAATATGACAATTGAATGCAAATTCCCAG

TAGAAAAACAATTAGACCTGGCTGCACTAATTGTCTATTGGGAAATGGAGGATAAGAACATTATTCAATTTGTGCA

TGGAGAGGAAGACCTGAAGGTTCAGCATAGTAGCTACAGACAGAGGGCCCGGCTGTTGAAGGACCAGCTCTCCC

TGGGAAATGCTGCACTTCAGATCACAGATGTGAAATTGCAGGATGCAGGGGTGTACCGCTGCATGATCAGCTATG

GTGGTGCCGACTACAAGCGAATTACTGTGAAAGTCAATGCCCCATACAACAAAATCAACCAAAGAATTTTGGTTGT

GGATCCAGTCACCTCTGAACATGAACTGACATGTCAGGCTGAGGGCTACCCCAAGGCCGAAGTCATCTGGACAAG

CAGTGACCATCAAGTCCTGAGTGGTAAGACCACCACCACCAATTCCAAGAGAGAGGAGAAGCTTTTCAATGTGAC

CAGCACACTGAGAATCAACACAACAACTAATGAGATTTTCTACTGCACTTTTAGGAGATTAGATCCTGAGGAAAAC

CATACAGCTGAATTGGTCATCCCAGAACTACCTCTGGCACATCCTCCAAATGAAAGGACT

HUMAN PD-L1 EXTRACELLULAR DOMAIN AMINO ACID SEQUENCE

SEQ ID NO: 84

FTVTVPKDLYVVEYGSNMTIECKFPVEKQLDLAALIVYWEMEDKNIIQFVHGEEDLKVQHSSYRQRARLLKDQLSLGNA

ALQITDVKLQDAGVYRCMISYGGADYKRITVKVNAPYNKINQRILVVDPVTSEHELTCQAEGYPKAEVIWTSSDHQVLS

GKTTTTNSKREEKLFNVTSTLRINTTTNEIFYCTFRRLDPEENHTAELVIPELPLAHPPNERT

---

What is claimed is:

1. An isolated monoclonal antibody (mAb) or antigen-binding fragment thereof having a binding specificity to human PD-L1, wherein the mAb or antigen-binding fragment thereof comprises,
    a variable light chain comprising SEQ ID NO:4, and a variable heavy chain comprising SEQ ID NO:8,
    a variable light chain comprising SEQ ID NO:12, and a variable heavy chain comprising SEQ ID NO:16,
    a variable light chain comprising SEQ ID NO:20, and a variable heavy chain comprising SEQ ID NO:24,
    a variable light chain comprising SEQ ID NO:28, and a variable heavy chain comprising SEQ ID NO:32,
    a variable light chain comprising SEQ ID NO:36, and a variable heavy chain comprising SEQ ID NO:40,
    a variable light chain comprising SEQ ID NO:44, and a variable heavy chain comprising SEQ ID NO:48,
    a variable light chain comprising SEQ ID NO:52, and a variable heavy chain comprising SEQ ID NO:56,
    a variable light chain comprising SEQ ID NO:60, and a variable heavy chain comprising SEQ ID NO:64,
    a variable light chain comprising SEQ ID NO:68, and a variable heavy chain comprising SEQ ID NO:72, or
    a variable light chain comprising SEQ ID NO:76, and a variable heavy chain comprising SEQ ID NO:80.

2. The isolated mAb or antigen-binding fragment according to claim 1, having a binding affinity to PD-L1 with a Kd not greater than 70 nM.

3. The isolated mAb or antigen-binding fragment according to claim 1, exhibiting one or more functional properties selected from a group consisting of affinity binding to PD-L1, inhibiting binding of PD-L1 to PD-1, enhancing T cell activation, stimulating antibody responses, reversing the suppressive function of immunosuppressive cells, or a combination thereof.

4. An isolated mAb or antigen-binding fragment thereof having a binding specificity to human PD-L1, wherein the isolated mAb or antigen-binding fragment thereof comprises,
    complementarity determining region (CDR)1, CDR2, and CDR3 of SEQ ID NO: 4 and CDR1, CDR2, and CDR3 of SEQ ID NO: 8,
    complementarity determining region (CDR)1, CDR2, and CDR3 of SEQ ID NO: 12 and CDR1, CDR2, and CDR3 of SEQ ID NO: 16,
    complementarity determining region (CDR)1, CDR2, and CDR3 of SEQ ID NO: 20 and CDR1, CDR2, and CDR3 of SEQ ID NO: 24,
    complementarity determining region (CDR)1, CDR2, and CDR3 of SEQ ID NO: 28 and CDR1, CDR2, and CDR3 of SEQ ID NO: 32,
    complementarity determining region (CDR)1, CDR2, and CDR3 of SEQ ID NO: 36 and CDR1, CDR2, and CDR3 of SEQ ID NO: 40,
    complementarity determining region (CDR)1, CDR2, and CDR3 of SEQ ID NO: 44 and CDR1, CDR2, and CDR3 of SEQ ID NO: 48,
    complementarity determining region (CDR)1, CDR2, and CDR3 of SEQ ID NO: 52 and CDR1, CDR2, and CDR3 of SEQ ID NO: 56,
    complementarity determining region (CDR)1, CDR2, and CDR3 of SEQ ID NO: 60 and CDR1, CDR2, and CDR3 of SEQ ID NO: 64,
    complementarity determining region (CDR)1, CDR2, and CDR3 of SEQ ID NO: 68 and CDR1, CDR2, and CDR3 of SEQ ID NO: 72, or
    complementarity determining region (CDR)1, CDR2, and CDR3 of SEQ ID NO: 76 and CDR1, CDR2, and CDR3 of SEQ ID NO: 80.

5. The isolated mAb or antigen-binding fragment thereof according to claim 1 or 4, wherein the isolated mAb or antigen-binding fragment comprises
    an IgG heavy chain having at least 98% sequence identity to SEQ ID NO: 7, and a kappa light chain having at least 98% sequence identity to SEQ ID NO: 3,
    an IgG1 heavy chain having at least 98% sequence identity to SEQ ID NO: 15, and a kappa light chain having at least 98% sequence identity to SEQ ID NO: 11,
    an IgG1 heavy chain having at least 98% sequence identity to SEQ ID NO: 23, and a kappa light chain having at least 98% sequence identity to SEQ ID NO: 19,
    an IgG1 heavy chain having at least 98% sequence identity to SEQ ID NO: 31, and a kappa light chain having at least 98% sequence identity to SEQ ID NO: 27,
    an IgG1 heavy chain having at least 98% sequence identity to SEQ ID NO: 39, and a kappa light chain having at least 98% sequence identity to SEQ ID NO: 35, an IgG1 heavy chain having at least 98% sequence identity to SEQ ID NO: 47, and a kappa light chain having at least 98% sequence identity to SEQ ID NO: 43, an IgG1 heavy chain having at least 98% sequence identity to SEQ ID NO: 55, and a kappa light chain having at least 98% sequence identity to SEQ ID NO: 51, an IgG1 heavy chain having at least 98% sequence identity to SEQ ID NO: 63, and a kappa light chain having at least 98% sequence identity to SEQ ID NO: 59, an IgG1 heavy chain having at least 98% sequence identity to SEQ ID NO: 71, and a kappa light chain having at least 98% sequence identity to SEQ ID NO: 67, or an IgG1 heavy chain having at least 98% sequence identity to SEQ ID NO: 79, and a kappa light chain having at least 98% sequence identity to SEQ ID NO: 75.

6. The isolated mAb or antigen-binding fragment thereof according to claim 1 or 4, wherein the antigen-binding fragment comprises a Fv, a Fab, a F(ab')2, a scFV or a scFV2 fragment.

7. The isolated mAb or antigen-binding fragment thereof according to claim 1 or 4, wherein the isolated mAb comprises a bispecific antibody, tri-specific antibody, multi-specific antibody, wherein the isolated mAb is a humanized antibody, a chimeric antibody, a recombinant antibody, or wherein the isolated mAb comprises an IgG.

8. An isolated nucleic acid encoding the isolated mAb or antigen-binding fragment according to claim 1.

9. An expression vector comprising the isolated nucleic acid of claim 8.

10. A host cell comprising the nucleic acid of claim 8, wherein the host cell is a prokaryotic cell or a eukaryotic cell.

11. A method of producing an antibody comprising culturing the host cell of claim 10, so that the antibody is produced.

12. A pharmaceutical composition, comprising the isolated mAb or an antigen-binding fragment thereof according to claim 1 or 4 and a pharmaceutically acceptable carrier.

13. The pharmaceutical composition of claim 12, further comprising a chemotherapeutic agent, a growth inhibitory agent, a drug unit from class of calicheamicin, an antimitotic agent, a toxin, a radioactive isotope, an anti-estrogen agent, a receptor tyrosine kinase inhibitor, a kinase inhibitor, a cell cycle inhibitor, a DNA, RNA or protein synthesis inhibitor, a RAS inhibitor, or a combination thereof.

14. A method of treating a subject with a cancer, comprising administering to the subject an effective amount of the isolated mAb or antigen-binding fragment thereof according to claim 1 or 4, wherein the cancer comprises cells expressing PD-L1.

15. The method of claim 14, further comprising co-administering an effective amount of a therapeutic agent, wherein the therapeutic agent comprises an antibody, a chemotherapy agent, an enzyme, or a combination thereof.

16. The method of claim 14, wherein the subject is a human.

* * * * *